United States Patent [19]

Shapiro

[11] 4,441,910

[45] Apr. 10, 1984

[54] THIOPHENE OR FURAN HERBICIDES

[75] Inventor: Rafael Shapiro, Wilmington, Del.

[73] Assignee: E. I. Du Pont de Nemours and Company, Wilmington, Del.

[21] Appl. No.: 345,935

[22] Filed: Feb. 8, 1982

Related U.S. Application Data

[63] Continuation-in-part of Ser. No. 247,134, Mar. 24, 1981, abandoned.

[51] Int. Cl.$^3$ ............... A01N 43/02; C07D 409/12; C07D 405/12
[52] U.S. Cl. ............................ 71/90; 544/182; 544/212; 544/253; 544/278; 544/310; 544/317; 544/319; 544/320; 544/327; 544/331; 549/65; 549/476; 71/92; 71/93
[58] Field of Search .................. 71/90, 92; 544/320, 544/331

[56] References Cited

U.S. PATENT DOCUMENTS

| 4,127,405 | 1/1978 | Levitt | 71/90 |
| 4,169,719 | 10/1979 | Levitt | 544/320 |
| 4,214,890 | 7/1980 | Levitt | 544/320 |
| 4,221,585 | 9/1980 | Levitt | 71/90 |
| 4,231,784 | 11/1980 | Levitt | 71/92 |
| 4,302,241 | 11/1981 | Levitt | 71/92 |

OTHER PUBLICATIONS

*J. Drug. Res.* 6, 123–129 (1974), Ouf et al., Thiophene Sulphonylureas Structurally Related to Antidiabetic Drugs, p. 126.

*Primary Examiner*—Mary C. Lee

[57] ABSTRACT

Novel thiophenes or furans show herbicidal activity and may also have post- and pre-emergence crop tolerance, especially to corn.

50 Claims, No Drawings

THIOPHENE OR FURAN HERBICIDES

RELATED APPLICATION

This application is a continuation-in-part of my co-pending application U.S. Ser. No. 247,134, filed Mar. 24, 1981, now abandoned.

BACKGROUND OF THE INVENTION

This invention relates to novel thiophene or furan herbicides and their use as agricultural chemicals. In particular, they are useful as pre- and post-emergence herbicides and as plant growth regulators. Certain compounds within the scope of the instant invention have shown crop selectivity and in particular have shown selectivity toward corn.

Levitt U.S. Pat. No. 4,169,719 discloses herbicidal thiophene and furan sulfonylureas such as:

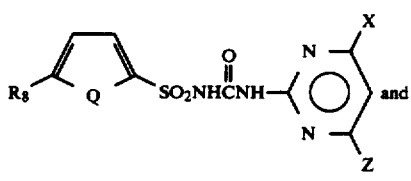

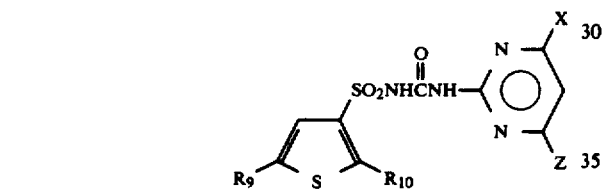

wherein
  $R_8$ is H, Cl, Br or $CH_3$;
  $R_9$ is H, Cl, Br or $CH_3$;
  $R_{10}$ is H, Cl, Br or $CH_3$;
  X is H, Cl, Br, $CH_3$, $C_2H_5$, $C_1$–$C_3$ alkoxy, $CF_3$, $SCH_3$ or $CH_2OCH_3$;
  Z is $CH_3$ or $OCH_3$; and
  Q is sulfur or oxygen.

Levitt U.S. Pat. No. 4,127,405 discloses herbicidal thiophene and furan sulfonylureas such as,

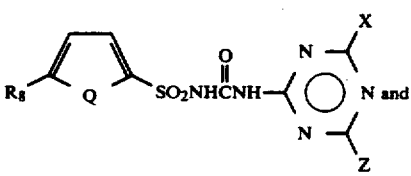

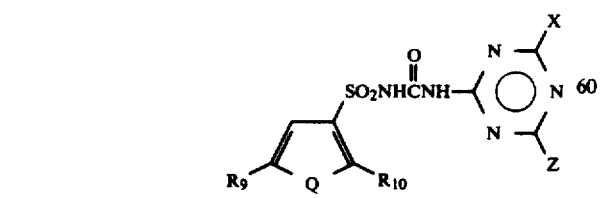

wherein $R_8$, $R_9$, $R_{10}$, Q, X and Z are defined as above.

U.S. Ser. No. 153,279 now abandoned discloses herbicidal thiophene sulfonylureas such as,

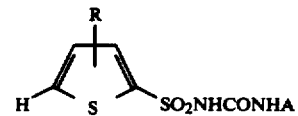

wherein
A is

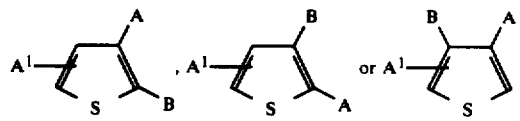

R is $C_1$–$C_4$ alkyl, $NO_2$, Cl, Br or $SO_2NR_1R_2$; and
$R_1$ and $R_2$ are independently $C_1$–$C_3$ alkyl.

U.S. Ser. No. 196,267 now abandoned discloses herbicidal thiophene sulfonylureas such as,

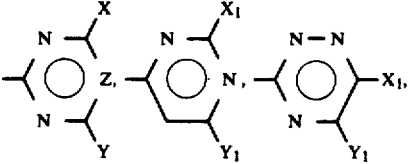

wherein
$A^1$ is H, Cl, Br, $C_1$–$C_4$ alkyl, $OCH_3$, $NO_2$ or $CF_3$;
A is

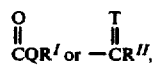

and;
B is

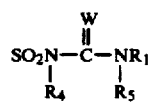

$R_4$ is H or $CH_3$;
$R_5$ is H, $CH_3$ or $OCH_3$; and
$R_1$ is

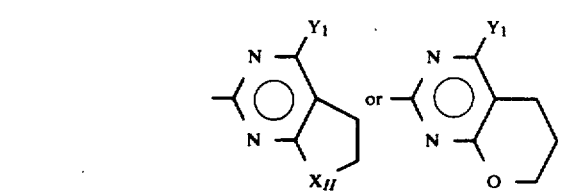

J. Drug. Res. 6, 123 (1974) discloses antidiabetic thiophene sulfonylthioureas such as,

where R is pyridyl.

The presence of undesired vegetation causes substantial damage to useful crops, especially agricultural products that satisfy man's basic food needs, such as soybeans, barley, wheat, and the like. The current population explosion and concomitant world food shortage demand improvements in the efficiency of producing these crops. Prevention or minimizing the loss of a portion of valuable crops by killing, or inhibiting the growth of undesired vegetation is one way of improving this efficiency.

A wide variety of materials useful for killing, or inhibiting (controlling) the growth of undesired vegetation is available; such materials are commonly referred to as herbicides. The need exists, however, for still more effective herbicides that destroy or retard weeds without causing significant damage to useful crops.

SUMMARY OF THE INVENTION

This invention relates to compounds of Formula I and their agriculturally suitable salts, suitable agricultural compositions containing them, and method of using them as pre-emergence and/or post-emergence herbicides.

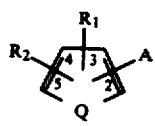

wherein
Q is O or S;
A is

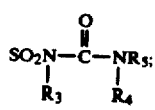

$R_1$ is $R_6S[O]_n$;
$R_6$ is $C_1$–$C_4$ alkyl, $C_3$–$C_4$ alkenyl, cyclopentyl or cyclopropylmethyl;
$R_2$ is H, Cl, Br or $CH_3$;
$R_3$ and $R_4$ are independently H or $CH_3$; n is 0, 1 or 2; and
$R_5$ is

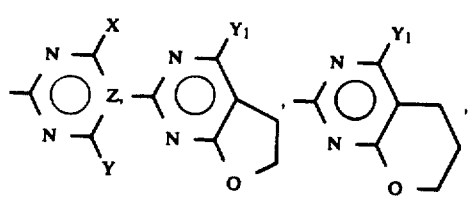

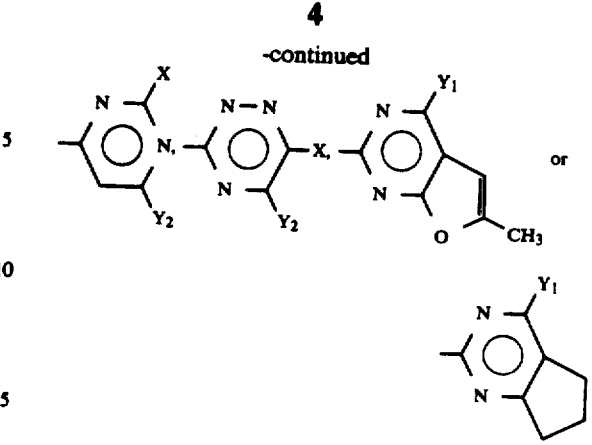

wherein
X is $CH_3$ or $OCH_3$;
Y is H, Cl, $CH_3$, $C_2H_5$, $OCH_3$, $OC_2H_5$ or $CH_2OCH_3$;
$Y_1$ is H, Cl, $CH_3$ or $OCH_3$;
$Y_2$ is $CH_3$ or $OCH_3$;
Z is CH or N;
and their agriculturally suitable salts; provided that:
both $R_3$ and $R_4$ may not simultaneously be $CH_3$, and further provided that $R_1$ and A are bonded to adjacent carbon atoms of the thiophene or furan ring.

PREFERRED COMPOUNDS

Preferred for their higher herbicidal activity and/or more favorable ease of synthesis are:
(1) Compounds of Formula I where Q is S;
(2) Compounds of Preferred (1) where $R_2$ is H;
(3) Compounds of Preferred (2) where $R_6$ is $C_1$–$C_3$ alkyl;
(4) Compounds of Preferred (3) where n is 2;
(5) Compounds of Preferred (4) where $R_5$ is

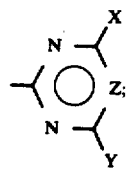

(6) Compounds of Preferred (5) where $R_3$ is H;
(7) Compounds of Preferred (6) with the structure

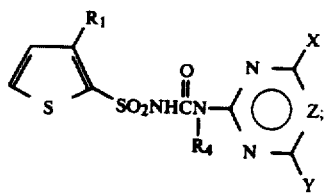

(8) Compounds of Preferred (6) with the structure

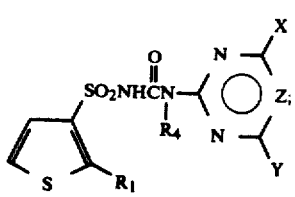

(9) Compounds of Preferred (6) with the structure

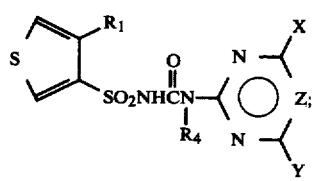

(10) Compounds of Preferred (7) where X is CH₃ or OCH₃; and Y is CH₃, OCH₃, OC₂H₅ or CH₂OCH₃;

(11) Compounds of Preferred (8) where X is CH₃ or OCH₃; and Y is CH₃, OCH₃, OC₂H₅ or CH₂OCH₃;

(12) Compounds of Preferred (9) where X is CH₃ or OCH₃; and Y is CH₃, OCH₃, OC₂H₅ or CH₂OCH₃;

(13) Compounds of Preferred (10) where R₄ is H;

(14) Compounds of Preferred (11) where R₄ is H;

(15) Compounds of Preferred (12) where R₄ is H;

(16) Compounds of Formula I where Q is O;

(17) Compounds of Preferred (16) where R₂ is H;

(18) Compounds of Preferred (17) where R₆ is C₁–C₃ alkyl;

(19) Compounds of Preferred (18) where n is 2;

(20) Compounds of Preferred (19) where R₅ is

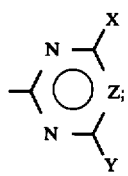

(21) Compounds of Preferred (20) where R₃ is H;

(22) Compounds of Preferred (21) with the structure

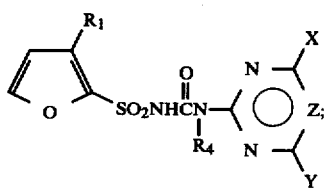

(23) Compounds of Preferred (21) with the structure

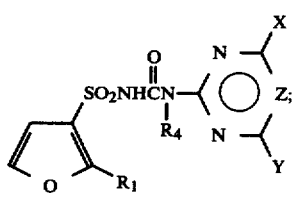

and

(24) Compounds of Preferred (21) with the structure

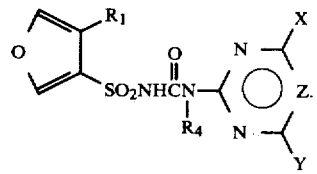

Specifically Preferred compounds for highest herbicidal activity and/or most favorable ease of synthesis are:

N-[(4,6-dimethylpyrimidin-2-yl)aminocarbonyl]-2-(methylsulfonyl)-3-thiophenesulfonamide;

N-[(4-methoxy-6-methylpyrimidin-2-yl)aminocarbonyl]-2-(methylsulfonyl)-3-thiophenesulfonamide;

N-[(4,6-dimetoxypyrimidin-2-yl)aminocarbonyl]-2-(methylsulfonyl)-3-thiophenesulfonamide;

N-[(4,6-dimethoxy-1,3,5-triazin-2-yl)aminocarbonyl]-2-(methylsulfonyl)-3-thiophenesulfonamide;

N-[(4,6-dimethyl-1,3,5-triazin-2-yl)aminocarbonyl]-2-(methylsulfonyl)-3-thiophenesulfonamide;

N-[(4-methoxy-6-methyl-1,3,5-triazin-2-yl)aminocarbonyl]-2-(methylsulfonyl)-3-thiophenesulfonamide;

N-[(4,6-dimethoxypyrimidin-2-yl)(methyl)aminocarbonyl]-2-(methylsulfonyl)-3-thiophenesulfonamide;

N-[(4-methoxy-6-methylpyrimidin-2-yl)(methyl)aminocarbonyl]-2-(methylsulfonyl)-3-thiophenesulfonamide;

N-[(4,6-dimethoxy-1,3,5-triazin-2-yl)(methyl)aminocarbonyl]-2-(methylsulfonyl)-3-thiophenesulfonamide; and N-[(4-methoxy-6-methyl-1,3,5-triazin-2-yl)(methyl)aminocarbonyl]-2-(methylsulfonyl)-3-thiophenesulfonamide.

The invention also relates to compounds of Formula II which are useful as intermediates for the preparation of compounds of Formula I.

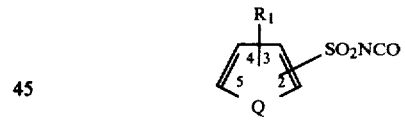

wherein

Q is O or S;

R₁ is R₆S[O]ₙ;

R₆ is C₁–C₄ alkyl, C₃–C₄ alkenyl, cyclopentyl or cyclopropylmethyl; and n is 0 or 2;

provided that:

R₁ and the sulfonylisocyanate group are bonded to adjacent carbon atoms of the furan or thiophene ring.

PREFERRED INTERMEDIATES

Preferred intermediates for the higher herbicidal activity of products derived from them and/or their more favorable ease of synthesis are:

(1) Compounds of Formula II with the structure

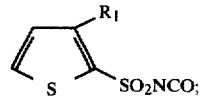

(2) Compounds of Formula II with the structure

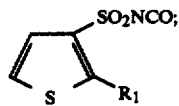

(3) Compounds of Formula II with the structure

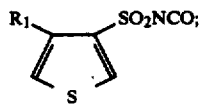

and (4) Compounds of Preferred (2) wherein $R_1$ is $R_6SO_2$, and $R_6$ is $C_1-C_3$ alkyl.

The invention also relates to compounds of Formula III which are useful as intermediates for the preparation of compounds of Formula I.

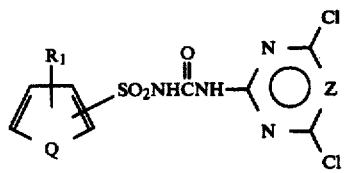

wherein
Q is O or S;
$R_1$ is $R_6S[O]_n$;
$R_6$ is $C_1-C_4$ alkyl, $C_3-C_4$ alkenyl, cyclopentyl or cyclopropylmethyl;
n is 0 or 2; and
Z is CH or N.
provided that:
$R_1$ and the sulfonylureido group are bonded to adjacent carbon atoms of the furan or thiophene ring.

SYNTHESIS

Many of the compounds of Formula IA, IB and IC, wherein n=0 or 2, $R_3$=H and Q, $R_2$, and $R_6$ are as previously defined, may be prepared as shown in Equation 1 by the reaction of the appropriately substituted furan or thiophenesulfonylisocyanates, II, wherein n=0 or 2 and Q, $R_2$ and $R_6$ are as previously defined, with the appropriate heterocyclic amine, V, wherein $R_4$ and $R_5$ are as previously defined.

Equation 1

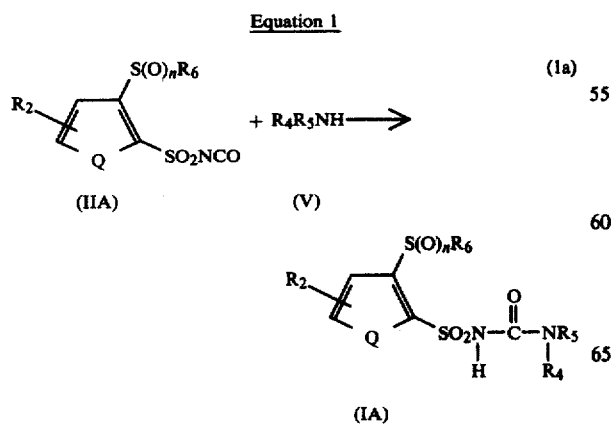

-continued
Equation 1

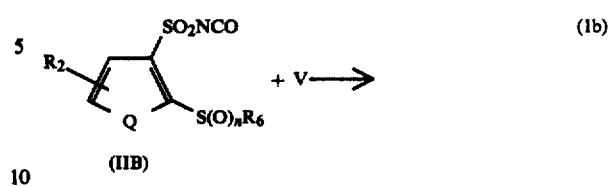

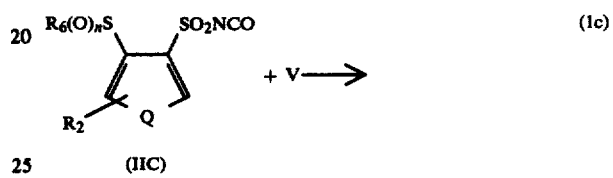

The reactions of Equation 1 are generally carried out by contacting a solution of the isocyanates of Formula II in an inert solvent such as methylene chloride or acetonitrile with the appropriate heterocyclic amine V and isolating the product either by filtration or by evaporation of solvent and trituration or column chromatography.

From the compounds of Formula VI, wherein A, Q, $R_2$ and $R_6$ are as previously defined, the compounds of Formula VIII may be prepared by oxidation, as shown in Equation 2.

Equation 2

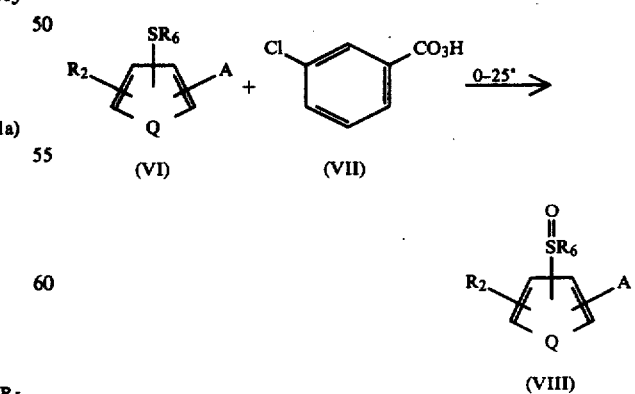

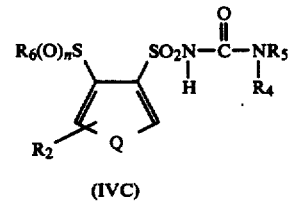

The oxidation of Equation 2 is carried out by mixing equimolar quantities of the appropriate sulfide (VI) and m-chloroperbenzoic acid (VII) in an inert solvent such as methylene chloride at 0°-25° and isolating the product by column chromatography or filtration.

The compounds of Formula IX, wherein $R_6=C_1-C_4$ alkyl, cyclopentyl and cyclopropylmethyl, and Q, $R_2$ and A are as previously defined, may be prepared by oxidation as in Equation 2, but using twice the equivalent amount of oxidant (VII) and heating the solution at 40°-70° for 1–7 days.

Equation 3

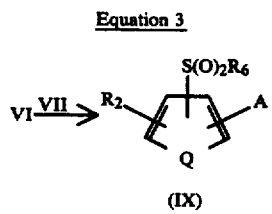

Alternatively, oxidation of sulfides of Formula VI to sulfoxides of Formula VIII or sulfones of Formula IX can be carried out employing aqueous hydrogen peroxide in acetic acid by methods well known in the art.

Compounds of Formula I can also be prepared by the method described in Equation 4.

Equation 4

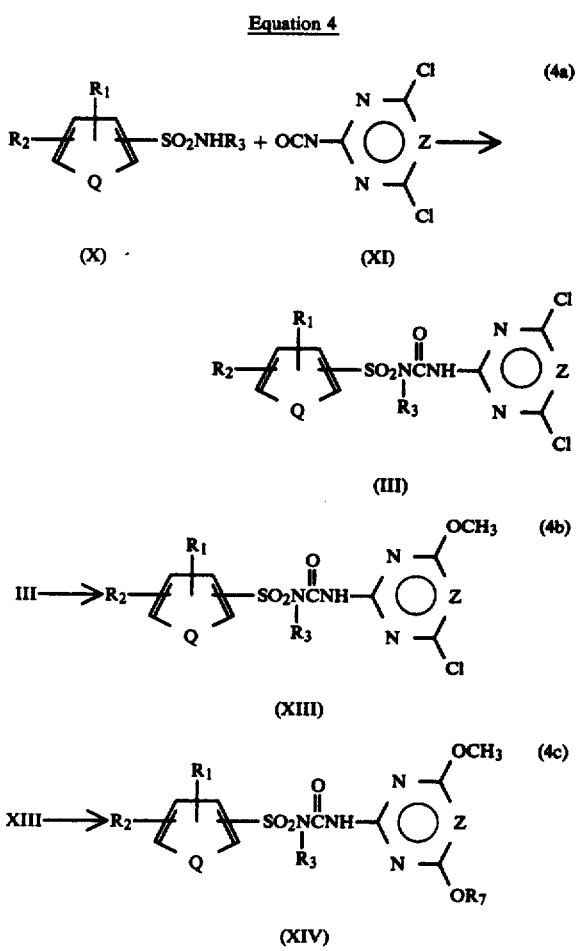

wherein Q, $R_1$, $R_2$, $R_3$ and Z are as previously defined, and $R_7$ is $CH_3$ or $C_2H_5$.

Reaction Step (4a)

In Reaction Step (4a), a furan or thiophenesulfonamide of Formula X is contacted with a heterocyclic isocyanate of Formula XI to yield a sulfonylurea of Formula III.

The heterocyclic isocyanates used in Reaction (4a) may be prepared according to methods described in Swiss Pat. No. 579,062, U.S. Pat. No. 3,919,228, U.S. Pat. No. 3,732,223 and *Angew Chem. Int. Ed.* 10, 402 (1976), the disclosures of which are herein incorporated by reference.

The furan or thiophene sulfonamide and the heterocyclic isocyanate are contacted in the presence of an inert organic solvent, for example, acetonitrile, tetrahydrofuran (THF), toluene, acetone or butanone. Optionally, a catalytic amount of a base, such as 1,4-diazabicyclo[2.2.2]octane (DABCO), potassium carbonate, sodium hydride or potassium tert-butoxide, may be added to the reaction mixture. The quantity of base constituting a catalytic amount would be obvious to one skilled in the art. The reaction mixture is preferably maintained at a temperature of about 25° to 110° C., and the product can generally be recovered by cooling and filtering the reaction mixture. For reasons of efficiency and economy, the preferred solvents are acetonitrile and THF, and the preferred temperature range is about 60° to 85° C.

Reaction Steps (4b) and (4c)

In Reaction Steps (4b) and (4c), one or two of the chlorine atoms on the pyrimidinyl or triazinyl ring of the compound of Formula III is displaced by an alcohol. Generally, this may be done by contacting the compound of Formula III with methanol or methoxide. Thus, in Reaction Step 4b, a compound of Formula III may be contacted with at least one equivalent of methanol. This reaction is sluggish, however, and it is preferred to contact the compound of Formula III with at least two equivalents of sodium methoxide in either methanol, acetonitrile, THF or dimethylformamide.

It should be noted that two equivalents of methoxide are required for Reaction Step (4b) whereas only one equivalent of methanol is needed for the same process. This difference is due to the reaction which is believed to occur between the methoxide and the sulfonyl nitrogen of the sulfonamide of Formula III. When methoxide is used, the first equivalent of base removes a proton from the sulfonyl nitrogen, and it is only the second equivalent which effects displacement of the halogen. As a result, two equivalents of methoxide are required. The resulting salt must be acidified, e.g., with sulfuric, hydrochloric or acetic acid, to yield a compound of Formula XIII. Applicant, of course, does not intend to be bound by the mechanism described above.

In Reaction Step (4c) a compound of Formula XIII, is contacted with either one equivalent of alkanol, $R_7OH$, or with two equivalents of alkoxide, $R_7O^-$ where $R_7$ is as described above.

When $R_7=CH_3$, Reaction Steps (4b) and (4c) may be combined. Thus, a compound of Formula III may be contacted either with at least two equivalents of methanol, or with at least three equivalents of methoxide. In Reaction Step 4b, certain reaction conditions will favor displacement of only one chlorine atom. These conditions are the use of low temperatures and the slow addition of the stoichiometric amount of alkoxide or alkoxide-generating base to the medium containing the compound of Formula III.

Both Reaction Steps (4b) and (4c) are preferably run at temperatures within the range of about −10° to 80°

C., the range of about 0° to 25° C. being more preferred. Reaction Steps (4b) and (4c) are more sluggish when alkanol is used instead of alkoxide, and more drastic conditions are required for the reaction to go to completion. Thus, higher temperatures, up to and including the boiling point of the alkanol itself, are required.

The novel furan or thiophenesulfonyl isocyanates of Formula II, wherein n=0 or 2 and Q and $R_1$ are as previously defined, are important intermediates in the preparation of the compounds of this invention. The method by which they can be prepared from sulfonamides of Formula XV, wherein n=0 or 2 and Q, $R_6$ and $R_2$ are as previously defined, is shown in Equation 5, by methods taught in G. Levitt, U.S. Pat. No. 4,169,719, the disclosures of which are herein incorporated by reference.

Equation 5

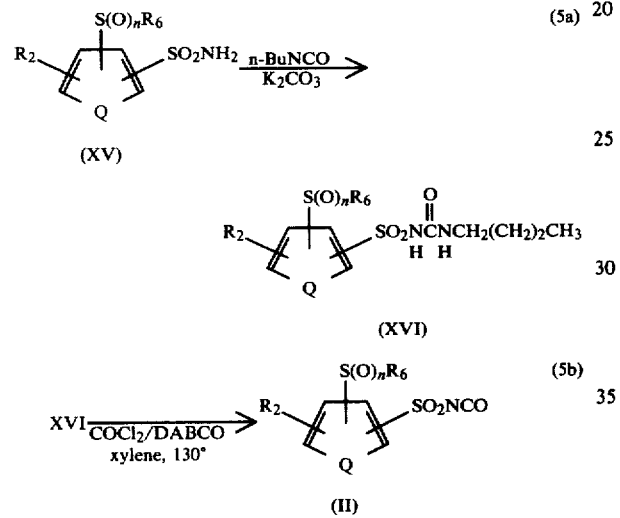

The preparation of the novel sulfonamides of Formulae XXIV or XXV may be accomplished by the method outlined in Equation 6.

Equation 6

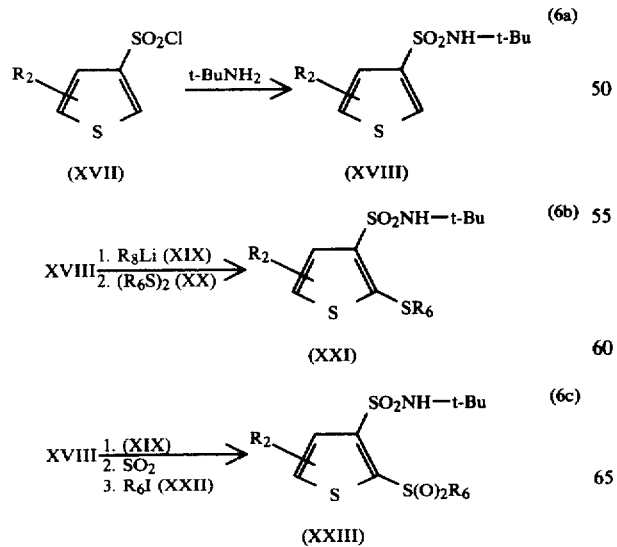

-continued
Equation 6

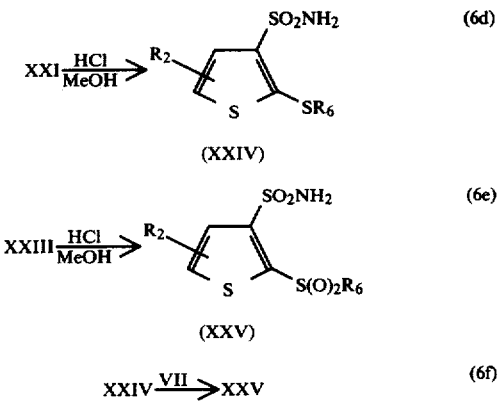

wherein $R_2$ and $R_6$ are as previously defined, and $R_8$ = n-Bu, $-N(i-C_3H_7)_2$, t-Bu, or

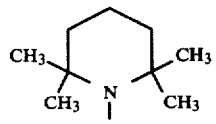

The sulfonyl chlorides of Formula XVII are described by H. D. Hartough in "The Chemistry of Heterocyclic Compounds," v. 3, Interscience Publishers, Inc., N.Y. 1952. These may be converted to the corresponding N-t-butyl sulfonamides (XVIII) by admixture with at least twice the equivalent amount of t-butylamine in an inert solvent, such as ether, filtration of the amine hydrochloride, and evaporation of solvent. The lithiation of thiophenes and of aromatic N-t-butylsulfonamides with n-butyllithium, t-butyllithium, lithium diisopropylamide and lithium 2,2,6,6-tetramethyl piperidide is reviewed by H. W. Gschwend and H. R. Rodriguez in Org. React., 26, 1 (1979), and is generally carried out by cooling to −78° a solution of twice the equimolar amount of XIX, kept under an inert atmosphere, in an ethereal solvent such as diethyl ether or THF, and adding a solution of the compound of Formula XVIII. The compounds of Formula XXI may be prepared as shown in Equation (6b) by adding an equimolar quantity of the appropriate disulfide (XX), allowing the mixture to warm to room temperature, washing the mixture with acidic brine, and evaporation of the solvent.

Alternatively, as shown in Equation (6c), in order to prepare the compounds of Formula XXIII, the lithiation mixture may be treated with an equimolar quantity of sulfur dioxide, allowing the mixture to warm to room temperature, filtration of the solid precipitate, dissolution of this salt in ethanol and adding an equimolar amount of the appropriate alkyl iodide (XXII). This alkylation step may be carried out at temperatures of 25° to 78°. The cooled reaction mixture may be diluted with dilute aqueous hydrochloric acid to precipitate the product (XXIII). The t-butyl sulfonamides of Formula XXI and XXIII may be converted to the compounds of Formulae XXIV and XXV, respectively, by heating in methanol containing at least an equimolar quantity of hydrochloric acid, followed by concentration of the reaction mixture and precipitation of the product with ether. Compounds of Formula XXV may be prepared by the reaction of Equation (6f), which is carried out as described for Equation 3.

An alternate preparation of the thiophene sulfonamides of Formula XXV is described in Equation 7.

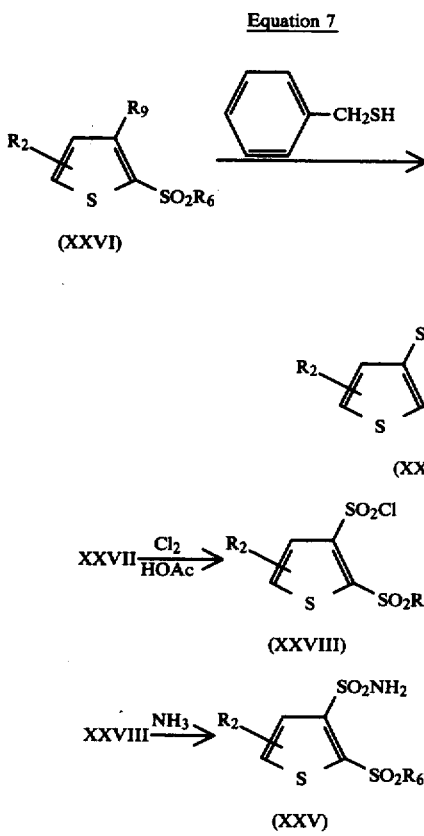

wherein
$R_6 = C_1$–$C_4$ alkyl, cyclopentyl, cyclopropylmethyl;
$R_9 = $ Cl, Br; and
$R_2 = $ H, $CH_3$, Cl and 4-Br.

The reaction of Equation (7a) is accomplished by mixing equimolar quantities of the appropriate halide (XXVI) with an equimolar quantity of benzyl mercaptan in a polar solvent, such as dimethylformamide, containing an equimolar amount of a strong base, such as sodium methoxide or sodium hydride, heating at a temperature between 50° and 120°, and isolating the product by precipitation with ice-water and washing with hexane. The sulfides of Formula XXVII are converted to the sulfonyl chlorides (XXVIII) as shown in Equation (7b) by contacting with at least three equivalents of chlorine in acetic acid according to the procedure of R. F. Langler, *Can. J. Chem.*, 54, 498 (1976). The sulfonyl chlorides can be precipitated by the addition of ice-water to the chlorination mixture. Ammonolysis of thiophene sulfonyl chlorides (XXVIII) is described by Hartough, loc. cit. The sulfone (XXVI), wherein $R_2 = $ H, $R_6 = CH_3$ and $R_9 = $ Br, is described by D. Spinelli, et al., *J. Chem. Soc. Perkin* II, 1972, 441. The preparation of analogous compounds of Formula XXVI will be obvious to one skilled in the art.

The compounds of Formulae XXXI and XXXII, wherein $R_2$ is as previously defined, may be prepared according to the method outlined in Equation 8.

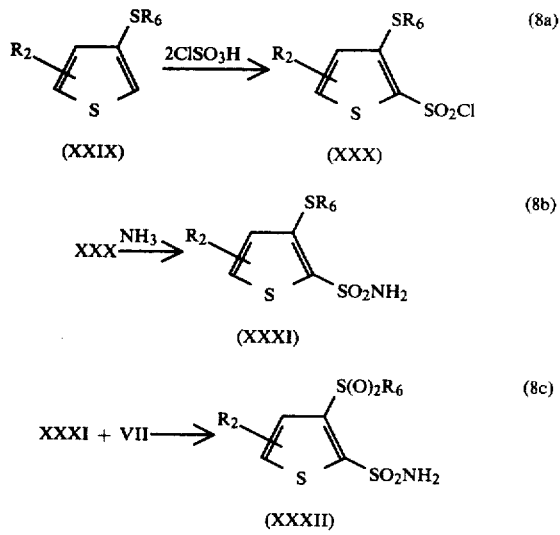

The compounds of Formula XXX, wherein R is as previously defined and $R_6$ is $C_1$–$C_4$ alkyl or cyclopentyl, may be prepared by adding twice the equimolar amount of chlorosulfonic acid, diluted in an inert solvent, such as dichloromethane, to the appropriate 3-thienyl alkyl sulfide (XXIX) at temperatures between $-30°$ and $25°$, washing the mixture with ice-water and evaporating the solvent. These may be converted to the appropriate compounds of Formula XXXI by contacting with ammonia. The sulfides of Formula XXXI may be oxidized exactly as described in Equation 2 to compounds of Formula XXXII.

Alternatively, the methods described in Equation 6 may be applied to the compounds of Formula XXXIII to produce compounds of Formulae XXXI and XXXII as shown in Equation 9.

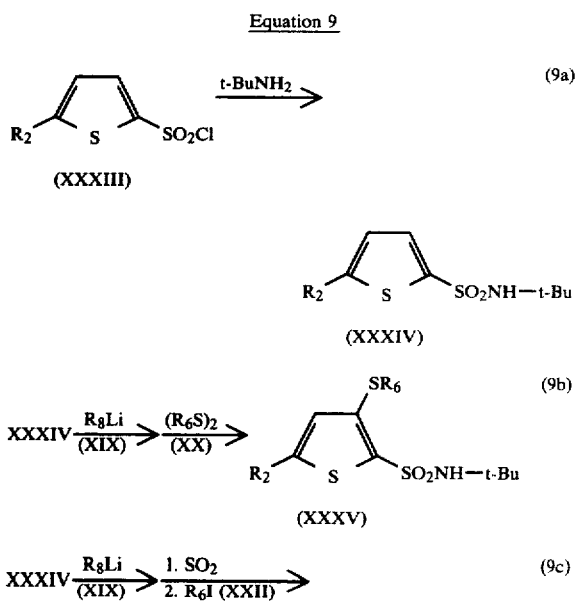

-continued
Equation 9

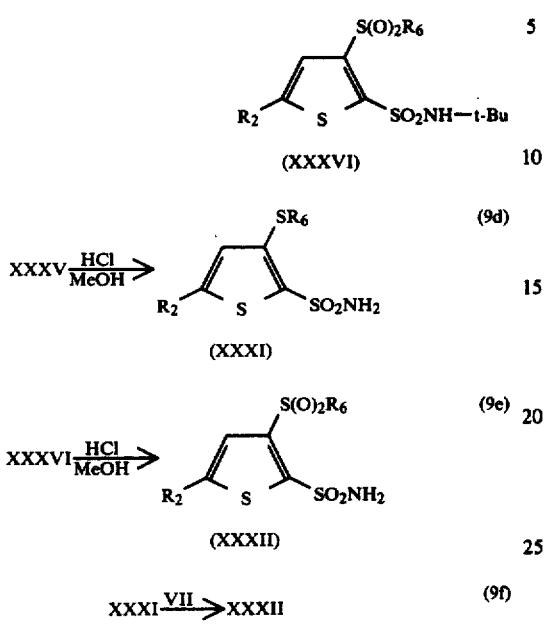

wherein $R_2$, $R_6$ and $R_8$ are as previously defined.

The preparation of the compounds of Formulae XLII and XLIV can be accomplished according to the method outlined in Equation 10.

Equation 10

-continued
Equation 10

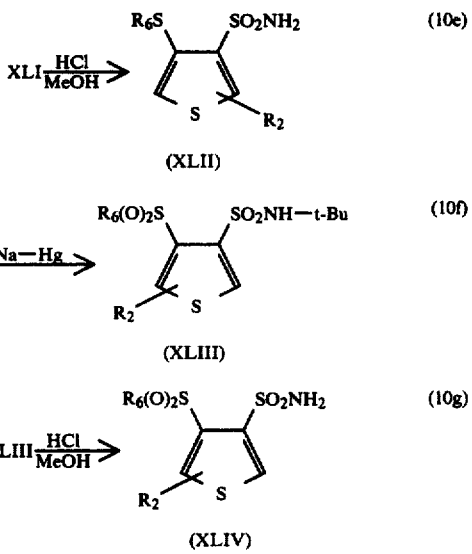

wherein
$R_{10}$=Cl or $CH_3$;
$R_{11}$=Cl, Br or $CH_3$, provided that $R_{10}$ and $R_{11}$ cannot both be $CH_3$;
$R_2$=H, Cl, Br or $CH_3$; and
$R_6$ and $R_8$ are as previously defined.

Starting with sulfonyl chlorides of Formula XXXVII (Hartough, loc. cit.), the procedure described above can be used, analogously to Equation 6, to prepare the compounds of Formulae XXXIX and XL. These dihalocompounds may be partially dehalogenated by contacting with two equivalents of 5% sodium amalgam in an alcoholic or aqueous alcoholic solution at 25° to 78°, followed by acidification with aqueous hydrochloric acid at 0° and filtration or extraction of the products of Formulae XLI or XLIII wherein $R_2$=Cl or Br. The 2-halo and 5-halo isomers may be separated by column chromatography. The totally dehalogenated compounds of Formulae XLI or XLIII wherein $R_2$=H may be prepared by using three or more equivalents of the sodium amalgam in the reaction. These compounds may be converted to the compounds of Formulae XLII or XLIV as previously described.

The furan sulfonamides of Formula XV may be prepared from halofurans or halofuran carboxylic acids, which are described by A. P. Dunlop and F. N. Peters in "The Furans," Reinhold, New York, 1953.

The sulfonamides of Formula XLII or XLIX may be obtained by the reactions of Equation 11.

Equation 11

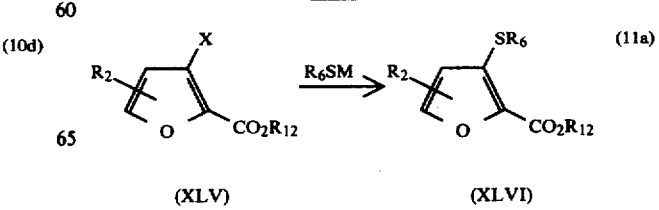

Equation 11 -continued

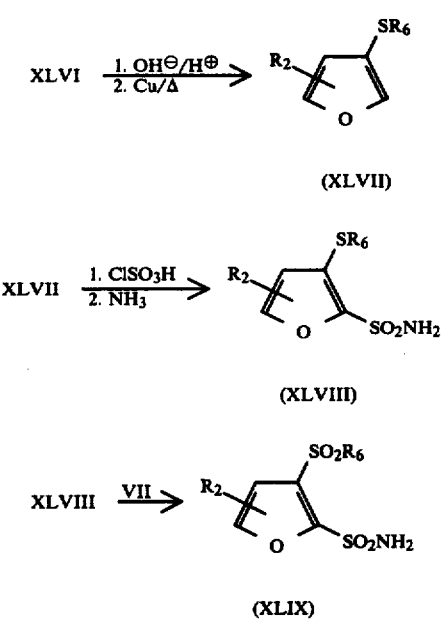

wherein
X = Br or I;
M = Na, K or Cu; and
$R_2$ and $R_6$ are as previously defined.

The reaction of Equation 11a is carried out by contacting a compound of Formula XLV with an alkali metal or copper (I) salt of the appropriate alkyl thiol in a polar, aprotic solvent (such as dimethylformamide or N-methylpyrrolidone) at 50° to 150° C., followed by extraction or filtration from dilute aqueous acid. The compounds of Formula XLVI wherein $R_{12}$ is $CH_3$ or $C_2H_5$ may be saponified and acidified to afford the compounds of Formula XLVI wherein $R_{12}$ is H. These may be decarboxylated by heating in a solvent such as quinoline in the presence of copper powder or copper bronze. The reactions of Equation 11c and 11d may be carried out as described for Equations 8a, 8b and 8c.

The sulfonamides of Formula LIII and LIV may be prepared from sulfonyl chlorides of Formula LII in a manner exactly analogous to that described for Equations 6b–6e.

Equation 12

![Equation 12a structure showing L to LI conversion]

(L) → (LI)
1. BuLi
2. $SO_2$

Equation 12 -continued (12b) (LII)

LI $\xrightarrow{\text{HOAc}}$ [N-chlorosuccinimide structure] → $R_2$-furan-$SO_2Cl$ (12c) LII $\xrightarrow{\text{as in Equations 6b and 6d}}$ $R_2$-furan with $SO_2NH_2$ and $SR_6$ (LIII)

(12d) LII $\xrightarrow{\text{as in Equations 6c and 6e}}$ $R_2$-furan with $SO_2NH_2$ and $SO_2R_6$ (LIV)

wherein
X is Br or I;
$R_2$ and $R_6$ are as previously defined.

The preparation of the sulfonyl chlorides LII is shown in Equations 12a and 12b, wherein an ethereal solution of the appropriate bromo- or iodofuran L is treated with one equivalent of butyllithium at −78° to −100° C., one equivalent of sulfur dioxide is added, and the salt LI is filtered. The reaction of Equation 12b is carried out by cooling a suspension or solution of LI in an inert solvent such as acetone to −20° to 0° C., adding one equivalent of a weak acid, such as acetic acid, followed by one equivalent of a chlorinating agent, such as N-chlorosuccinimide. The product is isolated by evaporation of the solvent, and washing an ether solution of the residue with water to remove the by-products of the reaction. This solution of LII may be used in the sequence described for equations 6b and 6d or 6C and 6e to produce compounds of Formula LIII or LIV, respectively.

The sulfonamides of Formulas LIX or LX may be prepared according to the reactions of Equation 13.

Equation 13

(LV) $CH_3O_2C$-furan-$R_2$ with $SO_2Cl$ $\xrightarrow[\text{2. } OH^\ominus; H^\oplus]{\text{1. t-BuNH}_2}$ (13a)

Equation 13 -continued

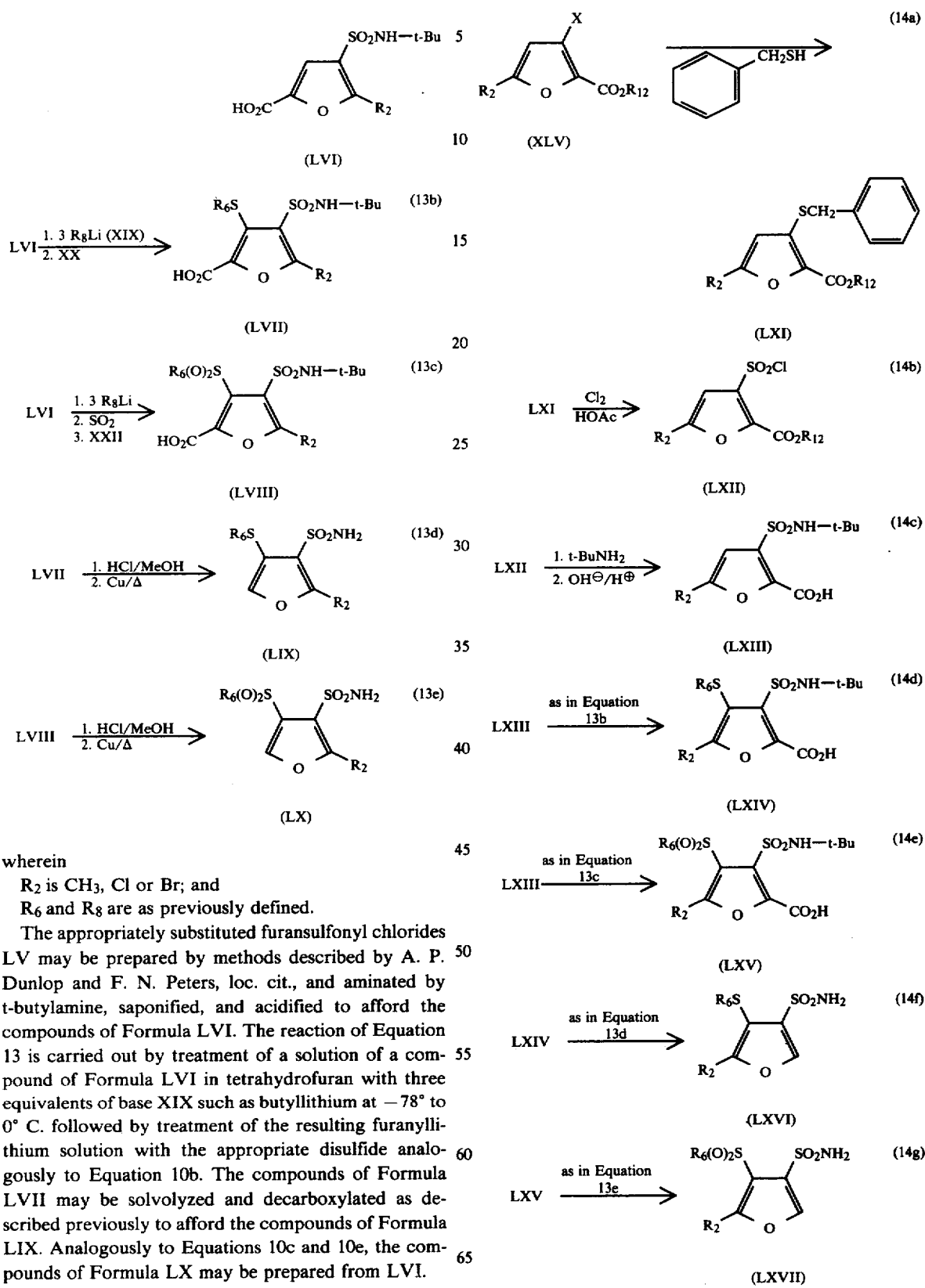

wherein

R$_2$ is CH$_3$, Cl or Br; and

R$_6$ and R$_8$ are as previously defined.

The appropriately substituted furansulfonyl chlorides LV may be prepared by methods described by A. P. Dunlop and F. N. Peters, loc. cit., and aminated by t-butylamine, saponified, and acidified to afford the compounds of Formula LVI. The reaction of Equation 13 is carried out by treatment of a solution of a compound of Formula LVI in tetrahydrofuran with three equivalents of base XIX such as butyllithium at −78° to 0° C. followed by treatment of the resulting furanyllithium solution with the appropriate disulfide analogously to Equation 10b. The compounds of Formula LVII may be solvolyzed and decarboxylated as described previously to afford the compounds of Formula LIX. Analogously to Equations 10c and 10e, the compounds of Formula LX may be prepared from LVI.

The compounds of Formula LXVI and LXVII may be prepared by the reactions of Equation 14.

wherein $R_{12}$ is $CH_3$ or $C_2H_5$;

$R_2$ is $CH_3$, Cl or Br; and $R_6$ and $R_8$ are as previously defined.

The reaction of Equations 14a and 14b are carried out as described for Equations 7a and 7b, and the reactions of Equations 14c, 14d, 14e, 14f, and 14g are carried out as described for Equations 13a, 13b, 13c, 13d, and 13e, respectively.

Finally, the compounds of Formula LXVIII or LXIX may be prepared according to the method of Equation 15, which is carried out as described for Equation 10d.

Equation 15

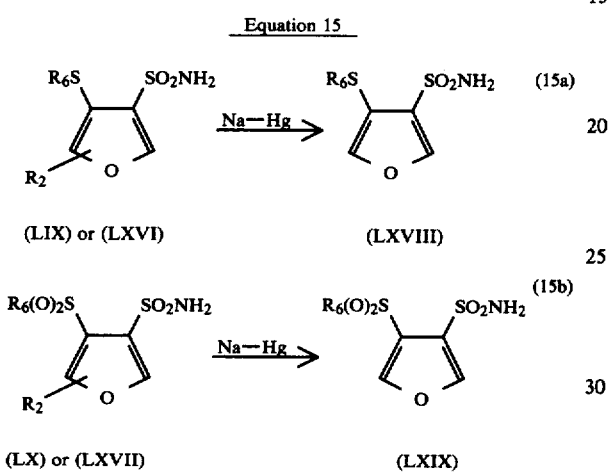

(LIX) or (LXVI)   (LXVIII)

(LX) or (LXVII)   (LXIX)

The synthesis of heterocyclic amines of Formula V has been reviewed in "The Chemistry of Heterocyclic Compounds," a series published by Interscience Publishers, Inc., N.Y. and London. 2-Aminopyrimidines are described by D. J. Brown in The Pyrimidines, Vol. 26 of this series. The 2-amino-1,3,5-triazines are reviewed by K. R. Huffman in "the Triazines" of this same series. The synthesis of triazines is also described by F. C. Schaefer, U.S. Pat. No. 3,154,547, and by K. R. Huffman and F. C. Schaefer, *J. Org. Chem.*, 28, 1816 (1963). The 4-aminopyrimidines are disclosed in U.S. Pat. No. 4,221,585, and the 2-amino-1,3,4-triazines are disclosed in U.S. Pat. No. 4,120,691. The synthesis of the bicyclic heterocyclic amines LXX and LXXI wherein $Y_1$ is as previously defined are prepared as described in the unexamined European Patent No. 15-683, published Sept. 17, 1980.

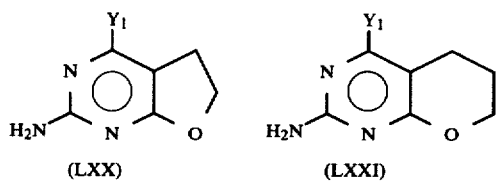

(LXX)   (LXXI)

The pyrimidine intermediate (LXXIX) in which $Y_1$ is methyl have been reported in the literature by E. Bisagni et al., [*Bull. Soc. Chim. Fr.*, 803 (1969)]. An apparently more efficient procedure is depicted in Equation 16.

Equation 16

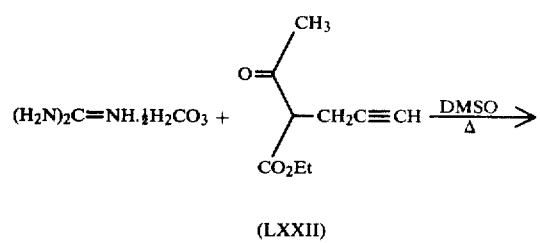

(LXXII)

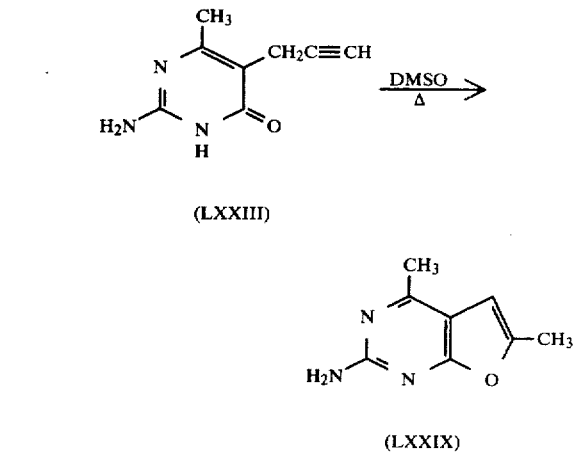

(LXXIII)

(LXXIX)

The keto-ester precursors (LXXII) are prepared by well known literature methods, e.g., J. F. Tinker and T. E. Whatmough, *J. Amer. Chem. Soc.*, 74 5235 (1952).

Treatment of (LXXII) with an excess of guanidine carbonate in an organic solvent, preferably a polar aprotic solvent such as dimethylsulfoxide (DMSO), dimethylformamide (DMF), or N,N-dimethylacetamide, at a temperature of 80° to 200°, preferably 100° to 160°, ambient pressure and preferably under an inert atmosphere, yields both (LXXIX) and (LXXIII) as products. The products are isolated upon dilution of the reaction mixture with, for example, acetone and water successively. Higher reaction temperatures and longer reaction times (e.g., in DMSO at 130°–150° for 2 to 8 hours) favor the production of the furopyrimidine (LXXIX) over the uncyclized pyrimidine (LXXIII).

The pyrimidine intermediate (LXXXIII) in which $Y_1$ is a chlorine atom may be prepared by condensing the known ethyl 2-carbethoxy-4-pentynoate (LXXX) with guanidine carbonate in an alcohol solvent such as ethanol to give the intermediate pyrimidine (LXXXI) as shown in Equation 17.

Equation 17

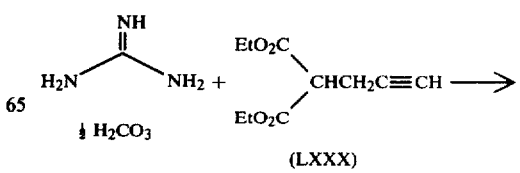

(LXXX)

Equation 17 (continued)

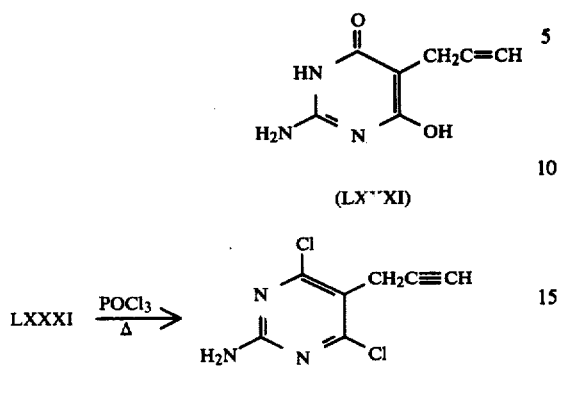

Equation 18 (continued)

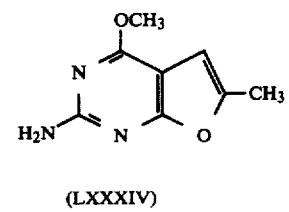

The intermediates of Formula LXXXV in which $Y_1$ is hydrogen may be prepared by reduction of the chlorofuropyrimidine (LXXXIII) with a reducing agent such as zinc dust in acetic acid or p-toluenesulfonyl hydrazide; the latter by a procedure similar to that described by Albert and Royer, *J. Chem. Soc.*, 1148 (1949).

Equation 19

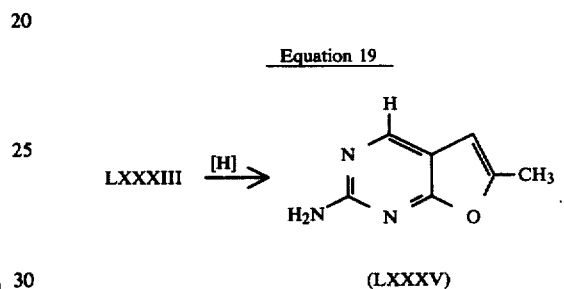

Conversion to the dichloropyrimidine (LXXXII) may be accomplished by heating (LXXXI) in phosphorus oxychloride. The product (LXXXII) may be isolated by removal of the phosphorus oxychloride at reduced pressure, trituration of the residue with ice-water and filtration of the solid product. Reaction of this dichloropyrimidine (LXXXII) with two equivalents of an aqueous alkali metal hydroxide, such as sodium hydroxide, yields the cyclized furopyrimidine (LXXXIII) as a major product. The reaction is best carried out in the presence of a solubilizing organic solvent that is water miscible, such as tert-butanol, dioxane or tetrahydrofuran, and at temperatures from 20° to 100° or conveniently at the boiling point of the solvent mixture used. The product may be isolated by cooling the mixture and further dilution with water to effect precipitation.

Compounds of Formula LXXXIV which are also used as intermediates for the sulfonylurea herbicides of this invention may be prepared from the chlorofuropyrimidine. (LXXXIII) by reaction with sodium methoxide in boiling methanol, as shown in Equation 18. The product is obtained upon evaporation of the methanol solution and trituration of the residue with cold water and subsequent filtration.

Many of the aminoheterocyclic intermediates of Formula V where $R_4$ is methyl or methoxy may be prepared by the following two-step procedure as shown in Equation 20.

Equation 20

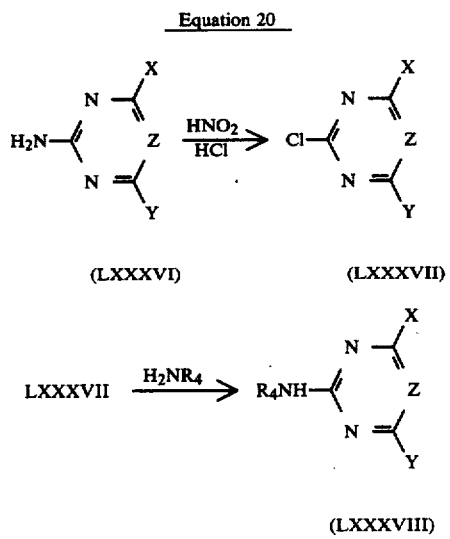

wherein X, Y and Z are as previously defined and $R_4$ is methyl or methoxy.

A solution of the amine (LXXXVI) in concentrated hydrochloric acid is treated with sodium nitrite solution and the chloro compound (LXXXVII) is isolated in the usual manner by filtration of the acidic solution. A representative procedure is described by Bee and Rose in *J. Chem. Soc. C*, 2031 (1966), for the case in which $Z=CH$, and $X=Y=OCH_3$. Displacement of the chlorine of (LXXXVII) may be accomplished by heating

Equation 18

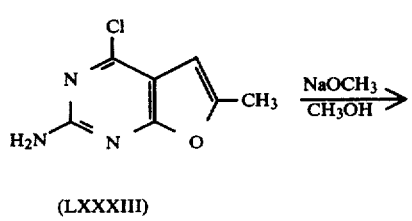

with an excess of methylamine or O-methyl hydroxylamine in water to obtain the methylamino heterocycle (LXXXVIII) or N-methoxyamino heterocycle (LXXXVIII).

The synthesis of the bicyclic amines of Formula LXXXIX is disclosed in Eur. Pat. No. 803 005 05.7.

Agriculturally suitable salts of compounds of Formula I are also useful herbicides and can be prepared in a number of ways known to the art. For example, metal salts can be made by treating compounds of Formula I with a solution of an alkali or alkaline earth metal salt having a sufficiently basic anion (e.g. hydroxide, alkoxide, carbonate or hydride) quaternary amine salts can be made by similar techniques. Detailed examples of such techniques are given in U.S. Pat. No. 4,127,405, the disclosure of which is herein incorporated by reference.

In the following examples, unless otherwise indicated, all parts are by weight and temperatures in °C.

EXAMPLE 1

3-Benzylthio-2-thienyl methyl sulfone (XXVII)

To a solution of 2 g of sodium methoxide in 100 ml of dimethylformamide was added 6 ml of benzyl mercaptan followed by 10 g of 3-bromo-2-thienyl methyl sulfone. The temperature rose to 70°. The mixture was stirred at room temperature for 16 hours and then at 70° for 1 hour. Most of the dimethylformamide was evaporated at reduced pressure and ice-water was added to the residue. The resulting solid was filtered, washed with ice-water and hexane to afford 14 g of crude XXVII. A dried sample of this material had m.p. 95°–97° and peak at 4.2 in the NMR spectrum (CDCl$_3$), consistent with an aromatic benzyl sulfide.

EXAMPLE 2

2-Methylsulfonyl-3-thiophenesulfonyl chloride (XXVIII)

To 14 g of (XXVII) in 200 ml of acetic acid was added chlorine gas at 15°–20° until a green color persisted. The mixture was stirred for 1 hour at 15°–20° and then purged with nitrogen, poured into ice-water, and then with hexane to afford 13 g of crude (XVIII). A dried sample had m.p. 116°–120° and an NMR spectrum (CDCl$_3$) which showed peaks at $\delta$3.4 ($\underline{CH_3SO_2}$—) and $\delta$7.8 (AB, J=5 Hz), consistent with a thienyl methyl sulfone.

EXAMPLE 3

2-Methylsulfonyl-3-thiophenesulfonamide (XXV)

To 10 g of (XXVIII) in 200 ml of ethyl acetate was added 5 ml of liquid ammonia with stirring at 0°. The mixture was allowed to attain room temperature, evaporated and the solid product was washed with ice-water. A dried sample of (XXV) had m.p. 242°–244°.

EXAMPLE 4

N-(Butylaminocarbonyl)-2-methylsulfonyl-3-thiophenesulfonamide

A solution of 4.0 g of (XXV) and 2.0 ml of n-butyl isocyanate in 50 ml of 2-butanone was heated at reflux with 2.0 g of anhydrous potassium carbonate for 7 hours. The cooled mixture was filtered, the solids were washed with ice-water, and the combined filtrate and washings were acidified with 2 N HCl. The precipitate was filtered and washed with water to afford 2.4 g of the n-butylaminocarbonyl derivative of (XXV), m.p. 173.5°–174°. The NMR spectrum (CDCl$_3$/DMSO-d$_6$) exhibited peaks at $\delta$0.7–1.7 (m, 7H), 2.8–3.3 (m, 2H) and 6.4 (t, 1H) indicative of an N-butylurea.

EXAMPLE 5

2-Methylsulfonyl-3-thiophenesulfonyl isocyanate

A suspension of 3.3 g of the (N-(n-butylamino carbonyl) derivative of (XXV) in 75 ml of xylene containing 0.5 g of DABCO was heated to 125°–130° and a solution of 1.8 ml of liquid phosgene in 2 ml of xylene was added. The mixture was heated at reflux for an additional 1.5 hour, cooled under nitrogen, and concentrated to dryness in vacuo. A sample of the crude product displayed a characteristic sulfonyl isocyanate band in the IR at 2200 cm$^{-1}$.

EXAMPLE 6

N-[(4-Methoxy-6-methylpyrimidin-2-yl)aminocarbonyl]-2-methylsulfonyl-3-thiophenesulfonamide The crude 2-methylsulfonyl-3-thiophenesulfonyl isocyanate described above was dissolved in 100 ml of methylene chloride and 10 ml of this solution (0.3 g of crude isocyanate) was added to 200 mg of 4-methoxy-6-methyl-2-pyrimidinamine in methylene chloride containing a few crystals of DABCO. After stirring 3 days at room temperature, the precipitate was filtered and washed with ether to afford 250 mg of product, m.p. 204.5°–206° d. The IR spectrum showed a carbonyl absorption at 1680 cm$^{-1}$ indicative of a sulfonylurea.

Using the techniques described in Equations 1–20 and Examples 1–6, the following compounds can be made by one skilled in the art.

TABLE IA

| R$_6$ | n | Z | Q |
|---|---|---|---|
| CH$_3$ | 0 | CH | S |
| CH$_3$ | 2 | CH | S |
| CH$_3$ | 0 | N | S |
| CH$_3$ | 2 | N | S |
| C$_2$H$_5$ | 0 | CH | O |
| C$_2$H$_5$ | 2 | CH | S |
| C$_2$H$_5$ | 0 | N | S |
| C$_2$H$_5$ | 2 | N | S |
| n-C$_3$H$_7$ | 0 | CH | S |
| n-C$_3$H$_7$ | 2 | CH | O |
| n-C$_3$H$_7$ | 0 | N | S |
| n-C$_3$H$_7$ | 2 | N | S |
| i-C$_3$H$_7$ | 0 | CH | S |
| i-C$_3$H$_7$ | 2 | CH | S |
| i-C$_3$H$_7$ | 0 | N | S |
| i-C$_3$H$_7$ | 2 | N | S |
| CH$_2$CH=CH$_2$ | 0 | CH | O |
| CH$_2$CH=CH$_2$ | 2 | CH | S |
| CH$_2$CH=CH$_2$ | 0 | N | S |
| CH$_2$CH=CH$_2$ | 2 | N | S |
| i-C$_4$H$_9$ | 0 | CH | S |
| i-C$_4$H$_9$ | 2 | CH | S |
| i-C$_4$H$_9$ | 0 | N | S |
| i-C$_4$H$_9$ | 2 | N | S |
| n-C$_4$H$_9$ | 0 | CH | S |
| n-C$_4$H$_9$ | 2 | CH | S |
| n-C$_4$H$_9$ | 0 | N | O |
| n-C$_4$H$_9$ | 2 | N | S |
| CH$_2$CH=CHCH$_3$ | 2 | CH | S |
| cyclopentyl | 0 | CH | S |
| cyclopentyl | 2 | CH | S |

TABLE IA-continued

Structure: furan with SO₂NHCNH—(ring with N, Cl, Z, Cl), and S(O)ₙR₆ on furan; Q in furan ring.

| R₆ | n | Z | Q |
|---|---|---|---|
| cyclopentyl | 0 | N | S |
| cyclopentyl | 2 | N | S |
| cyclopropylmethyl | 0 | CH | S |
| cyclopropylmethyl | 2 | CH | S |
| cyclopropylmethyl | 0 | N | S |
| cyclopropylmethyl | 2 | N | S |

TABLE IB

| R₆ | n | Z | Q |
|---|---|---|---|
| CH₃ | 0 | CH | S |
| CH₃ | 2 | CH | O |
| CH₃ | 0 | N | S |
| CH₃ | 2 | N | S |
| C₂H₅ | 0 | CH | S |
| C₂H₅ | 2 | CH | S |
| C₂H₅ | 0 | N | S |
| C₂H₅ | 2 | N | S |
| n-C₃H₇ | 0 | CH | S |
| n-C₃H₇ | 2 | CH | S |
| n-C₃H₇ | 0 | N | S |
| n-C₃H₇ | 2 | N | O |
| i-C₃H₇ | 0 | CH | S |
| i-C₃H₇ | 2 | CH | S |
| i-C₃H₇ | 0 | N | S |
| i-C₃H₇ | 2 | N | S |
| CH₂CH=CH₂ | 0 | CH | S |
| CH₂CH=CH₂ | 2 | CH | S |
| CH₂CH=CH₂ | 0 | N | S |
| CH₂CH=CH₂ | 2 | N | S |
| i-C₄H₉ | 0 | CH | S |
| i-C₄H₉ | 2 | CH | S |
| i-C₄H₉ | 0 | N | S |
| i-C₄H₉ | 2 | N | S |
| n-C₄H₉ | 0 | CH | S |
| n-C₄H₉ | 2 | CH | S |
| n-C₄H₉ | 0 | N | S |
| n-C₄H₉ | 2 | N | S |
| CH₂CH=CHCH₃ | 2 | CH | S |
| cyclopentyl | 0 | CH | S |
| cyclopentyl | 2 | CH | O |
| cyclopentyl | 0 | N | S |
| cyclopentyl | 2 | N | S |
| cyclopropylmethyl | 0 | CH | S |
| cyclopropylmethyl | 2 | CH | S |
| cyclopropylmethyl | 0 | N | S |
| cyclopropylmethyl | 2 | N | S |

TABLE IC

| R₆ | n | Z | Q |
|---|---|---|---|
| CH₃ | 0 | CH | S |
| CH₃ | 2 | CH | S |
| CH₃ | 0 | N | S |
| CH₃ | 2 | N | S |
| C₂H₅ | 0 | CH | S |
| C₂H₅ | 2 | CH | S |
| C₂H₅ | 0 | N | S |
| C₂H₅ | 2 | N | S |
| n-C₃H₇ | 0 | CH | O |
| n-C₃H₇ | 2 | CH | S |
| n-C₃H₇ | 0 | N | S |
| n-C₃H₇ | 2 | N | S |
| i-C₃H₇ | 0 | CH | S |
| i-C₂H₇ | 2 | CH | S |
| i-C₃H₇ | 0 | N | S |
| i-C₃H₇ | 2 | N | S |
| CH₂CH=CH₂ | 0 | CH | S |
| CH₂CH=CH₂ | 2 | CH | O |
| CH₂CH=CH₂ | 0 | N | S |
| CH₂CH=CH₂ | 2 | N | S |
| i-C₄H₉ | 0 | CH | S |
| i-C₄H₉ | 2 | CH | S |
| i-C₄H₉ | 0 | N | S |
| i-C₄H₉ | 2 | N | S |
| n-C₄H₉ | 0 | CH | S |
| n-C₄H₉ | 2 | CH | S |
| n-C₄H₉ | 0 | N | S |
| n-C₄H₉ | 2 | N | S |
| CH₂CH=CHCH₃ | 2 | CH | S |
| cyclopentyl | 0 | CH | O |
| cyclopentyl | 2 | CH | S |
| cyclopentyl | 0 | N | S |
| cyclopentyl | 2 | N | S |
| cyclopropylmethyl | 0 | CH | S |
| cyclopropylmethyl | 2 | CH | S |
| cyclopropylmethyl | 0 | N | S |
| cyclopropylmethyl | 2 | N | S |

TABLE IIA

| R₆ | n | Q |
|---|---|---|
| CH₃ | 0 | S |
| CH₃ | 2 | S |
| C₂H₅ | 0 | S |
| C₂H₅ | 2 | O |
| n-C₃H₇ | 0 | S |
| n-C₃H₇ | 2 | S |
| i-C₃H₇ | 0 | S |
| i-C₃H₇ | 2 | S |
| CH₂CH=CH₂ | 0 | S |
| CH₂CH=CH₂ | 2 | S |
| n-C₄H₉ | 0 | S |
| n-C₄H₉ | 2 | S |
| i-C₄H₉ | 0 | O |
| i-C₄H₉ | 2 | S |
| cyclopentyl | 0 | O |
| cyclopentyl | 2 | S |
| cyclopropylmethyl | 0 | S |
| cyclopropylmethyl | 2 | S |
| CH₂CH=CHCH₃ | 2 | S |

TABLE IIB

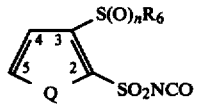

| R₆ | n | Q |
|---|---|---|
| CH₃ | 0 | S |
| CH₃ | 2 | S |
| C₂H₅ | 0 | O |
| C₂H₅ | 2 | S |
| n-C₃H₇ | 0 | S |
| n-C₃H₇ | 2 | S |
| i-C₃H₇ | 0 | S |
| i-C₃H₇ | 2 | S |
| CH₂CH=CH₂ | 0 | S |
| CH₂CH=CH₂ | 2 | S |
| n-C₄H₉ | 0 | O |
| n-C₄H₉ | 2 | S |
| i-C₄H₉ | 0 | S |
| i-C₄H₉ | 2 | S |
| cyclopentyl | 0 | S |
| cyclopentyl | 2 | S |
| cyclopropylmethyl | 0 | S |
| cyclopropylmethyl | 2 | S |
| CH₂CH=CHCH₃ | 2 | S |

TABLE IIC

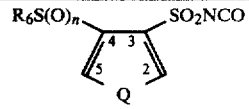

| R₆ | n | Q |
|---|---|---|
| CH₃ | 0 | S |
| CH₃ | 2 | S |
| C₂H₅ | 0 | S |
| C₂H₅ | 2 | O |
| n-C₃H₇ | 0 | S |
| n-C₃H₇ | 2 | S |
| i-C₃H₇ | 0 | S |
| i-C₃H₇ | 2 | S |
| CH₂CH=CH₂ | 0 | S |
| CH₂CH=CH₂ | 2 | S |
| n-C₄H₉ | 0 | S |
| n-C₄H₉ | 2 | S |
| i-C₄H₉ | 0 | S |
| i-C₄H₉ | 2 | S |
| cyclopentyl | 0 | O |
| cyclopentyl | 2 | S |
| cyclopropylmethyl | 0 | S |
| cyclopropymethyl | 2 | S |
| CH₂CH=CHCH₃ | 2 | S |

TABLE IIIA

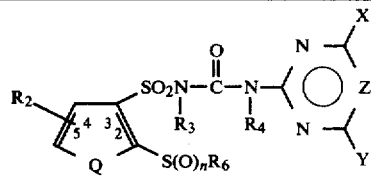

| R₆ | n | R₂ | R₃ | R₄ | X | Y | Z | Q | m.p. (°C.) |
|---|---|---|---|---|---|---|---|---|---|
| CH₃ | 0 | H | H | H | CH₃ | CH₃ | CH | S | 182–184° |
| CH₃ | 0 | H | H | H | CH₃ | OCH₃ | CH | S | 169–176° |
| CH₃ | 0 | H | H | H | OCH₃ | OCH₃ | CH | S | 177–181° d |
| CH₃ | 0 | H | H | H | CH₃ | CH₃ | N | S | |
| CH₃ | 0 | H | H | H | CH₃ | OCH₃ | N | S | |
| CH₃ | 0 | H | H | H | OCH₃ | OCH₃ | N | S | |
| CH₃ | 0 | H | H | CH₃ | CH₃ | CH₃ | CH | S | |
| CH₃ | 0 | H | H | CH₃ | CH₃ | OCH₃ | CH | S | |
| CH₃ | 0 | H | H | CH₃ | OCH₃ | OCH₃ | CH | S | |
| CH₃ | 0 | H | H | CH₃ | CH₃ | CH₃ | N | O | |
| CH₃ | 0 | H | H | CH₃ | CH₃ | OCH₃ | N | S | |
| CH₃ | 0 | H | H | CH₃ | OCH₃ | OCH₃ | N | S | |
| CH₃ | 1 | H | H | H | CH₃ | CH₃ | CH | S | |
| CH₃ | 1 | H | H | H | CH₃ | OCH₃ | CH | S | |
| CH₃ | 1 | H | H | H | OCH₃ | OCH₃ | CH | S | |
| CH₃ | 1 | H | H | H | CH₃ | CH₃ | N | S | |
| CH₃ | 1 | H | H | H | CH₃ | OCH₃ | N | S | |
| CH₃ | 1 | H | H | H | OCH₃ | OCH₃ | N | S | |
| CH₃ | 1 | H | H | CH₃ | CH₃ | CH₃ | CH | O | |
| CH₃ | 1 | H | H | CH₃ | CH₃ | OCH₃ | CH | S | |
| CH₃ | 1 | H | H | CH₃ | OCH₃ | OCH₃ | CH | S | |
| CH₃ | 1 | H | H | CH₃ | CH₃ | CH₃ | N | S | |
| CH₃ | 1 | H | H | CH₃ | CH₃ | OCH₃ | N | S | |
| CH₃ | 1 | H | H | CH₃ | OCH₃ | OCH₃ | N | S | |
| CH₃ | 2 | H | H | CH₃O | CH₃ | CH₃ | CH | S | |
| CH₃ | 2 | H | H | CH₃O | CH₃ | OCH₃ | CH | S | |
| CH₃ | 2 | H | H | CH₃O | CH₃O | CH₃O | CH | S | |
| CH₃ | 2 | H | H | CH₃O | CH₃ | CH₃ | N | S | |
| CH₃ | 2 | H | H | CH₃O | CH₃ | OCH₃ | N | S | |
| CH₃ | 2 | H | H | CH₃O | CH₃O | CH₃O | N | S | |
| CH₃ | 2 | H | H | H | CH₃ | CH₃ | CH | S | 192–194° |
| CH₃ | 2 | H | H | H | CH₃ | OCH₃ | CH | S | 204–206° |
| CH₃ | 2 | H | H | H | OCH₃ | OCH₃ | CH | S | 201–202° |
| CH₃ | 2 | H | H | H | CH₃ | CH₃ | N | S | |
| CH₃ | 2 | H | H | H | CH₃ | OCH₃ | N | S | 202–205° |
| CH₃ | 2 | H | H | H | OCH₃ | OCH₃ | N | S | 205–207° |
| CH₃ | 2 | H | H | CH₃ | CH₃ | CH₃ | CH | S | |
| CH₃ | 2 | H | H | CH₃ | CH₃ | OCH₃ | CH | S | |
| CH₃ | 2 | H | H | CH₃ | OCH₃ | OCH₃ | CH | S | |
| CH₃ | 2 | H | H | CH₃ | CH₃ | CH₃ | N | O | |
| CH₃ | 2 | H | H | CH₃ | CH₃ | OCH₃ | N | S | |

TABLE IIIA-continued

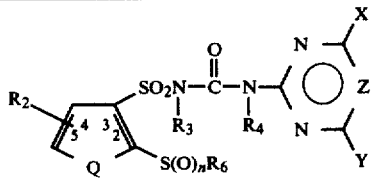

| R6 | n | R2 | R3 | R4 | X | Y | Z | Q | m.p. (°C.) |
|---|---|---|---|---|---|---|---|---|---|
| CH3 | 2 | H | H | CH3 | OCH3 | OCH3 | N | S | |
| C2H5 | 0 | H | H | H | CH3 | CH3 | CH | S | |
| C2H5 | 0 | H | H | H | CH3 | OCH3 | CH | S | |
| C2H5 | 0 | H | H | H | OCH3 | OCH3 | CH | S | |
| C2H5 | 0 | H | H | H | CH3 | CH3 | N | S | |
| C2H5 | 0 | H | H | H | CH3 | CH3 | N | O | |
| C2H5 | 0 | H | H | H | OCH3 | OCH3 | N | S | |
| C2H5 | 0 | H | H | CH3 | CH3 | CH3 | CH | S | |
| C2H5 | 0 | H | H | CH3 | CH3 | OCH3 | CH | S | |
| C2H5 | 0 | H | H | CH3 | OCH3 | OCH3 | CH | S | |
| C2H5 | 0 | H | H | CH3 | CH3 | CH3 | N | S | |
| C2H5 | 0 | H | H | CH3 | CH3 | OCH3 | N | S | |
| C2H5 | 0 | H | H | CH3 | OCH3 | OCH3 | N | O | |
| C2H5 | 1 | H | H | H | CH3 | CH3 | CH | S | |
| C2H5 | 1 | H | H | H | CH3 | OCH3 | CH | S | |
| C2H5 | 1 | H | H | H | OCH3 | OCH3 | CH | S | |
| C2H5 | 1 | H | H | H | CH3 | CH3 | N | S | |
| C2H5 | 1 | H | H | H | CH3 | OCH3 | N | S | |
| C2H5 | 1 | H | H | H | OCH3 | OCH3 | N | S | |
| C2H5 | 1 | H | H | CH3 | CH3 | CH3 | CH | S | |
| C2H5 | 1 | H | H | CH3 | CH3 | OCH3 | CH | S | |
| C2H5 | 1 | H | H | CH3 | OCH3 | OCH3 | CH | S | |
| C2H5 | 1 | H | H | CH3 | CH3 | CH3 | N | O | |
| C2H5 | 1 | H | H | CH3 | CH3 | OCH3 | N | O | |
| C2H5 | 1 | H | H | CH3 | OCH3 | OCH3 | N | O | |
| C2H5 | 2 | H | H | H | CH3 | CH3 | CH | S | |
| C2H5 | 2 | H | H | H | CH3 | OCH3 | CH | S | |
| C2H5 | 2 | H | H | H | OCH3 | OCH3 | CH | S | |
| C2H5 | 2 | H | H | H | CH3 | CH3 | N | S | |
| C2H5 | 2 | H | H | H | CH3 | OCH3 | N | S | |
| C2H5 | 2 | H | H | H | OCH3 | OCH3 | N | S | |
| C2H5 | 2 | H | H | CH3 | CH3 | CH3 | CH | O | |
| C2H5 | 2 | H | H | CH3 | CH3 | OCH3 | CH | S | |
| C2H5 | 2 | H | H | CH3 | OCH3 | OCH3 | CH | S | |
| C2H5 | 2 | H | H | CH3 | CH3 | CH3 | N | S | |
| C2H5 | 2 | H | H | CH3 | CH3 | OCH3 | N | S | |
| C2H5 | 2 | H | H | CH3 | OCH3 | OCH3 | N | S | |
| n-C3H7 | 0 | H | H | H | CH3 | CH3 | CH | O | |
| n-C3H7 | 0 | H | H | H | CH3 | OCH3 | CH | S | |
| n-C3H7 | 0 | H | H | H | OCH3 | OCH3 | CH | S | |
| n-C3H7 | 0 | H | H | H | CH3 | CH3 | N | S | |
| n-C3H7 | 0 | H | H | H | CH3 | OCH3 | N | S | |
| n-C3H7 | 0 | H | H | H | OCH3 | OCH3 | N | S | |
| n-C3H7 | 0 | H | H | CH3 | CH3 | CH3 | CH | S | |
| n-C3H7 | 0 | H | H | CH3 | CH3 | OCH3 | CH | S | |
| n-C3H7 | 0 | H | H | CH3 | OCH3 | OCH3 | CH | S | |
| n-C3H7 | 0 | H | H | CH3 | CH3 | CH3 | N | S | |
| n-C3H7 | 0 | H | H | CH3 | CH3 | OCH3 | N | S | |
| n-C3H7 | 0 | H | H | CH3 | OCH3 | OCH3 | N | S | |
| n-C3H7 | 1 | H | H | H | CH3 | CH3 | CH | S | |
| n-C3H7 | 1 | H | H | H | CH3 | OCH3 | CH | S | |
| n-C3H7 | 1 | H | H | H | OCH3 | OCH3 | CH | S | |
| n-C3H7 | 1 | H | H | H | CH3 | CH3 | N | S | |
| n-C3H7 | 1 | H | H | H | CH3 | OCH3 | N | S | |
| n-C3H7 | 1 | H | H | H | OCH3 | OCH3 | N | S | |
| n-C3H7 | 1 | H | H | CH3 | CH3 | CH3 | CH | S | |
| n-C3H7 | 1 | H | H | CH3 | CH3 | OCH3 | CH | S | |
| n-C3H7 | 1 | H | H | CH3 | OCH3 | OCH3 | CH | S | |
| n-C3H7 | 1 | H | H | CH3 | CH3 | CH3 | N | O | |
| n-C3H7 | 1 | H | H | CH3 | CH3 | OCH3 | N | S | |
| n-C3H7 | 1 | H | H | CH3 | OCH3 | OCH3 | N | S | |
| n-C3H7 | 2 | H | H | H | CH3 | CH3 | CH | S | 127–128° d |
| n-C3H7 | 2 | H | H | H | CH3 | OCH3 | CH | S | 132–140° d |
| n-C3H7 | 2 | H | H | H | OCH3 | OCH3 | CH | S | 134–138° |
| n-C3H7 | 2 | H | H | H | CH3 | CH3 | N | S | |
| n-C3H7 | 2 | H | H | H | CH3 | OCH3 | N | S | 153–156° d |
| n-C3H7 | 2 | H | H | H | OCH3 | OCH3 | N | S | 172–178° d |
| n-C3H7 | 2 | H | H | CH3 | CH3 | CH3 | CH | S | |
| n-C3H7 | 2 | H | H | CH3 | CH3 | OCH3 | CH | S | |
| n-C3H7 | 2 | H | H | CH3 | OCH3 | OCH3 | CH | S | |
| n-C3H7 | 2 | H | H | CH3 | CH3 | CH3 | N | S | |

TABLE IIIA-continued

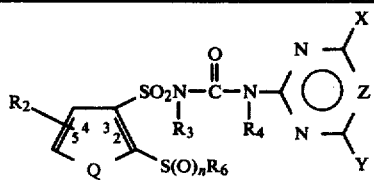

| R6 | n | R2 | R3 | R4 | X | Y | Z | Q | m.p. (°C.) |
|---|---|---|---|---|---|---|---|---|---|
| n-C3H7 | 2 | H | H | CH3 | CH3 | OCH3 | N | S | |
| n-C3H7 | 2 | H | H | CH3 | OCH3 | OCH3 | N | S | |
| i-C3H7 | 0 | H | H | H | CH3 | CH3 | CH | O | |
| i-C3H7 | 0 | H | H | H | CH3 | CH3 | CH | S | |
| i-C3H7 | 0 | H | H | H | OCH3 | OCH3 | CH | S | |
| i-C3H7 | 0 | H | H | H | CH3 | CH3 | N | S | |
| i-C3H7 | 0 | H | H | H | CH3 | OCH3 | N | S | |
| i-C3H7 | 0 | H | H | H | OCH3 | OCH3 | N | S | |
| i-C3H7 | 0 | H | H | CH3 | CH3 | CH3 | CH | S | |
| i-C3H7 | 0 | H | H | CH3 | CH3 | OCH3 | CH | S | |
| i-C3H7 | 0 | H | H | CH3 | OCH3 | OCH3 | CH | O | |
| i-C3H7 | 0 | H | H | CH3 | CH3 | CH3 | N | O | |
| i-C3H7 | 0 | H | H | CH3 | CH3 | OCH3 | N | O | |
| i-C3H7 | 0 | H | H | CH3 | OCH3 | OCH3 | N | O | |
| i-C3H7 | 1 | H | H | H | CH3 | CH3 | CH | S | |
| i-C3H7 | 1 | H | H | H | CH3 | OCH3 | CH | S | |
| i-C3H7 | 1 | H | H | H | OCH3 | OCH3 | CH | S | |
| i-C3H7 | 1 | H | H | H | CH3 | CH3 | N | S | |
| i-C3H7 | 1 | H | H | H | CH3 | OCH3 | N | S | |
| i-C3H7 | 1 | H | H | H | OCH3 | OCH3 | N | S | |
| i-C3H7 | 1 | H | H | CH3 | CH3 | CH3 | CH | S | |
| i-C3H7 | 1 | H | H | CH3 | CH3 | OCH3 | CH | S | |
| i-C3H7 | 1 | H | H | CH3 | OCH3 | OCH3 | CH | S | |
| i-C3H7 | 1 | H | H | CH3 | CH3 | CH3 | N | O | |
| i-C3H7 | 1 | H | H | CH3 | CH3 | OCH3 | N | S | |
| i-C3H7 | 1 | H | H | CH3 | OCH3 | OCH3 | N | S | |
| i-C3H7 | 2 | H | H | H | CH3 | CH3 | CH | S | |
| i-C3H7 | 2 | H | H | H | CH3 | OCH3 | CH | S | |
| i-C3H7 | 2 | H | H | H | OCH3 | OCH3 | CH | S | |
| i-C3H7 | 2 | H | H | H | CH3 | CH3 | N | S | |
| i-C3H7 | 2 | H | H | H | CH3 | OCH3 | N | S | |
| i-C3H7 | 2 | H | H | H | OCH3 | OCH3 | N | S | |
| i-C3H7 | 2 | H | H | CH3 | CH3 | CH3 | CH | O | |
| i-C3H7 | 2 | H | H | CH3 | CH3 | CH3 | CH | S | |
| i-C3H7 | 2 | H | H | CH3 | CH3 | OCH3 | CH | S | |
| i-C3H7 | 2 | H | H | CH3 | OCH3 | OCH3 | CH | S | |
| i-C3H7 | 2 | H | H | CH3 | CH3 | CH3 | N | S | |
| i-C3H7 | 2 | H | H | CH3 | CH3 | OCH3 | N | S | |
| i-C3H7 | 2 | H | H | CH3 | OCH3 | OCH3 | N | S | |
| CH2CH=CH2 | 2 | H | H | H | CH3 | CH3 | CH | S | |
| CH2CH=CH2 | 2 | H | H | H | CH3 | OCH3 | CH | S | |
| CH2CH=CH2 | 2 | H | H | H | OCH3 | OCH3 | CH | S | |
| CH2CH=CH2 | 2 | H | H | H | CH3 | CH3 | N | S | |
| CH2CH=CH2 | 2 | H | H | H | CH3 | OCH3 | N | S | |
| CH2CH=CH2 | 2 | H | H | H | OCH3 | OCH3 | N | S | |
| CH2CH=CH2 | 2 | H | H | CH3 | CH3 | CH3 | CH | S | |
| CH2CH=CH2 | 2 | H | H | CH3 | CH3 | OCH3 | CH | S | |
| CH2CH=CH2 | 2 | H | H | CH3 | OCH3 | OCH3 | CH | S | |
| CH2CH=CH2 | 2 | H | H | CH3 | CH3 | CH3 | N | S | |
| CH2CH=CH2 | 2 | H | H | CH3 | CH3 | OCH3 | N | S | |
| CH2CH=CH2 | 2 | H | H | CH3 | OCH3 | OCH3 | N | S | |
| cyclopentyl | 2 | H | H | H | CH3 | CH3 | CH | O | |
| cyclopentyl | 2 | H | H | H | CH3 | CH3 | CH | S | |
| cyclopentyl | 2 | H | H | H | OCH3 | OCH3 | CH | S | |
| cyclopentyl | 2 | H | H | H | CH3 | CH3 | N | S | |
| cyclopentyl | 2 | H | H | H | CH3 | OCH3 | N | S | |
| cyclopentyl | 2 | H | H | H | OCH3 | OCH3 | N | S | |
| cyclopentyl | 2 | H | H | CH3 | CH3 | CH3 | CH | S | |
| cyclopentyl | 2 | H | H | CH3 | CH3 | OCH3 | CH | S | |
| cyclopentyl | 2 | H | H | CH3 | OCH3 | OCH3 | CH | S | |
| cyclopentyl | 2 | H | H | CH3 | CH3 | CH3 | N | S | |
| cyclopentyl | 2 | H | H | CH3 | CH3 | OCH3 | N | S | |
| cyclopentyl | 2 | H | H | CH3 | OCH3 | OCH3 | N | S | |
| cyclopropylmethyl | 2 | H | H | H | CH3 | CH3 | CH | S | |
| cyclopropylmethyl | 2 | H | H | H | CH3 | OCH3 | CH | S | |
| cyclopropylmethyl | 2 | H | H | H | OCH3 | OCH3 | CH | S | |
| cyclopropylmethyl | 2 | H | H | H | CH3 | CH3 | N | S | |
| cyclopropylmethyl | 2 | H | H | H | CH3 | OCH3 | N | S | |
| cyclopropylmethyl | 2 | H | H | H | OCH3 | OCH3 | N | S | |
| cyclopropylmethyl | 2 | H | H | CH3 | CH3 | CH3 | CH | S | |
| cyclopropylmethyl | 2 | H | H | CH3 | CH3 | OCH3 | CH | S | |
| cyclopropylmethyl | 2 | H | H | CH3 | OCH3 | OCH3 | CH | S | |

TABLE IIIA-continued

[Structure diagram with R2, positions 5,4,3,2, Q ring, S(O)nR6, SO2N(R3)-C(=O)-N(R4)- linked to pyrimidine/triazine ring with X, Y, Z]

| R6 | n | R2 | R3 | R4 | X | Y | Z | Q | m.p. (°C.) |
|---|---|---|---|---|---|---|---|---|---|
| cyclopropylmethyl | 2 | H | H | CH3 | CH3 | CH3 | N | S | |
| cyclopropylmethyl | 2 | H | H | CH3 | CH3 | OCH3 | N | S | |
| cyclopropylmethyl | 2 | H | H | CH3 | OCH3 | OCH3 | N | S | |
| n-C4H9 | 2 | H | H | H | CH3 | CH3 | CH | S | |
| n-C4H9 | 2 | H | H | H | CH3 | OCH3 | CH | O | |
| n-C4H9 | 2 | H | H | H | OCH3 | OCH3 | CH | S | |
| n-C4H9 | 2 | H | H | H | CH3 | CH3 | N | S | |
| n-C4H9 | 2 | H | H | H | CH3 | OCH3 | N | S | |
| n-C4H9 | 2 | H | H | H | OCH3 | OCH3 | N | S | |
| n-C4H9 | 2 | H | H | CH3 | CH3 | CH3 | CH | S | |
| n-C4H9 | 2 | H | H | CH3 | CH3 | OCH3 | CH | S | |
| n-C4H9 | 2 | H | H | CH3 | OCH3 | OCH3 | CH | S | |
| n-C4H9 | 2 | H | H | CH3 | CH3 | CH3 | N | S | |
| n-C4H9 | 2 | H | H | CH3 | CH3 | OCH3 | N | S | |
| n-C4H9 | 2 | H | H | CH3 | OCH3 | OCH3 | N | S | |
| CH3 | 2 | H | CH3 | H | CH3 | OCH3 | N | S | |
| C2H5 | 2 | H | CH3 | H | OCH3 | OCH3 | CH | S | |
| n-C3H7 | 2 | H | CH3 | H | OCH3 | OCH3 | N | S | |
| i-C3H7 | 2 | H | CH3 | H | CH3 | CH3 | CH | O | |
| CH2CH=CH2 | 2 | H | CH3 | H | OCH3 | OCH3 | N | S | |
| cyclopentyl | 2 | H | CH3 | H | OCH3 | OCH3 | CH | S | |
| cyclopropylmethyl | 2 | H | CH3 | H | CH3 | OCH3 | N | S | |
| CH3 | 0 | 4-Cl | H | H | CH3 | OCH3 | CH | S | |
| C2H5 | 2 | 5-CH3 | H | H | OCH3 | OCH3 | CH | S | |
| n-C3H7 | 2 | 4-Br | H | H | CH3 | OCH3 | N | S | |
| CH3 | 2 | H | H | H | CH3 | OC2H5 | CH | S | |
| C2H5 | 1 | H | H | H | OCH3 | C2H5 | N | S | |
| CH3 | 2 | H | H | H | OCH3 | CH2OCH3 | N | S | |
| CH3 | 2 | H | H | H | OCH3 | Cl | N | S | |
| CH3 | 2 | H | H | H | OCH3 | H | CH | S | |
| t-C4H9 | 0 | H | H | H | CH3 | OCH3 | N | S | |
| CH2CH=CHCH3 | 2 | H | H | H | OCH3 | OCH3 | CH | S | |
| i-C4H9 | 2 | H | H | H | CH3 | OCH3 | N | S | |
| s-C4H9 | 2 | H | H | H | OCH3 | OCH3 | CH | S | |

TABLE IIIB

[Structure diagram with R2, S(O)nR6 at position 3, SO2N(R3)-C(=O)-N(R4)- linked to heterocycle with X, Y, Z]

| R6 | n | R2 | R3 | R4 | X | Y | Z | Q | m.p. (°C.) |
|---|---|---|---|---|---|---|---|---|---|
| CH3 | 0 | H | H | H | CH3 | CH3 | CH | S | 187–188° |
| CH3 | 0 | H | H | H | CH3 | OCH3 | CH | S | 174–176° |
| CH3 | 0 | H | H | H | OCH3 | OCH3 | CH | S | 172–178° |
| CH3 | 0 | H | H | H | CH3 | CH3 | N | S | |
| CH3 | 0 | H | H | H | CH3 | OCH3 | N | S | 137° d |
| CH3 | 0 | H | H | H | OCH3 | OCH3 | N | S | 162–167° |
| CH3 | 0 | H | H | CH3 | CH3 | CH3 | CH | S | |
| CH3 | 0 | H | H | CH3 | CH3 | OCH3 | CH | S | |
| CH3 | 0 | H | H | CH3 | OCH3 | OCH3 | CH | S | |
| CH3 | 0 | H | H | CH3 | CH3 | CH3 | N | S | |
| CH3 | 0 | H | H | CH3 | CH3 | OCH3 | N | S | |
| CH3 | 0 | H | H | CH3 | OCH3 | OCH3 | N | S | |
| CH3 | 1 | H | H | H | CH3 | CH3 | CH | S | |
| CH3 | 1 | H | H | H | CH3 | OCH3 | CH | S | |
| CH3 | 1 | H | H | H | OCH3 | OCH3 | CH | S | |
| CH3 | 1 | H | H | H | CH3 | CH3 | N | O | |
| CH3 | 1 | H | H | H | CH3 | OCH3 | N | S | |
| CH3 | 1 | H | H | H | OCH3 | OCH3 | N | S | |
| CH3 | 1 | H | H | CH3 | CH3 | CH3 | CH | S | |
| CH3 | 1 | H | H | CH3 | CH3 | OCH3 | CH | S | |
| CH3 | 1 | H | H | CH3 | OCH3 | OCH3 | CH | S | |
| CH3 | 1 | H | H | CH3 | CH3 | CH3 | N | S | |
| CH3 | 1 | H | H | CH3 | CH3 | OCH3 | N | S | |

TABLE IIIB-continued

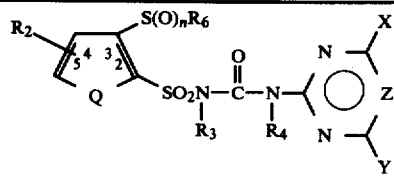

| R6 | n | R2 | R3 | R4 | X | Y | Z | Q | m.p. (°C.) |
|---|---|---|---|---|---|---|---|---|---|
| CH3 | 1 | H | H | CH3 | OCH3 | OCH3 | N | S | |
| CH3 | 2 | H | H | CH3O | CH3 | CH3 | CH | S | |
| CH3 | 2 | H | H | CH3O | CH3 | CH3O | CH | O | |
| CH3 | 2 | H | H | CH3O | CH3O | CH3O | CH | S | |
| CH3 | 2 | H | H | CH3O | CH3 | CH3 | N | S | |
| CH3 | 2 | H | H | CH3O | CH3O | CH3 | N | S | |
| CH3 | 2 | H | H | CH3O | CH3O | CH3O | N | S | |
| CH3 | 2 | H | H | H | CH3 | CH3 | CH | S | 195–197° |
| CH3 | 2 | H | H | H | CH3 | OCH3 | CH | S | 189–195° |
| CH3 | 2 | H | H | H | OCH3 | OCH3 | CH | S | 183–212° |
| CH3 | 2 | H | H | H | CH3 | CH3 | N | S | |
| CH3 | 2 | H | H | H | CH3 | OCH3 | N | S | 167–171° |
| CH3 | 2 | H | H | H | OCH3 | OCH3 | N | S | 186–189° d |
| CH3 | 2 | H | H | CH3 | CH3 | CH3 | CH | O | |
| CH3 | 2 | H | H | CH3 | CH3 | OCH3 | CH | O | |
| CH3 | 2 | H | H | CH3 | OCH3 | OCH3 | CH | O | |
| CH3 | 2 | H | H | CH3 | CH3 | CH3 | N | S | |
| CH3 | 2 | H | H | CH3 | CH3 | OCH3 | N | S | |
| CH3 | 2 | H | H | CH3 | OCH3 | OCH3 | N | S | |
| C2H5 | 0 | H | H | H | CH3 | CH3 | CH | S | |
| C2H5 | 0 | H | H | H | CH3 | OCH3 | CH | S | |
| C2H5 | 0 | H | H | H | OCH3 | OCH3 | CH | S | |
| C2H5 | 0 | H | H | H | CH3 | CH3 | N | S | |
| C2H5 | 0 | H | H | H | CH3 | OCH3 | N | S | |
| C2H5 | 0 | H | H | H | OCH3 | OCH3 | N | S | |
| C2H5 | 0 | H | H | CH3 | CH3 | CH3 | CH | S | |
| C2H5 | 0 | H | H | CH3 | CH3 | OCH3 | CH | S | |
| C2H5 | 0 | H | H | CH3 | OCH3 | OCH3 | CH | S | |
| C2H5 | 0 | H | H | CH3 | CH3 | CH3 | N | S | |
| C2H5 | 0 | H | H | CH3 | CH3 | OCH3 | N | S | |
| C2H5 | 0 | H | H | CH3 | OCH3 | OCH3 | N | S | |
| C2H5 | 1 | H | H | H | CH3 | CH3 | CH | S | |
| C2H5 | 1 | H | H | H | CH3 | OCH3 | CH | S | |
| C2H5 | 1 | H | H | H | OCH3 | OCH3 | CH | S | |
| C2H5 | 1 | H | H | H | CH3 | CH3 | N | S | |
| C2H5 | 1 | H | H | H | CH3 | OCH3 | N | S | |
| C2H5 | 1 | H | H | H | OCH3 | OCH3 | N | S | |
| C2H5 | 1 | H | H | CH3 | CH3 | CH3 | CH | O | |
| C2H5 | 1 | H | H | CH3 | CH3 | OCH3 | CH | O | |
| C2H5 | 1 | H | H | CH3 | OCH3 | OCH3 | CH | O | |
| C2H5 | 1 | H | H | CH3 | CH3 | CH3 | N | S | |
| C2H5 | 1 | H | H | CH3 | CH3 | OCH3 | N | S | |
| C2H5 | 1 | H | H | CH3 | OCH3 | OCH3 | N | S | |
| C2H5 | 2 | H | H | H | CH3 | CH3 | CH | S | |
| C2H5 | 2 | H | H | H | CH3 | OCH3 | CH | S | |
| C2H5 | 2 | H | H | H | OCH3 | OCH3 | CH | S | |
| C2H5 | 2 | H | H | H | CH3 | CH3 | N | S | |
| C2H5 | 2 | H | H | H | CH3 | OCH3 | N | S | |
| C2H5 | 2 | H | H | H | OCH3 | OCH3 | N | S | |
| C2H5 | 2 | H | H | CH3 | CH3 | CH3 | CH | S | |
| C2H5 | 2 | H | H | CH3 | CH3 | OCH3 | CH | S | |
| C2H5 | 2 | H | H | CH3 | OCH3 | OCH3 | CH | S | |
| C2H5 | 2 | H | H | CH3 | CH3 | CH3 | N | S | |
| C2H5 | 2 | H | H | CH3 | CH3 | OCH3 | N | S | |
| C2H5 | 2 | H | H | CH3 | OCH3 | OCH3 | N | S | |
| n-C3H7 | 0 | H | H | H | CH3 | CH3 | CH | S | |
| n-C3H7 | 0 | H | H | H | CH3 | OCH3 | CH | S | |
| n-C3H7 | 0 | H | H | H | OCH3 | OCH3 | CH | S | |
| n-C3H7 | 0 | H | H | H | CH3 | CH3 | N | S | |
| n-C3H7 | 0 | H | H | H | CH3 | OCH3 | N | S | |
| n-C3H7 | 0 | H | H | H | OCH3 | OCH3 | N | S | |
| n-C3H7 | 0 | H | H | CH3 | CH3 | CH3 | CH | S | |
| n-C3H7 | 0 | H | H | CH3 | CH3 | OCH3 | CH | S | |
| n-C3H7 | 0 | H | H | CH3 | OCH3 | OCH3 | CH | S | |
| n-C3H7 | 0 | H | H | CH3 | CH3 | CH3 | N | O | |
| n-C3H7 | 0 | H | H | CH3 | CH3 | OCH3 | N | S | |
| n-C3H7 | 0 | H | H | CH3 | OCH3 | OCH3 | N | S | |
| n-C3H7 | 1 | H | H | H | CH3 | CH3 | CH | S | |
| n-C3H7 | 1 | H | H | H | CH3 | OCH3 | CH | S | |
| n-C3H7 | 1 | H | H | H | OCH3 | OCH3 | CH | S | |
| n-C3H7 | 1 | H | H | H | CH3 | CH3 | N | S | |
| n-C3H7 | 1 | H | H | H | CH3 | OCH3 | N | S | |

TABLE IIIB-continued

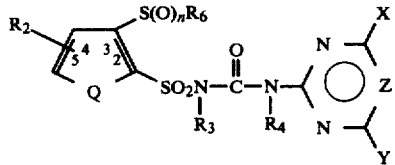

| $R_6$ | n | $R_2$ | $R_3$ | $R_4$ | X | Y | Z | Q | m.p. (°C.) |
|---|---|---|---|---|---|---|---|---|---|
| n-$C_3H_7$ | 1 | H | H | H | $OCH_3$ | $OCH_3$ | N | S | |
| n-$C_3H_7$ | 1 | H | H | $CH_3$ | $CH_3$ | $CH_3$ | CH | S | |
| n-$C_3H_7$ | 1 | H | H | $CH_3$ | $CH_3$ | $OCH_3$ | CH | S | |
| n-$C_3H_7$ | 1 | H | H | $CH_3$ | $OCH_3$ | $OCH_3$ | CH | S | |
| n-$C_3H_7$ | 1 | H | H | $CH_3$ | $CH_3$ | $CH_3$ | N | O | |
| n-$C_3H_7$ | 1 | H | H | $CH_3$ | $CH_3$ | $OCH_3$ | N | O | |
| n-$C_3H_7$ | 1 | H | H | $CH_3$ | $OCH_3$ | $OCH_3$ | N | O | |
| n-$C_3H_7$ | 2 | H | H | H | $CH_3$ | $CH_3$ | CH | S | 175–179° d |
| n-$C_3H_7$ | 2 | H | H | H | $CH_3$ | $OCH_3$ | CH | S | 179–185° d |
| n-$C_3H_7$ | 2 | H | H | H | $OCH_3$ | $OCH_3$ | CH | S | 195–201° d |
| n-$C_3H_7$ | 2 | H | H | H | $CH_3$ | $CH_3$ | N | S | |
| n-$C_3H_7$ | 2 | H | H | H | $CH_3$ | $OCH_3$ | N | S | 162–168° d |
| n-$C_3H_7$ | 2 | H | H | H | $OCH_3$ | $OCH_3$ | N | S | 172–176° d |
| n-$C_3H_7$ | 2 | H | H | $CH_3$ | $CH_3$ | $CH_3$ | CH | O | |
| n-$C_3H_7$ | 2 | H | H | $CH_3$ | $CH_3$ | $OCH_3$ | CH | S | |
| n-$C_3H_7$ | 2 | H | H | $CH_3$ | $OCH_3$ | $OCH_3$ | CH | S | |
| n-$C_3H_7$ | 2 | H | H | $CH_3$ | $CH_3$ | $CH_3$ | N | S | |
| n-$C_3H_7$ | 2 | H | H | $CH_3$ | $CH_3$ | $OCH_3$ | N | S | |
| n-$C_3H_7$ | 2 | H | H | $CH_3$ | $OCH_3$ | $OCH_3$ | N | S | |
| i-$C_3H_7$ | 0 | H | H | H | $CH_3$ | $CH_3$ | CH | O | |
| i-$C_3H_7$ | 0 | H | H | H | $CH_3$ | $OCH_3$ | CH | O | |
| i-$C_3H_7$ | 0 | H | H | H | $OCH_3$ | $OCH_3$ | CH | O | |
| i-$C_3H_7$ | 0 | H | H | H | $CH_3$ | $CH_3$ | N | S | |
| i-$C_3H_7$ | 0 | H | H | H | $CH_3$ | $OCH_3$ | N | S | |
| i-$C_3H_7$ | 0 | H | H | H | $OCH_3$ | $OCH_3$ | N | S | |
| i-$C_3H_7$ | 0 | H | H | $CH_3$ | $CH_3$ | $CH_3$ | CH | S | |
| i-$C_3H_7$ | 0 | H | H | $CH_3$ | $CH_3$ | $OCH_3$ | CH | S | |
| i-$C_3H_7$ | 0 | H | H | $CH_3$ | $OCH_3$ | $OCH_3$ | CH | S | |
| i-$C_3H_7$ | 0 | H | H | $CH_3$ | $CH_3$ | $CH_3$ | N | S | |
| i-$C_3H_7$ | 0 | H | H | $CH_3$ | $CH_3$ | $OCH_3$ | N | S | |
| i-$C_3H_7$ | 0 | H | H | $CH_3$ | $OCH_3$ | $OCH_3$ | N | S | |
| i-$C_3H_7$ | 1 | H | H | H | $CH_3$ | $CH_3$ | CH | O | |
| i-$C_3H_7$ | 1 | H | H | H | $CH_3$ | $OCH_3$ | CH | O | |
| i-$C_3H_7$ | 1 | H | H | H | $OCH_3$ | $OCH_3$ | CH | O | |
| i-$C_3H_7$ | 1 | H | H | H | $CH_3$ | $CH_3$ | N | S | |
| i-$C_3H_7$ | 1 | H | H | H | $CH_3$ | $OCH_3$ | N | S | |
| i-$C_3H_7$ | 1 | H | H | H | $OCH_3$ | $OCH_3$ | N | S | |
| i-$C_3H_7$ | 1 | H | H | $CH_3$ | $CH_3$ | $CH_3$ | CH | S | |
| i-$C_3H_7$ | 1 | H | H | $CH_3$ | $CH_3$ | $OCH_3$ | CH | S | |
| i-$C_3H_7$ | 1 | H | H | $CH_3$ | $OCH_3$ | $OCH_3$ | CH | S | |
| i-$C_3H_7$ | 1 | H | H | $CH_3$ | $CH_3$ | $CH_3$ | N | S | |
| i-$C_3H_7$ | 1 | H | H | $CH_3$ | $CH_3$ | $OCH_3$ | N | S | |
| i-$C_3H_7$ | 1 | H | H | $CH_3$ | $OCH_3$ | $OCH_3$ | N | S | |
| i-$C_3H_7$ | 2 | H | H | H | $CH_3$ | $CH_3$ | CH | S | |
| i-$C_3H_7$ | 2 | H | H | H | $CH_3$ | $OCH_3$ | CH | S | |
| i-$C_3H_7$ | 2 | H | H | H | $OCH_3$ | $OCH_3$ | CH | S | |
| i-$C_3H_7$ | 2 | H | H | H | $CH_3$ | $CH_3$ | N | O | |
| i-$C_3H_7$ | 2 | H | H | H | $CH_3$ | $OCH_3$ | N | O | |
| i-$C_3H_7$ | 2 | H | H | H | $OCH_3$ | $OCH_3$ | N | O | |
| i-$C_3H_7$ | 2 | H | H | $CH_3$ | $CH_3$ | $CH_3$ | CH | S | |
| i-$C_3H_7$ | 2 | H | H | $CH_3$ | $CH_3$ | $OCH_3$ | CH | S | |
| i-$C_3H_7$ | 2 | H | H | $CH_3$ | $OCH_3$ | $OCH_3$ | CH | S | |
| i-$C_3H_7$ | 2 | H | H | $CH_3$ | $CH_3$ | $CH_3$ | N | S | |
| i-$C_3H_7$ | 2 | H | H | $CH_3$ | $CH_3$ | $OCH_3$ | N | S | |
| i-$C_3H_7$ | 2 | H | H | $CH_3$ | $OCH_3$ | $OCH_3$ | N | S | |
| $CH_2CH=CH_2$ | 2 | H | H | H | $CH_3$ | $CH_3$ | CH | S | |
| $CH_2CH=CH_2$ | 2 | H | H | H | $CH_3$ | $OCH_3$ | CH | S | |
| $CH_2CH=CH_2$ | 2 | H | H | H | $OCH_3$ | $OCH_3$ | CH | S | |
| $CH_2CH=CH_2$ | 2 | H | H | H | $CH_3$ | $CH_3$ | N | S | |
| $CH_2CH=CH_2$ | 2 | H | H | H | $CH_3$ | $OCH_3$ | N | S | |
| $CH_2CH=CH_2$ | 2 | H | H | H | $OCH_3$ | $OCH_3$ | N | S | |
| $CH_2CH=CH_2$ | 2 | H | H | $CH_3$ | $CH_3$ | $CH_3$ | CH | S | |
| $CH_2CH=CH_2$ | 2 | H | H | $CH_3$ | $CH_3$ | $OCH_3$ | CH | S | |
| $CH_2CH=CH_2$ | 2 | H | H | $CH_3$ | $OCH_3$ | $OCH_3$ | CH | S | |
| $CH_2CH=CH_2$ | 2 | H | H | $CH_3$ | $CH_3$ | $CH_3$ | N | S | |
| $CH_2CH=CH_2$ | 2 | H | H | $CH_3$ | $CH_3$ | $OCH_3$ | N | S | |
| $CH_2CH=CH_2$ | 2 | H | H | $CH_3$ | $OCH_3$ | $OCH_3$ | N | S | |
| cyclopentyl | 2 | H | H | H | $CH_3$ | $CH_3$ | CH | S | |
| cyclopentyl | 2 | H | H | H | $CH_3$ | $OCH_3$ | CH | S | |
| cyclopentyl | 2 | H | H | H | $OCH_3$ | $OCH_3$ | CH | S | |
| cyclopentyl | 2 | H | H | H | $CH_3$ | $CH_3$ | N | O | |
| cyclopentyl | 2 | H | H | H | $CH_3$ | $OCH_3$ | N | O | |

TABLE IIIB-continued

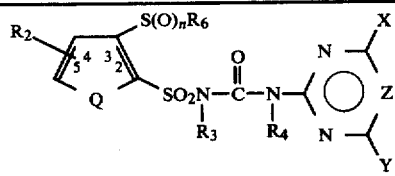

| R<sub>6</sub> | n | R$_2$ | R$_3$ | R$_4$ | X | Y | Z | Q | m.p. (°C.) |
|---|---|---|---|---|---|---|---|---|---|
| cyclopentyl | 2 | H | H | H | OCH$_3$ | OCH$_3$ | N | O | |
| cyclopentyl | 2 | H | H | CH$_3$ | CH$_3$ | CH$_3$ | CH | S | |
| cyclopentyl | 2 | H | H | CH$_3$ | CH$_3$ | OCH$_3$ | CH | S | |
| cyclopentyl | 2 | H | H | CH$_3$ | OCH$_3$ | OCH$_3$ | CH | S | |
| cyclopentyl | 2 | H | H | CH$_3$ | CH$_3$ | CH$_3$ | N | S | |
| cyclopentyl | 2 | H | H | CH$_3$ | CH$_3$ | OCH$_3$ | N | S | |
| cyclopentyl | 2 | H | H | CH$_3$ | OCH$_3$ | OCH$_3$ | N | S | |
| cyclopropylmethyl | 2 | H | H | H | CH$_3$ | CH$_3$ | CH | S | |
| cyclopropylmethyl | 2 | H | H | H | CH$_3$ | OCH$_3$ | CH | S | |
| cyclopropylmethyl | 2 | H | H | H | OCH$_3$ | OCH$_3$ | CH | S | |
| cyclopropylmethyl | 2 | H | H | H | CH$_3$ | CH$_3$ | N | S | |
| cyclopropylmethyl | 2 | H | H | H | CH$_3$ | OCH$_3$ | N | S | |
| cyclopropylmethyl | 2 | H | H | H | OCH$_3$ | OCH$_3$ | N | S | |
| cyclopropylmethyl | 2 | H | H | CH$_3$ | CH$_3$ | CH$_3$ | CH | S | |
| cyclopropylmethyl | 2 | H | H | CH$_3$ | CH$_3$ | OCH$_3$ | CH | S | |
| cyclopropylmethyl | 2 | H | H | CH$_3$ | OCH$_3$ | OCH$_3$ | CH | S | |
| cyclopropylmethyl | 2 | H | H | CH$_3$ | CH$_3$ | CH$_3$ | N | S | |
| cyclopropylmethyl | 2 | H | H | CH$_3$ | CH$_3$ | OCH$_3$ | N | S | |
| cyclopropylmethyl | 2 | H | H | CH$_3$ | OCH$_3$ | OCH$_3$ | N | S | |
| n-C$_4$H$_9$ | 2 | H | H | H | CH$_3$ | CH$_3$ | CH | S | |
| n-C$_4$H$_9$ | 2 | H | H | H | CH$_3$ | OCH$_3$ | CH | S | |
| n-C$_4$H$_9$ | 2 | H | H | H | OCH$_3$ | OCH$_3$ | CH | S | |
| n-C$_4$H$_9$ | 2 | H | H | H | CH$_3$ | CH$_3$ | N | S | |
| n-C$_4$H$_9$ | 2 | H | H | H | CH$_3$ | OCH$_3$ | N | S | |
| n-C$_4$H$_9$ | 2 | H | H | H | OCH$_3$ | OCH$_3$ | N | S | |
| n-C$_4$H$_9$ | 2 | H | H | CH$_3$ | CH$_3$ | CH$_3$ | CH | S | |
| n-C$_4$H$_9$ | 2 | H | H | CH$_3$ | CH$_3$ | OCH$_3$ | CH | S | |
| n-C$_4$H$_9$ | 2 | H | H | CH$_3$ | OCH$_3$ | OCH$_3$ | CH | S | |
| n-C$_4$H$_9$ | 2 | H | H | CH$_3$ | CH$_3$ | CH$_3$ | N | S | |
| n-C$_4$H$_9$ | 2 | H | H | CH$_3$ | CH$_3$ | OCH$_3$ | N | S | |
| n-C$_4$H$_9$ | 2 | H | H | CH$_3$ | OCH$_3$ | OCH$_3$ | N | S | |
| CH$_3$ | 2 | H | CH$_3$ | H | CH$_3$ | OCH$_3$ | N | S | |
| C$_2$H$_5$ | 2 | H | CH$_3$ | H | OCH$_3$ | OCH$_3$ | CH | S | |
| n-C$_3$H$_7$ | 2 | H | CH$_3$ | H | OCH$_3$ | OCH$_3$ | N | O | |
| i-C$_3$H$_7$ | 2 | H | CH$_3$ | H | CH$_3$ | CH$_3$ | CH | S | |
| CH$_2$CH=CH$_2$ | 2 | H | CH$_3$ | H | OCH$_3$ | OCH$_3$ | N | S | |
| cyclopentyl | 2 | H | CH$_3$ | H | CH$_3$ | OCH$_3$ | CH | S | |
| cyclopropylmethyl | 2 | H | CH$_3$ | H | CH$_3$ | OCH$_3$ | N | S | |
| CH$_3$ | 0 | 4-Cl | H | H | CH$_3$ | OCH$_3$ | CH | S | |
| C$_2$H$_5$ | 2 | 5-CH$_3$ | H | H | OCH$_3$ | OCH$_3$ | CH | S | |
| n-C$_3$H$_7$ | 2 | 5-Br | H | H | CH$_3$ | OCH$_3$ | N | S | |
| CH$_3$ | 2 | H | H | H | CH$_3$ | OC$_2$H$_5$ | CH | S | |
| C$_2$H$_5$ | 1 | H | H | H | OCH$_3$ | C$_2$H$_5$ | N | S | |
| CH$_3$ | 2 | H | H | H | OCH$_3$ | CH$_2$OCH$_3$ | N | O | |
| CH$_3$ | 2 | H | H | H | OCH$_3$ | Cl | N | S | |
| CH$_3$ | 2 | H | H | H | OCH$_3$ | H | CH | S | |
| t-C$_4$H$_9$ | 0 | H | H | H | CH$_3$ | OCH$_3$ | N | S | |
| CH$_2$CH=CHCH$_3$ | 2 | H | H | H | OCH$_3$ | OCH$_3$ | CH | S | |
| i-C$_4$H$_9$ | 2 | H | H | H | CH$_3$ | OCH$_3$ | N | S | |
| s-C$_4$H$_9$ | 2 | H | H | H | OCH$_3$ | OCH$_3$ | CH | S | |

TABLE IIIC

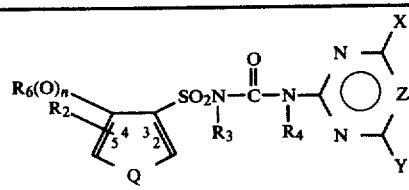

| R$_6$ | n | R$_2$ | R$_3$ | R$_4$ | X | Y | Z | Q | m.p. (°C.) |
|---|---|---|---|---|---|---|---|---|---|
| CH$_3$ | 0 | H | H | H | CH$_3$ | CH$_3$ | CH | S | |
| CH$_3$ | 0 | H | H | H | CH$_3$ | OCH$_3$ | CH | S | |
| CH$_3$ | 0 | H | H | H | OCH$_3$ | OCH$_3$ | CH | S | |
| CH$_3$ | 0 | H | H | H | CH$_3$ | CH$_3$ | N | S | |
| CH$_3$ | 0 | H | H | H | CH$_3$ | OCH$_3$ | N | S | |
| CH$_3$ | 0 | H | H | H | OCH$_3$ | OCH$_3$ | N | S | |
| CH$_3$ | 0 | H | H | CH$_3$ | CH$_3$ | CH$_3$ | CH | S | |

TABLE IIIC-continued

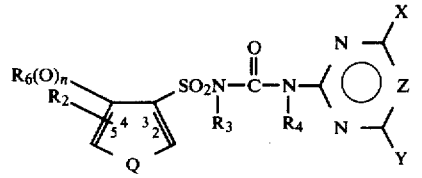

| R6 | n | R2 | R3 | R4 | X | Y | Z | Q | m.p. (°C.) |
|---|---|---|---|---|---|---|---|---|---|
| CH3 | 0 | H | H | CH3 | CH3 | OCH3 | CH | S | |
| CH3 | 0 | H | H | CH3 | OCH3 | OCH3 | CH | S | |
| CH3 | 0 | H | H | CH3 | CH3 | CH3 | N | S | |
| CH3 | 0 | H | H | CH3 | CH3 | OCH3 | N | S | |
| CH3 | 0 | H | H | CH3 | OCH3 | OCH3 | N | S | |
| CH3 | 1 | H | H | H | CH3 | CH3 | CH | O | |
| CH3 | 1 | H | H | H | CH3 | OCH3 | CH | O | |
| CH3 | 1 | H | H | H | OCH3 | OCH3 | CH | O | |
| CH3 | 1 | H | H | H | CH3 | CH3 | N | S | |
| CH3 | 1 | H | H | H | CH3 | OCH3 | N | S | |
| CH3 | 1 | H | H | H | OCH3 | OCH3 | N | S | |
| CH3 | 1 | H | H | CH3 | CH3 | CH3 | CH | S | |
| CH3 | 1 | H | H | CH3 | CH3 | OCH3 | CH | S | |
| CH3 | 1 | H | H | CH3 | OCH3 | OCH3 | CH | S | |
| CH3 | 1 | H | H | CH3 | CH3 | CH3 | N | S | |
| CH3 | 1 | H | H | CH3 | CH3 | OCH3 | N | S | |
| CH3 | 1 | H | H | CH3 | OCH3 | OCH3 | N | S | |
| CH3 | 2 | H | H | CH3O | CH3 | CH3 | CH | S | |
| CH3 | 2 | H | H | CH3O | CH3 | CH3O | CH | S | |
| CH3 | 2 | H | H | CH3O | CH3O | CH3O | CH | S | |
| CH3 | 2 | H | H | CH3O | CH3 | CH3 | N | S | |
| CH3 | 2 | H | H | CH3O | CH3 | CH3O | N | S | |
| CH3 | 2 | H | H | CH3O | CH3O | CH3O | N | S | |
| CH3 | 2 | H | H | H | CH3 | CH3 | CH | S | |
| CH3 | 2 | H | H | H | CH3 | OCH3 | CH | S | |
| CH3 | 2 | H | H | H | OCH3 | OCH3 | CH | S | |
| CH3 | 2 | H | H | H | CH3 | CH3 | N | S | |
| CH3 | 2 | H | H | H | CH3 | OCH3 | N | S | |
| CH3 | 2 | H | H | H | OCH3 | OCH3 | N | S | |
| CH3 | 2 | H | H | CH3 | CH3 | CH3 | CH | O | |
| CH3 | 2 | H | H | CH3 | CH3 | OCH3 | CH | O | |
| CH3 | 2 | H | H | CH3 | OCH3 | OCH3 | CH | O | |
| CH3 | 2 | H | H | CH3 | CH3 | CH3 | N | S | |
| CH3 | 2 | H | H | CH3 | CH3 | OCH3 | N | S | |
| CH3 | 2 | H | H | CH3 | OCH3 | OCH3 | N | S | |
| C2H5 | 0 | H | H | H | CH3 | CH3 | CH | S | |
| C2H5 | 0 | H | H | H | CH3 | OCH3 | CH | S | |
| C2H5 | 0 | H | H | H | OCH3 | OCH3 | CH | S | |
| C2H5 | 0 | H | H | H | CH3 | CH3 | N | S | |
| C2H5 | 0 | H | H | H | CH3 | OCH3 | N | S | |
| C2H5 | 0 | H | H | H | OCH3 | OCH3 | N | S | |
| C2H5 | 0 | H | H | CH3 | CH3 | CH3 | CH | O | |
| C2H5 | 0 | H | H | CH3 | CH3 | OCH3 | CH | S | |
| C2H5 | 0 | H | H | CH3 | OCH3 | OCH3 | CH | S | |
| C2H5 | 0 | H | H | CH3 | CH3 | CH3 | N | S | |
| C2H5 | 0 | H | H | CH3 | CH3 | OCH3 | N | S | |
| C2H5 | 0 | H | H | CH3 | OCH3 | OCH3 | N | S | |
| C2H5 | 1 | H | H | H | CH3 | CH3 | CH | O | |
| C2H5 | 1 | H | H | H | CH3 | OCH3 | CH | O | |
| C2H5 | 1 | H | H | H | OCH3 | OCH3 | CH | O | |
| C2H5 | 1 | H | H | H | CH3 | CH3 | N | O | |
| C2H5 | 1 | H | H | H | CH3 | OCH3 | N | S | |
| C2H5 | 1 | H | H | H | OCH3 | OCH3 | N | S | |
| C2H5 | 1 | H | H | CH3 | CH3 | CH3 | CH | S | |
| C2H5 | 1 | H | H | CH3 | CH3 | OCH3 | CH | S | |
| C2H5 | 1 | H | H | CH3 | OCH3 | OCH3 | CH | S | |
| C2H5 | 1 | H | H | CH3 | CH3 | CH3 | N | S | |
| C2H5 | 1 | H | H | CH3 | CH3 | OCH3 | N | S | |
| C2H5 | 1 | H | H | CH3 | OCH3 | OCH3 | N | S | |
| C2H5 | 2 | H | H | H | CH3 | CH3 | CH | S | |
| C2H5 | 2 | H | H | H | CH3 | OCH3 | CH | S | |
| C2H5 | 2 | H | H | H | OCH3 | OCH3 | CH | S | |
| C2H5 | 2 | H | H | H | CH3 | CH3 | N | S | |
| C2H5 | 2 | H | H | H | CH3 | OCH3 | N | S | |
| C2H5 | 2 | H | H | H | OCH3 | OCH3 | N | S | |
| C2H5 | 2 | H | H | CH3 | CH3 | CH3 | CH | S | |
| C2H5 | 2 | H | H | CH3 | CH3 | OCH3 | CH | S | |
| C2H5 | 2 | H | H | CH3 | OCH3 | OCH3 | CH | S | |
| C2H5 | 2 | H | H | CH3 | CH3 | CH3 | N | S | |
| C2H5 | 2 | H | H | CH3 | CH3 | OCH3 | N | S | |
| C2H5 | 2 | H | H | CH3 | OCH3 | OCH3 | N | S | |

TABLE IIIC-continued

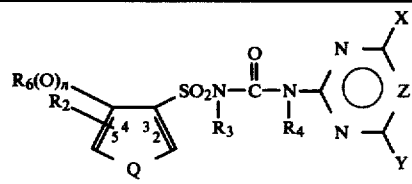

| R6 | n | R2 | R3 | R4 | X | Y | Z | Q | m.p. (°C.) |
|---|---|---|---|---|---|---|---|---|---|
| n-C3H7 | 0 | H | H | H | CH3 | CH3 | CH | S | |
| n-C3H7 | 0 | H | H | H | CH3 | OCH3 | CH | S | |
| n-C3H7 | 0 | H | H | H | OCH3 | OCH3 | CH | S | |
| n-C3H7 | 0 | H | H | H | CH3 | CH3 | N | S | |
| n-C3H7 | 0 | H | H | H | CH3 | OCH3 | N | S | |
| n-C3H7 | 0 | H | H | H | OCH3 | OCH3 | N | S | |
| n-C3H7 | 0 | H | H | CH3 | CH3 | CH3 | CH | S | |
| n-C3H7 | 0 | H | H | CH3 | CH3 | OCH3 | CH | S | |
| n-C3H7 | 0 | H | H | CH3 | OCH3 | OCH3 | CH | S | |
| n-C3H7 | 0 | H | H | CH3 | CH3 | CH3 | N | S | |
| n-C3H7 | 0 | H | H | CH3 | CH3 | OCH3 | N | S | |
| n-C3H7 | 0 | H | H | CH3 | OCH3 | OCH3 | N | S | |
| n-C3H7 | 1 | H | H | H | CH3 | CH3 | CH | S | |
| n-C3H7 | 1 | H | H | H | CH3 | OCH3 | CH | S | |
| n-C3H7 | 1 | H | H | H | OCH3 | OCH3 | CH | S | |
| n-C3H7 | 1 | H | H | H | CH3 | CH3 | N | O | |
| n-C3H7 | 1 | H | H | H | CH3 | OCH3 | N | O | |
| n-C3H7 | 1 | H | H | H | OCH3 | OCH3 | N | O | |
| n-C3H7 | 1 | H | H | CH3 | CH3 | CH3 | CH | S | |
| n-C3H7 | 1 | H | H | CH3 | CH3 | OCH3 | CH | S | |
| n-C3H7 | 1 | H | H | CH3 | OCH3 | OCH3 | CH | S | |
| n-C3H7 | 1 | H | H | CH3 | CH3 | CH3 | N | S | |
| n-C3H7 | 1 | H | H | CH3 | CH3 | OCH3 | N | S | |
| n-C3H7 | 1 | H | H | CH3 | OCH3 | OCH3 | N | S | |
| n-C3H7 | 2 | H | H | H | CH3 | CH3 | CH | O | |
| n-C3H7 | 2 | H | H | H | CH3 | OCH3 | CH | O | |
| n-C3H7 | 2 | H | H | H | OCH3 | OCH3 | CH | O | |
| n-C3H7 | 2 | H | H | H | CH3 | CH3 | N | S | |
| n-C3H7 | 2 | H | H | H | CH3 | OCH3 | N | S | |
| n-C3H7 | 2 | H | H | H | OCH3 | OCH3 | N | S | |
| n-C3H7 | 2 | H | H | CH3 | CH3 | CH3 | CH | S | |
| n-C3H7 | 2 | H | H | CH3 | CH3 | OCH3 | CH | S | |
| n-C3H7 | 2 | H | H | CH3 | OCH3 | OCH3 | CH | S | |
| n-C3H7 | 2 | H | H | CH3 | CH3 | CH3 | N | S | |
| n-C3H7 | 2 | H | H | CH3 | CH3 | OCH3 | N | S | |
| n-C3H7 | 2 | H | H | CH3 | OCH3 | OCH3 | N | S | |
| i-C3H7 | 0 | H | H | H | CH3 | CH3 | CH | O | |
| i-C3H7 | 0 | H | H | H | CH3 | OCH3 | CH | O | |
| i-C3H7 | 0 | H | H | H | OCH3 | OCH3 | CH | O | |
| i-C3H7 | 0 | H | H | H | CH3 | CH3 | N | S | |
| i-C3H7 | 0 | H | H | H | CH3 | OCH3 | N | S | |
| i-C3H7 | 0 | H | H | H | OCH3 | OCH3 | N | S | |
| i-C3H7 | 0 | H | H | CH3 | CH3 | CH3 | CH | S | |
| i-C3H7 | 0 | H | H | CH3 | CH3 | OCH3 | CH | S | |
| i-C3H7 | 0 | H | H | CH3 | OCH3 | OCH3 | CH | S | |
| i-C3H7 | 0 | H | H | CH3 | CH3 | CH3 | N | S | |
| i-C3H7 | 0 | H | H | CH3 | CH3 | OCH3 | N | S | |
| i-C3H7 | 0 | H | H | CH3 | OCH3 | OCH3 | N | S | |
| i-C3H7 | 1 | H | H | H | CH3 | CH3 | CH | S | |
| i-C3H7 | 1 | H | H | H | CH3 | OCH3 | CH | S | |
| i-C3H7 | 1 | H | H | H | OCH3 | OCH3 | CH | S | |
| i-C3H7 | 1 | H | H | H | CH3 | CH3 | N | S | |
| i-C3H7 | 1 | H | H | H | CH3 | OCH3 | N | S | |
| i-C3H7 | 1 | H | H | H | OCH3 | OCH3 | N | S | |
| i-C3H7 | 1 | H | H | CH3 | CH3 | CH3 | CH | O | |
| i-C3H7 | 1 | H | H | CH3 | CH3 | OCH3 | CH | O | |
| i-C3H7 | 1 | H | H | CH3 | OCH3 | OCH3 | CH | O | |
| i-C3H7 | 1 | H | H | CH3 | CH3 | CH3 | N | S | |
| i-C3H7 | 1 | H | H | CH3 | CH3 | OCH3 | N | S | |
| i-C3H7 | 1 | H | H | CH3 | OCH3 | OCH3 | N | S | |
| i-C3H7 | 2 | H | H | H | CH3 | CH3 | CH | S | |
| i-C3H7 | 2 | H | H | H | CH3 | OCH3 | CH | S | |
| i-C3H7 | 2 | H | H | H | OCH3 | OCH3 | CH | S | |
| i-C3H7 | 2 | H | H | H | CH3 | CH3 | N | S | |
| i-C3H7 | 2 | H | H | H | CH3 | OCH3 | N | S | |
| i-C3H7 | 2 | H | H | H | OCH3 | OCH3 | N | S | |
| i-C3H7 | 2 | H | H | CH3 | CH3 | CH3 | CH | S | |
| i-C3H7 | 2 | H | H | CH3 | CH3 | OCH3 | CH | S | |
| i-C3H7 | 2 | H | H | CH3 | OCH3 | OCH3 | CH | S | |
| i-C3H7 | 2 | H | H | CH3 | CH3 | CH3 | N | S | |
| i-C3H7 | 2 | H | H | CH3 | CH3 | OCH3 | N | S | |

TABLE IIIC-continued

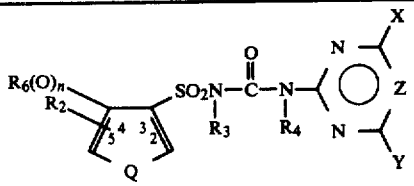

| R₆ | n | R₂ | R₃ | R₄ | X | Y | Z | Q | m.p. (°C.) |
|---|---|---|---|---|---|---|---|---|---|
| i-C₃H₇ | 2 | H | H | CH₃ | OCH₃ | OCH₃ | N | S | |
| CH₂CH=CH₂ | 2 | H | H | H | CH₃ | CH₃ | CH | O | |
| CH₂CH=CH₂ | 2 | H | H | H | CH₃ | OCH₃ | CH | O | |
| CH₂CH=CH₂ | 2 | H | H | H | OCH₃ | OCH₃ | CH | O | |
| CH₂CH=CH₂ | 2 | H | H | H | CH₃ | CH₃ | N | O | |
| CH₂CH=CH₂ | 2 | H | H | H | CH₃ | OCH₃ | N | S | |
| CH₂CH=CH₂ | 2 | H | H | H | OCH₃ | OCH₃ | N | S | |
| CH₂CH=CH₂ | 2 | H | H | CH₃ | CH₃ | CH₃ | CH | S | |
| CH₂CH=CH₂ | 2 | H | H | CH₃ | CH₃ | OCH₃ | CH | S | |
| CH₂CH=CH₂ | 2 | H | H | CH₃ | OCH₃ | OCH₃ | CH | S | |
| CH₂CH=CH₂ | 2 | H | H | CH₃ | CH₃ | CH₃ | N | S | |
| CH₂CH=CH₂ | 2 | H | H | CH₃ | CH₃ | OCH₃ | N | S | |
| CH₂CH=CH₂ | 2 | H | H | CH₃ | OCH₃ | OCH₃ | N | S | |
| cyclopentyl | 2 | H | H | H | CH₃ | CH₃ | CH | S | |
| cyclopentyl | 2 | H | H | H | CH₃ | OCH₃ | CH | S | |
| cyclopentyl | 2 | H | H | H | OCH₃ | OCH₃ | CH | S | |
| cyclopentyl | 2 | H | H | H | CH₃ | CH₃ | N | O | |
| cyclopentyl | 2 | H | H | H | CH₃ | OCH₃ | N | O | |
| cyclopentyl | 2 | H | H | H | OCH₃ | OCH₃ | N | O | |
| cyclopentyl | 2 | H | H | CH₃ | CH₃ | CH₃ | CH | S | |
| cyclopentyl | 2 | H | H | CH₃ | CH₃ | OCH₃ | CH | S | |
| cyclopentyl | 2 | H | H | CH₃ | OCH₃ | OCH₃ | CH | S | |
| cyclopentyl | 2 | H | H | CH₃ | CH₃ | CH₃ | N | S | |
| cyclopentyl | 2 | H | H | CH₃ | CH₃ | OCH₃ | N | S | |
| cyclopentyl | 2 | H | H | CH₃ | OCH₃ | OCH₃ | N | S | |
| cyclopropylmethyl | 2 | H | H | H | CH₃ | CH₃ | CH | S | |
| cyclopropylmethyl | 2 | H | H | H | CH₃ | OCH₃ | CH | S | |
| cyclopropylmethyl | 2 | H | H | H | OCH₃ | OCH₃ | CH | S | |
| cyclopropylmethyl | 2 | H | H | H | CH₃ | CH₃ | N | S | |
| cyclopropylmethyl | 2 | H | H | H | CH₃ | OCH₃ | N | S | |
| cyclopropylmethyl | 2 | H | H | H | OCH₃ | OCH₃ | N | S | |
| cyclopropylmethyl | 2 | H | H | CH₃ | CH₃ | CH₃ | CH | S | |
| cyclopropylmethyl | 2 | H | H | CH₃ | CH₃ | OCH₃ | CH | S | |
| cyclopropylmethyl | 2 | H | H | CH₃ | OCH₃ | OCH₃ | CH | S | |
| cyclopropylmethyl | 2 | H | H | CH₃ | CH₃ | CH₃ | N | S | |
| cyclopropylmethyl | 2 | H | H | CH₃ | CH₃ | OCH₃ | N | S | |
| cyclopropylmethyl | 2 | H | H | CH₃ | OCH₃ | OCH₃ | N | S | |
| n-C₄H₉ | 2 | H | H | H | CH₃ | CH₃ | CH | S | |
| n-C₄H₉ | 2 | H | H | H | CH₃ | OCH₃ | CH | S | |
| n-C₄H₉ | 2 | H | H | H | OCH₃ | OCH₃ | CH | S | |
| n-C₄H₉ | 2 | H | H | H | CH₃ | CH₃ | N | S | |
| n-C₄H₉ | 2 | H | H | H | CH₃ | OCH₃ | N | S | |
| n-C₄H₉ | 2 | H | H | H | OCH₃ | OCH₃ | N | S | |
| n-C₄H₉ | 2 | H | H | CH₃ | CH₃ | CH₃ | CH | S | |
| n-C₄H₉ | 2 | H | H | CH₃ | CH₃ | OCH₃ | CH | S | |
| n-C₄H₉ | 2 | H | H | CH₃ | OCH₃ | OCH₃ | CH | S | |
| n-C₄H₉ | 2 | H | H | CH₃ | CH₃ | CH₃ | N | S | |
| n-C₄H₉ | 2 | H | H | CH₃ | CH₃ | OCH₃ | N | S | |
| n-C₄H₉ | 2 | H | H | CH₃ | OCH₃ | OCH₃ | N | S | |
| CH₃ | 2 | H | CH₃ | H | CH₃ | OCH₃ | N | S | |
| C₂H₅ | 2 | H | CH₃ | H | OCH₃ | OCH₃ | CH | S | |
| n-C₃H₇ | 2 | H | CH₃ | H | OCH₃ | OCH₃ | N | S | |
| i-C₃H₇ | 2 | H | CH₃ | H | CH₃ | CH₃ | CH | S | |
| CH₂CH=CH₂ | 2 | H | CH₃ | H | OCH₃ | OCH₃ | N | S | |
| cyclopentyl | 2 | H | CH₃ | H | OCH₃ | OCH₃ | CH | S | |
| cyclopropylmethyl | 2 | H | CH₃ | H | CH₃ | OCH₃ | N | S | |
| CH₃ | 0 | 2-Cl | H | H | CH₃ | OCH₃ | CH | S | |
| C₂H₅ | 2 | 5-CH₃ | H | H | OCH₃ | OCH₃ | CH | S | |
| n-C₃H₇ | 2 | 2-Br | H | H | CH₃ | OCH₃ | N | O | |
| CH₃ | 2 | H | H | H | CH₃ | OC₂H₅ | CH | S | |
| C₂H₅ | 1 | H | H | H | OCH₃ | C₂H₅ | N | S | |
| CH₃ | 2 | H | H | H | OCH₃ | CH₂OCH₃ | N | S | |
| CH₃ | 2 | H | H | H | OCH₃ | Cl | N | S | |
| CH₃ | 2 | H | H | H | OCH₃ | H | CH | S | |
| t-C₄H₉ | 0 | H | H | H | CH₃ | OCH₃ | N | S | |
| CH₂CH=CHCH₃ | 2 | H | H | H | OCH₃ | OCH₃ | CH | S | |
| i-C₄H₉ | 2 | H | H | H | CH₃ | OCH₃ | N | S | |
| s-C₄H₉ | 2 | H | H | H | OCH₃ | OCH₃ | CH | S | |

TABLE IVA

| R6 | n | R2 | R3 | R4 | Y1 | Q |
|---|---|---|---|---|---|---|
| CH3 | 0 | H | H | H | H | S |
| CH3 | 0 | H | H | H | Cl | S |
| CH3 | 0 | H | H | H | CH3 | S |
| CH3 | 0 | H | H | H | OCH3 | S |
| CH3 | 1 | 4-Cl | H | H | CH3 | S |
| CH3 | 2 | H | H | H | H | O |
| CH3 | 2 | H | H | H | Cl | S |
| CH3 | 2 | H | H | CH3 | CH3 | S |
| CH3 | 2 | H | H | H | OCH3 | S |
| CH3 | 1 | 4-Br | H | H | OCH3 | S |
| CH3 | 2 | 5-CH3 | H | H | CH3 | S |
| CH3 | 2 | H | CH3 | H | H | S |
| C2H5 | 0 | H | H | CH3 | H | S |
| C2H5 | 0 | H | H | H | OCH3 | S |
| C2H5 | 2 | 5-Cl | H | H | H | O |
| i-C3H7 | 2 | H | H | H | CH3 | S |
| n-Bu | 2 | H | H | H | OCH3 | S |
| CH2CH=CH | 1 | H | H | H | OCH3 | S |
| n-C3H7 | 0 | H | H | H | CH3 | S |
| CH2-cyclopropyl | 2 | H | H | H | OCH3 | S |
| cyclopentyl | 2 | 5-Br | H | H | OCH3 | S |
| cyclopentyl | 2 | H | H | H | CH3 | S |

TABLE IVB

| R6 | n | R2 | R3 | R4 | Y1 | Q |
|---|---|---|---|---|---|---|
| CH3 | 0 | H | H | H | H | S |
| CH3 | 0 | H | H | H | Cl | S |
| CH3 | 0 | H | H | H | CH3 | S |
| CH3 | 0 | H | H | H | OCH3 | S |
| CH3 | 1 | 4-Cl | H | H | CH3 | S |
| CH3 | 2 | H | H | H | H | S |
| CH3 | 2 | H | H | H | Cl | S |
| CH3 | 2 | H | H | CH3 | CH3 | S |
| CH3 | 2 | H | H | H | OCH3 | S |
| CH3 | 1 | 4-Br | H | H | OCH3 | S |
| CH3 | 2 | 4-CH3 | H | H | CH3 | S |
| CH3 | 2 | H | CH3 | H | H | O |
| C2H5 | 0 | H | H | CH3 | H | S |
| C2H5 | 0 | H | H | H | OCH3 | S |
| C2H5 | 2 | 5-Cl | H | H | H | S |
| i-C3H7 | 2 | H | H | H | CH3 | S |
| n-Bu | 2 | H | H | H | OCH3 | S |
| CH2CH=CH | 1 | H | H | H | OCH3 | S |
| n-C3H7 | 0 | H | H | H | CH3 | S |
| CH2-cyclopropyl | 2 | H | H | H | OCH3 | S |

TABLE IVB-continued

| R6 | n | R2 | R3 | R4 | Y1 | Q |
|---|---|---|---|---|---|---|
| cyclopentyl | 2 | 5-Br | H | H | OCH3 | S |
| cyclopentyl | 2 | H | H | H | CH3 | S |

TABLE IVC

| R6 | n | R2 | R3 | R4 | Y1 | Q |
|---|---|---|---|---|---|---|
| CH3 | 0 | H | H | H | H | S |
| CH3 | 0 | H | H | H | Cl | S |
| CH3 | 0 | H | H | H | CH3 | S |
| CH3 | 0 | H | H | H | OCH3 | S |
| CH3 | 1 | 2-Cl | H | H | CH3 | O |
| CH3 | 2 | H | H | H | H | O |
| CH3 | 2 | H | H | H | Cl | O |
| CH3 | 2 | H | H | CH3 | CH3 | S |
| CH3 | 2 | H | H | H | OCH3 | S |
| CH3 | 1 | 2-Br | H | H | OCH3 | S |
| CH3 | 2 | 2-CH3 | H | H | CH3 | S |
| CH3 | 2 | H | CH3 | H | H | S |
| C2H5 | 0 | H | H | CH3 | H | S |
| C2H5 | 0 | H | H | H | OCH3 | S |
| C2H5 | 2 | 5-Cl | H | H | H | S |
| i-C3H7 | 2 | H | H | H | CH3 | S |
| n-Bu | 2 | H | H | H | OCH3 | S |
| CH2CH=CH | 1 | H | H | H | OCH3 | S |
| n-C3H7 | 0 | H | H | H | CH3 | S |
| CH2-cyclopropyl | 2 | H | H | H | OCH3 | S |
| cyclopentyl | 2 | 5-Br | H | H | OCH3 | S |
| cyclopentyl | 2 | H | H | H | CH3 | S |

TABLE VA

| R6 | n | R2 | R3 | R4 | Y1 | Q |
|---|---|---|---|---|---|---|
| CH3 | 0 | H | H | H | H | S |
| CH3 | 0 | H | H | H | Cl | S |
| CH3 | 0 | H | H | H | CH3 | S |
| CH3 | 0 | H | H | H | OCH3 | S |

TABLE VA-continued

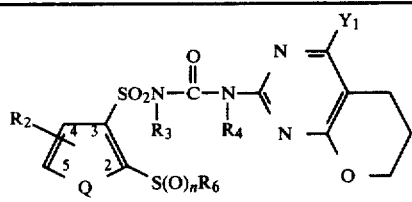

| R₆ | n | R₂ | R₃ | R₄ | Y₁ | Q |
|---|---|---|---|---|---|---|
| CH₃ | 1 | 4-Cl | H | H | CH₃ | S |
| CH₃ | 2 | H | H | H | H | S |
| CH₃ | 2 | H | H | H | Cl | S |
| CH₃ | 2 | H | H | CH₃ | CH₃ | S |
| CH₃ | 2 | H | H | H | OCH₃ | S |
| CH₃ | 1 | 4-Br | H | H | OCH₃ | S |
| CH₃ | 2 | 5-CH₃ | H | H | CH₃ | S |
| CH₃ | 2 | H | CH₃ | H | H | S |
| C₂H₅ | 0 | H | H | CH₃ | H | S |
| C₂H₅ | 0 | H | H | H | OCH₃ | S |
| C₂H₅ | 2 | 5-Cl | H | H | H | O |
| i-C₃H₇ | 2 | H | H | H | CH₃ | S |
| n-Bu | 2 | H | H | H | OCH₃ | S |
| CH₂CH=CH | 1 | H | H | H | OCH₃ | S |
| n-C₃H₇ | 0 | H | H | H | CH₃ | S |
| CH₂-◁ | 2 | H | H | H | OCH₃ | O |
| cyclopentyl | 2 | 4-Br | H | H | OCH₃ | S |
| cyclopentyl | 2 | H | H | H | CH₃ | S |

TABLE VB

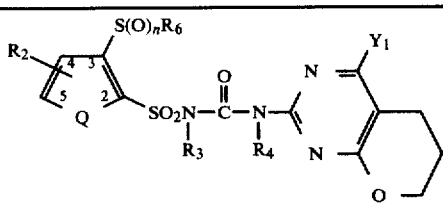

| R₆ | n | R₂ | R₃ | R₄ | Y₁ | Q |
|---|---|---|---|---|---|---|
| CH₃ | 0 | H | H | H | H | S |
| CH₃ | 0 | H | H | H | Cl | S |
| CH₃ | 0 | H | H | H | CH₃ | S |
| CH₃ | 0 | H | H | H | OCH₃ | S |
| CH₃ | 1 | 4-Cl | H | H | CH₃ | S |
| CH₃ | 2 | H | H | H | H | S |
| CH₃ | 2 | H | H | H | Cl | S |
| CH₃ | 2 | H | H | CH₃ | CH₃ | O |
| CH₃ | 2 | H | H | H | OCH₃ | S |
| CH₃ | 1 | 5-Br | H | H | OCH₃ | S |
| CH₃ | 2 | 5-CH₃ | H | H | CH₃ | S |
| CH₃ | 2 | H | CH₃ | H | H | S |
| C₂H₅ | 0 | H | H | CH₃ | H | S |
| C₂H₅ | 0 | H | H | H | OCH₃ | S |
| C₂H₅ | 2 | 4-Cl | H | H | H | S |
| i-C₃H₇ | 2 | H | H | H | CH₃ | S |
| n-Bu | 2 | H | H | H | OCH₃ | S |
| CH₂CH=CH | 1 | H | H | H | OCH₃ | S |
| n-C₃H₇ | 0 | H | H | H | CH₃ | S |
| CH₂-◁ | 2 | H | H | H | OCH₃ | S |
| cyclopentyl | 2 | 4-Br | H | H | OCH₃ | O |

TABLE VB-continued

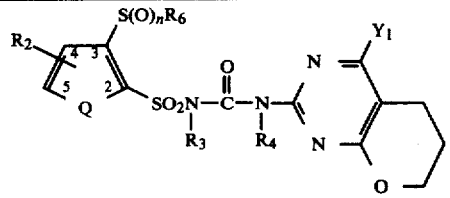

| R₆ | n | R₂ | R₃ | R₄ | Y₁ | Q |
|---|---|---|---|---|---|---|
| cyclopentyl | 2 | H | H | H | CH₃ | O |

TABLE VC

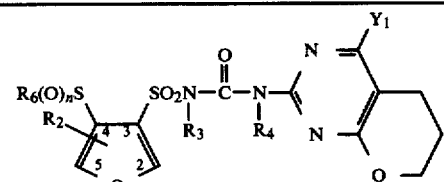

| R₆ | n | R₂ | R₃ | R₄ | Y₁ | Q |
|---|---|---|---|---|---|---|
| CH₃ | 0 | H | H | H | H | S |
| CH₃ | 0 | H | H | H | Cl | O |
| CH₃ | 0 | H | H | H | CH₃ | O |
| CH₃ | 0 | H | H | H | OCH₃ | O |
| CH₃ | 1 | 5-Cl | H | H | CH₃ | O |
| CH₃ | 2 | H | H | H | H | O |
| CH₃ | 2 | H | H | H | Cl | O |
| CH₃ | 2 | H | H | CH₃ | CH₃ | O |
| CH₃ | 2 | H | H | H | OCH₃ | S |
| CH₃ | 1 | 5-Br | H | H | OCH₃ | S |
| CH₃ | 2 | 2-CH₃ | H | H | CH₃ | S |
| CH₃ | 2 | H | CH₃ | H | H | S |
| C₂H₅ | 0 | H | H | CH₃ | H | S |
| C₂H₅ | 0 | H | H | H | OCH₃ | S |
| C₂H₅ | 2 | 2-Cl | H | H | H | S |
| i-C₃H₇ | 2 | H | H | H | CH₃ | S |
| n-Bu | 2 | H | H | H | OCH₃ | S |
| CH₂CH=CH | 1 | H | H | H | OCH₃ | S |
| n-C₃H₇ | 0 | H | H | H | CH₃ | S |
| CH₂-◁ | 2 | H | H | H | OCH₃ | S |
| cyclopentyl | 2 | 2-Br | H | H | OCH₃ | S |
| cyclopentyl | 2 | H | H | H | CH₃ | S |

TABLE VIA

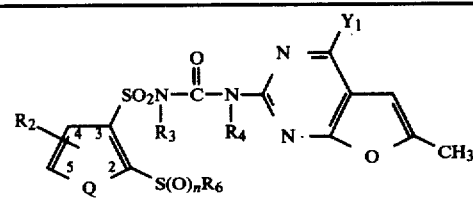

| R₆ | n | R₂ | R₃ | R₄ | Y₁ | Q |
|---|---|---|---|---|---|---|
| CH₃ | 0 | H | H | H | H | O |
| CH₃ | 0 | H | H | H | Cl | S |
| CH₃ | 0 | H | H | H | CH₃ | S |
| CH₃ | 0 | H | H | H | OCH₃ | S |
| CH₃ | 1 | 4-Cl | H | H | CH₃ | S |
| CH₃ | 2 | H | H | H | H | S |
| CH₃ | 2 | H | H | H | Cl | S |

TABLE VIA-continued

Structure: R₂-substituted ring (positions 2,3,4,5 with Q) with S(O)ₙR₆ at 2-position and SO₂N(R₃)C(O)N(R₄)-[pyrimidine with Y₁ and furan-CH₃]

| R₆ | n | R₂ | R₃ | R₄ | Y₁ | Q |
|---|---|---|---|---|---|---|
| CH₃ | 2 | H | H | CH₃ | CH₃ | S |
| CH₃ | 2 | H | H | H | OCH₃ | S |
| CH₃ | 1 | 5-Br | H | H | OCH₃ | S |
| CH₃ | 2 | 4-CH₃ | H | H | CH₃ | S |
| CH₃ | 2 | H | CH₃ | H | H | S |
| C₂H₅ | 0 | H | H | CH₃ | H | S |
| C₂H₅ | 0 | H | H | H | OCH₃ | S |
| C₂H₅ | 2 | 5-Cl | H | H | H | S |
| i-C₃H₇ | 2 | H | H | H | CH₃ | S |
| n-Bu | 2 | H | H | H | OCH₃ | S |
| CH₂CH=CH | 1 | H | H | H | OCH₃ | S |
| n-C₃H₇ | 0 | H | H | H | CH₃ | S |
| CH₂—▷ (cyclopropyl) | 2 | H | H | H | OCH₃ | O |
| cyclopentyl | 2 | 4-Br | H | H | OCH₃ | O |
| cyclopentyl | 2 | H | H | H | CH₃ | O |

TABLE VIB

| R₆ | n | R₂ | R₃ | R₄ | Y₁ | Q |
|---|---|---|---|---|---|---|
| CH₃ | 0 | H | H | H | H | S |
| CH₃ | 0 | H | H | H | Cl | S |
| CH₃ | 0 | H | H | H | CH₃ | S |
| CH₃ | 0 | H | H | H | OCH₃ | O |
| CH₃ | 1 | 5-Cl | H | H | CH₃ | S |
| CH₃ | 2 | H | H | H | H | S |
| CH₃ | 2 | H | H | H | Cl | S |
| CH₃ | 2 | H | H | CH₃ | CH₃ | S |
| CH₃ | 2 | H | H | H | OCH₃ | S |
| CH₃ | 1 | 5-Br | H | H | OCH₃ | S |
| CH₃ | 2 | 4-CH₃ | H | H | CH₃ | S |
| CH₃ | 2 | H | CH₃ | H | H | S |
| C₂H₅ | 0 | H | H | CH₃ | H | S |
| C₂H₅ | 0 | H | H | H | OCH₃ | S |
| C₂H₅ | 2 | 4-Cl | H | H | H | O |
| i-C₃H₇ | 2 | H | H | H | CH₃ | S |
| n-Bu | 2 | H | H | H | OCH₃ | S |
| CH₂CH=CH | 1 | H | H | H | OCH₃ | S |
| n-C₃H₇ | 0 | H | H | H | CH₃ | S |
| CH₂—▷ (cyclopropyl) | 2 | H | H | H | OCH₃ | S |
| cyclopentyl | 2 | 5-Br | H | H | OCH₃ | S |
| cyclopentyl | 2 | H | H | H | CH₃ | S |

TABLE VIC

| R₆ | n | R₂ | R₃ | R₄ | Y₁ | Q |
|---|---|---|---|---|---|---|
| CH₃ | 0 | H | H | H | H | S |
| CH₃ | 0 | H | H | H | Cl | S |
| CH₃ | 0 | H | H | H | CH₃ | S |
| CH₃ | 0 | H | H | H | OCH₃ | S |
| CH₃ | 1 | 5-Cl | H | H | CH₃ | S |
| CH₃ | 2 | H | H | H | H | S |
| CH₃ | 2 | H | H | H | Cl | S |
| CH₃ | 2 | H | H | CH₃ | CH₃ | O |
| CH₃ | 2 | H | H | H | OCH₃ | O |
| CH₃ | 1 | 2-Br | H | H | OCH₃ | O |
| CH₃ | 2 | 5-CH₃ | H | H | CH₃ | S |
| CH₃ | 2 | H | CH₃ | H | H | S |
| C₂H₅ | 0 | H | H | CH₃ | H | S |
| C₂H₅ | 0 | H | H | H | OCH₃ | S |
| C₂H₅ | 2 | 5-Cl | H | H | H | S |
| i-C₃H₇ | 2 | H | H | H | CH₃ | S |
| n-Bu | 2 | H | H | H | OCH₃ | S |
| CH₂CH=CH | 1 | H | H | H | OCH₃ | S |
| n-C₃H₇ | 0 | H | H | H | CH₃ | S |
| CH₂—▷ (cyclopropyl) | 2 | H | H | H | OCH₃ | S |
| cyclopentyl | 2 | 2-Br | H | H | OCH₃ | S |
| cyclopentyl | 2 | H | H | H | CH₃ | O |

TABLE VIIA

| R₆ | n | R₂ | R₃ | R₄ | X | Y₂ | Q |
|---|---|---|---|---|---|---|---|
| CH₃ | 2 | H | H | CH₃ | CH₃ | OCH₃ | S |
| CH₃ | 2 | H | CH₃ | H | OCH₃ | OCH₃ | S |
| CH₃ | 2 | H | H | H | CH₃ | OCH₃ | S |
| CH₃ | 2 | H | H | H | OCH₃ | CH₃ | O |
| CH₃ | 0 | H | H | H | CH₃ | CH₃ | S |
| CH₃ | 0 | 5-Cl | H | H | CH₃ | CH₃ | S |
| C₂H₅ | 2 | H | H | H | CH₃ | CH₃ | S |
| C₂H₅ | 2 | H | H | H | CH₃ | OCH₃ | S |
| n-C₃H₇ | 2 | H | H | H | OCH₃ | CH₃ | S |
| n-C₃H₇ | 2 | H | H | H | OCH₃ | OCH₃ | O |
| n-C₃H₇ | 0 | H | H | H | OCH₃ | CH₃ | S |
| n-C₄H₉ | 2 | 4-Br | H | H | OCH₃ | CH₃ | S |
| n-C₄H₉ | 0 | H | H | H | CH₃ | OCH₃ | S |
| n-C₄H₉ | 2 | H | H | H | OCH₃ | CH₃ | S |
| i-C₃H₇ | 2 | H | H | H | CH₃ | CH₃ | S |
| i-C₃H₇ | 2 | H | H | H | OCH₃ | CH₃ | S |
| i-C₃H₇ | 2 | H | H | H | CH₃ | OCH₃ | S |
| CH₂CH=CH₂ | 0 | H | H | H | OCH₃ | CH₃ | S |

TABLE VIIB

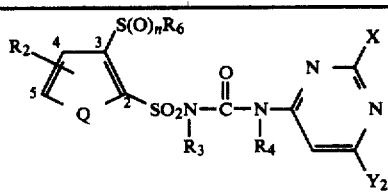

| R6 | n | R2 | R3 | R4 | X | Y2 | Q |
|---|---|---|---|---|---|---|---|
| CH3 | 2 | H | H | CH3 | CH3 | OCH3 | S |
| CH3 | 2 | H | CH3 | H | OCH3 | OCH3 | S |
| CH3 | 2 | H | H | H | CH3 | OCH3 | S |
| CH3 | 2 | H | H | H | OCH3 | CH3 | O |
| CH3 | 0 | H | H | H | CH3 | CH3 | S |
| CH3 | 0 | 5-CH3 | H | H | CH3 | CH3 | S |
| C2H5 | 2 | H | H | H | CH3 | CH3 | S |
| C2H5 | 2 | H | H | H | CH3 | OCH3 | S |
| n-C3H7 | 2 | H | H | H | OCH3 | CH3 | S |
| n-C3H7 | 2 | H | H | H | OCH3 | OCH3 | O |
| n-C3H7 | 0 | H | H | H | OCH3 | OCH3 | S |
| n-C4H9 | 2 | 4-Br | H | H | OCH3 | OCH3 | S |
| n-C4H9 | 0 | H | H | H | CH3 | OCH3 | S |
| n-C4H9 | 2 | H | H | H | OCH3 | OCH3 | S |
| i-C3H7 | 2 | H | H | H | CH3 | CH3 | S |
| i-C3H7 | 2 | H | H | H | OCH3 | CH3 | S |
| i-C3H7 | 2 | H | H | H | OCH3 | OCH3 | S |
| CH2CH=CH2 | 0 | H | H | H | OCH3 | CH3 | S |

TABLE VIIC

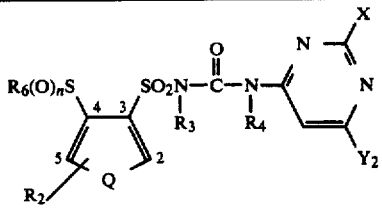

| R6 | n | R2 | R3 | R4 | X | Y2 | Q |
|---|---|---|---|---|---|---|---|
| CH3 | 2 | H | H | CH3 | CH3 | OCH3 | S |
| CH3 | 2 | H | CH3 | H | OCH3 | OCH3 | S |
| CH3 | 2 | H | H | H | CH3 | OCH3 | S |
| CH3 | 2 | H | H | H | OCH3 | CH3 | O |
| CH3 | 0 | H | H | H | CH3 | CH3 | S |
| CH3 | 0 | 2-Cl | H | H | CH3 | CH3 | S |
| C2H5 | 2 | H | H | H | CH3 | CH3 | S |
| C2H5 | 2 | H | H | H | CH3 | OCH3 | S |
| n-C3H7 | 2 | H | H | H | OCH3 | CH3 | S |
| n-C3H7 | 2 | H | H | H | OCH3 | OCH3 | O |
| n-C3H7 | 0 | H | H | H | OCH3 | OCH3 | S |
| n-C4H9 | 2 | 5-CH3 | H | H | OCH3 | OCH3 | S |
| n-C4H9 | 0 | H | H | H | CH3 | OCH3 | S |
| n-C4H9 | 2 | H | H | H | OCH3 | OCH3 | S |
| i-C3H7 | 2 | H | H | H | CH3 | CH3 | S |
| i-C3H7 | 2 | H | H | H | OCH3 | CH3 | S |
| i-C3H7 | 2 | H | H | H | OCH3 | OCH3 | S |
| CH2CH=CH2 | 0 | H | H | H | OCH3 | CH3 | S |

TABLE VIIIA

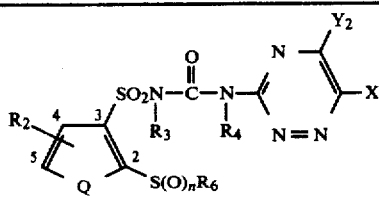

| R6 | n | R2 | R3 | R4 | X | Y2 | Q |
|---|---|---|---|---|---|---|---|
| CH3 | 2 | H | H | CH3 | CH3 | OCH3 | S |
| CH3 | 2 | H | CH3 | H | OCH3 | OCH3 | S |
| CH3 | 2 | H | H | H | CH3 | OCH3 | S |

TABLE VIIIA-continued

| R6 | n | R2 | R3 | R4 | X | Y2 | Q |
|---|---|---|---|---|---|---|---|
| CH3 | 2 | H | H | H | OCH3 | CH3 | O |
| CH3 | 0 | H | H | H | CH3 | CH3 | S |
| CH3 | 0 | 4-Cl | H | H | CH3 | CH3 | S |
| C2H5 | 2 | H | H | H | CH3 | CH3 | S |
| C2H5 | 2 | H | H | H | CH3 | OCH3 | S |
| n-C3H7 | 2 | H | H | H | OCH3 | CH3 | S |
| n-C3H7 | 2 | H | H | H | OCH3 | OCH3 | O |
| n-C3H7 | 0 | H | H | H | OCH3 | OCH3 | S |
| n-C4H9 | 2 | 5-CH3 | H | H | OCH3 | OCH3 | S |
| n-C4H9 | 0 | H | H | H | CH3 | OCH3 | S |
| n-C4H9 | 2 | H | H | H | OCH3 | OCH3 | S |
| i-C3H7 | 2 | H | H | H | CH3 | CH3 | S |
| i-C3H7 | 2 | H | H | H | OCH3 | CH3 | S |
| i-C3H7 | 2 | H | H | H | OCH3 | OCH3 | S |
| CH2CH=CH2 | 0 | H | H | H | OCH3 | CH3 | S |

TABLE VIIIB

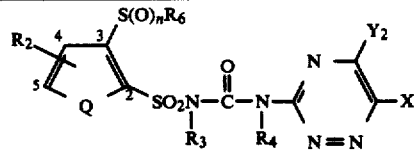

| R6 | n | R2 | R3 | R4 | X | Y2 | Q |
|---|---|---|---|---|---|---|---|
| CH3 | 2 | H | H | CH3 | CH3 | OCH3 | S |
| CH3 | 2 | H | CH3 | H | OCH3 | OCH3 | S |
| CH3 | 2 | H | H | H | CH3 | OCH3 | S |
| CH3 | 2 | H | H | H | OCH3 | CH3 | O |
| CH3 | 0 | H | H | H | CH3 | CH3 | S |
| CH3 | 0 | 4-Br | H | H | CH3 | CH3 | S |
| C2H5 | 2 | H | H | H | CH3 | CH3 | S |
| C2H5 | 2 | H | H | H | CH3 | OCH3 | S |
| n-C3H7 | 2 | H | H | H | OCH3 | CH3 | S |
| n-C3H7 | 2 | H | H | H | OCH3 | OCH3 | O |
| n-C3H7 | 0 | H | H | H | OCH3 | OCH3 | S |
| n-C4H9 | 2 | 5-Cl | H | H | OCH3 | OCH3 | S |
| n-C4H9 | 0 | H | H | H | CH3 | OCH3 | S |
| n-C4H9 | 2 | H | H | H | OCH3 | OCH3 | S |
| i-C3H7 | 2 | H | H | H | CH3 | CH3 | S |
| i-C3H7 | 2 | H | H | H | OCH3 | CH3 | S |
| i-C3H7 | 2 | H | H | H | OCH3 | OCH3 | S |
| CH2CH=CH2 | 0 | H | H | H | OCH3 | CH3 | S |

TABLE VIIIC

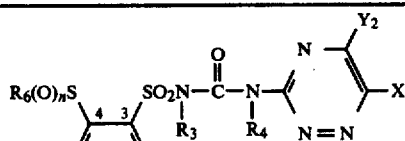

| R6 | n | R2 | R3 | R4 | X | Y2 | Q |
|---|---|---|---|---|---|---|---|
| CH3 | 2 | H | H | CH3 | CH3 | OCH3 | S |
| CH3 | 2 | H | CH3 | H | OCH3 | OCH3 | S |
| CH3 | 2 | H | H | H | CH3 | OCH3 | S |
| CH3 | 2 | H | H | H | OCH3 | CH3 | O |
| CH3 | 0 | H | H | H | CH3 | CH3 | S |
| CH3 | 0 | 5-Cl | H | H | CH3 | CH3 | S |
| C2H5 | 2 | H | H | H | CH3 | CH3 | S |

TABLE VIIIC-continued

[Structure: R6(O)nS on position 4, R2 on position 5, Q ring with positions 2,3,4,5; SO2N(R3)-C(=O)-N(R4)-C(=N-N=)-X with Y2, pyrimidine-like ring]

| R6 | n | R2 | R3 | R4 | X | Y2 | Q |
|---|---|---|---|---|---|---|---|
| C2H5 | 2 | H | H | H | CH3 | OCH3 | S |
| n-C3H7 | 2 | H | H | H | OCH3 | CH3 | S |
| n-C3H7 | 2 | H | H | H | OCH3 | OCH3 | O |
| n-C3H7 | 0 | H | H | H | OCH3 | OCH3 | S |
| n-C4H9 | 2 | 2-Cl | H | H | OCH3 | OCH3 | S |
| n-C4H9 | 0 | H | H | H | CH3 | OCH3 | S |
| n-C4H9 | 2 | H | H | H | OCH3 | CH3 | S |
| i-C3H7 | 2 | H | H | H | CH3 | CH3 | S |
| i-C3H7 | 2 | H | H | H | OCH3 | CH3 | S |
| i-C3H7 | 2 | H | H | H | OCH3 | OCH3 | S |
| CH2CH=CH2 | 0 | H | H | H | OCH3 | CH3 | S |

TABLE IXA

[Structure with SO2N(R3)-C(=O)-N(R4)-C(=N-Y1)(cyclopentylidene), R2 at 4, S(O)nR6 at 2, Q ring]

| R6 | n | R2 | R3 | R4 | Y1 | Q |
|---|---|---|---|---|---|---|
| CH3 | 2 | H | CH3 | H | CH3 | S |
| CH3 | 2 | H | H | CH3 | OCH3 | S |
| CH3 | 2 | H | H | H | CH3 | S |
| CH3 | 2 | H | H | H | OCH3 | S |
| CH3 | 2 | H | H | H | CH3 | O |
| CH3 | 0 | 4-CH3 | H | H | OCH3 | S |
| CH3 | 2 | H | H | H | OCH3 | S |
| CH3 | 0 | H | H | H | OCH3 | S |
| C2H5 | 2 | H | H | H | OCH3 | S |
| C2H5 | 2 | H | H | H | OCH3 | S |
| C2H5 | 2 | H | H | H | CH3 | S |
| n-C3H7 | 2 | H | H | H | CH3 | S |
| n-C3H7 | 0 | H | H | H | CH3 | S |
| n-C3H7 | 2 | H | H | H | CH3 | S |
| n-C4H7 | 2 | H | H | H | OCH3 | S |
| n-C4H7 | 2 | H | H | H | CH3 | S |
| n-C4H7 | 2 | 5-CH3 | H | H | OCH3 | S |
| i-C3H7 | 0 | H | H | H | OCH3 | O |
| i-C3H7 | 2 | H | H | H | OCH3 | S |
| i-C3H7 | 2 | H | H | H | CH3 | S |
| cyclopentyl | 2 | H | H | H | OCH3 | S |

TABLE IXB

[Structure with S(O)nR6 at 3, R2 at 4, SO2N(R3)-C(=O)-N(R4)-C(=N-Y1)(cyclopentylidene), Q ring]

| R6 | n | R2 | R3 | R4 | Y1 | Q |
|---|---|---|---|---|---|---|
| CH3 | 2 | H | CH3 | H | CH3 | S |
| CH3 | 2 | H | H | CH3 | OCH3 | S |
| CH3 | 2 | H | H | H | CH3 | S |
| CH3 | 2 | H | H | H | OCH3 | S |
| CH3 | 2 | H | H | H | CH3 | O |
| CH3 | 0 | 4-CH3 | H | H | OCH3 | S |
| CH3 | 2 | H | H | H | OCH3 | S |

TABLE IXB-continued

| R6 | n | R2 | R3 | R4 | Y1 | Q |
|---|---|---|---|---|---|---|
| CH3 | 0 | H | H | H | OCH3 | S |
| C2H5 | 2 | H | H | H | OCH3 | S |
| C2H5 | 2 | H | H | H | OCH3 | S |
| C2H5 | 2 | H | H | H | CH3 | S |
| n-C3H7 | 2 | H | H | H | CH3 | S |
| n-C3H7 | 0 | H | H | H | CH3 | S |
| n-C3H7 | 2 | H | H | H | CH3 | S |
| n-C4H7 | 2 | H | H | H | OCH3 | S |
| n-C4H7 | 2 | H | H | H | CH3 | S |
| n-C4H7 | 2 | 5-Br | H | H | OCH3 | S |
| i-C3H7 | 0 | H | H | H | OCH3 | O |
| i-C3H7 | 2 | H | H | H | OCH3 | S |
| i-C3H7 | 2 | H | H | H | CH3 | S |
| cyclopentyl | 2 | H | H | H | OCH3 | S |

TABLE IXC

[Structure with R6(O)nS at 4, R2 at 5, SO2N(R3)-C(=O)-N(R4)-C(=N-Y1)(cyclopentylidene), Q ring]

| R6 | n | R2 | R3 | R4 | Y1 | Q |
|---|---|---|---|---|---|---|
| CH3 | 2 | H | CH3 | H | CH3 | S |
| CH3 | 2 | H | H | CH3 | OCH3 | S |
| CH3 | 2 | H | H | H | CH3 | S |
| CH3 | 2 | H | H | H | OCH3 | S |
| CH3 | 2 | H | H | H | CH3 | O |
| CH3 | 0 | 2-CH3 | H | H | OCH3 | S |
| CH3 | 2 | H | H | H | OCH3 | S |
| CH3 | 0 | H | H | H | OCH3 | S |
| C2H5 | 2 | H | H | H | OCH3 | S |
| C2H5 | 2 | H | H | H | OCH3 | S |
| C2H5 | 2 | H | H | H | CH3 | S |
| n-C3H7 | 2 | H | H | H | CH3 | S |
| n-C3H7 | 0 | H | H | H | CH3 | S |
| n-C3H7 | 2 | H | H | H | CH3 | S |
| n-C4H7 | 2 | H | H | H | OCH3 | S |
| n-C4H7 | 2 | H | H | H | CH3 | S |
| n-C4H7 | 2 | 5-Cl | H | H | OCH3 | S |
| i-C3H7 | 0 | H | H | H | OCH3 | O |
| i-C3H7 | 2 | H | H | H | OCH3 | S |
| i-C3H7 | 2 | H | H | H | CH3 | S |
| cyclopentyl | 2 | H | H | H | OCH3 | S |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE VII

|  | Active Ingredient | Weight Percent* | |
|---|---|---|---|
|  |  | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J. but other solids, either mined or manufactured, may be used. The more absorptive diluents are preferred for wettable powders an the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preferred granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley & Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 7

| Wettable Powder | |
|---|---|
| N—[(4,6-dimethylpyrimidin-2-yl)aminocarbonyl]-2-(methylsulfonyl)-3-thiophenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 8

| Wettable Powder | |
|---|---|
| N—[(4,6-dimethylpyrimidin-2-yl)aminocarbonyl]-2-(methylsulfonyl)-3-thiophenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 9

| Granule | |
|---|---|
| Wettable Powder of Example 8 | 5% |
| attapulgite granules (U.S.S. 20–40 mesh; 0.84–0.42 mm) | 95% |

A slurry of wettable powder containing 25% solids is sprayed on the surface of attapulgite granules in a double-cone blender. The granules are dried and packaged.

EXAMPLE 10

| Extruded Pellet | |
|---|---|
| N—[(4-methoxy-6-methylpyrimidin-2-yl)aminocarbonyl]-2-(methylsulfonyl)-3-thiophenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on U.S.S. No. 40 sieve (0.42 mm openings) may be packaged for use and the fines recycled.

EXAMPLE 11

| Oil Suspension | |
|---|---|
| N—[(4-methoxy-6-methylpyrimidin-2-yl)aminocarbonyl]-2-(methylsulfonyl)-3-thiophenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 12

| Wettable Powder | |
|---|---|
| N—[(4,6-dimethylpyrimidin-2-yl)aminocarbonyl]-2-(methylsulfonyl)-3-thiophenesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 13

| Low Strength Granule | |
|---|---|
| N—[(4-methoxy-6-methylpyrimidin-2-yl)aminocarbonyl]-2-(methylsulfonyl)-3-thiophenesulfonamide | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 14

| Aqueous Suspension | |
|---|---|
| N—[(4,6-dimethylpyrimidin-2-yl)aminocarbonyl]-2-(methylsulfonyl)-3-thiophenesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 15

| Solution | |
|---|---|
| N—[(4,6-dimethylpyrimidin-2-yl)aminocarbonyl]-2-(methylsulfonyl)-3-thiophenesulfonamide, sodium salt | 5% |
| water | 95% |

The salt is added directly to the water with stirring to produce the solution, which may then be packaged for use.

EXAMPLE 16

| Low Strength Granule | |
|---|---|
| N—[(4-methoxy-6-methylpyrimidin-2-yl)aminocarbonyl]-2-(methylsulfonyl)-3-thiophenesulfonamide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 17

| Granule | |
|---|---|
| N—[(4,6-dimethylpyrimidin-2-yl)aminocarbonyl]-2-(methylsulfonyl)-3-thiophenesulfonamide | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 18

High Strength Concentrate

| High Strength Concentrate | |
|---|---|
| N—[(4-methoxy-6-methylpyrimidin-2-yl)aminocarbonyl]-2-(methylsulfonyl)-3-thiophenesulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 19

| Wettable Powder | |
|---|---|
| N—[(4,6-dimethylpyrimidin-2-yl)aminocarbonyl]-2-(methylsulfonyl)-3-thiophenesulfonamide | 90% |

-continued

Wettable Powder

| | |
|---|---|
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 20

Wettable Powder

| | |
|---|---|
| N—[(4,6-dimethylpyrimidin-2-yl)aminocarbonyl]-2-(methylsulfonyl)-3-thiophenesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 21

Oil Suspension

| | |
|---|---|
| N—[(4-methoxy-6-methylpyrimidin-2-yl)aminocarbonyl]-2-(methylsulfonyl)-3-thiophenesulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 22

Dust

| | |
|---|---|
| N—[(4,6-dimethylpyrimidin-2-yl)aminocarbonyl]-2-(methylsulfonyl)-3-thiophenesulfonamide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

UTILITY

The compounds of the present invention are active herbicides. They have utility for broad-spectrum pre- and/or post-emergence weed control in areas where complete control of all vegetation is desired, such as around fuel storage tanks, ammunition depots, industrial storage areas, oil-well sites, drive-in theaters, around billboards, highway and railroad structures. By properly selecting rate, time and method of application, compounds of this invention may also be used to modify plant growth beneficially, and also to selectively control weeds in crops such as wheat, barley, corn and soybeans.

The precise amount of the compounds of Formula I to be used in any given situation will vary according to the particular end result desired, the amount of foliage present, the weeds to be controlled, the crop species involved, the soil type, the formulation and mode of application, weather conditions, etc. Since so many variables play a role, it is not possible to state a rate of application suitable for all situations. Broadly speaking, the compounds of this invention are used at levels of about 0.01 to 20 kg/ha with a preferred range of 0.03 to 10 kg/ha. In general, the higher rates of application from within this range will be selected for adverse conditions or where extended persistence in soil is desired.

The compounds of Formula I may be combined with other herbicides and are particularly useful in combination with the ureas: such as 3-(3,4-dichlorophenyl)-1,1-dimethylurea (diuron); the triazines: such as 2-chloro-4-(ethylamino)-6-(isopropylamino)-s-triazine (atrazine); the uracils: such as 5-bromo-3-sec-butyl-6-methyluracil (bromacil); N-(phosphonomethyl)glycine (glyphosate); 3-cyclohexyl-1-methyl-6-dimethylamino-s-triazine-2,4(1H,3H)-dione (hexazinone); N,N-dimethyl-2,2-diphenylacetamide (diphenamid); 2,4-dichlorophenoxyacetic acid (2,4-D) (and closely related compounds); 4-chloro-2-butynyl-3-chlorophenylcarbamate (barban); S-(2,3-dichloroallyl)-diisopropylthiocarbamate (diallate); S-(2,3,3-trichloroallyl-diisopropylthiocarbamate (triallate); 1,2-dimethyl-3,5-diphenyl-1H-pyrazolium methyl sulfate (difenzoquat methyl sulfate); methyl 2-[4-(2,4-dichlorophenoxy)phenoxy]propanoate (diclofop methyl); 4-amino-6-tert-butyl-3-(methylthio)-1,2,4-triazin-5(4H)-one (metribuzin); 3-(3,4-dichlorophenyl)-1-methoxy-1-methylurea (linuron); 3-isopropyl-1H-2,1,3-benzothiodiazin-4(3H)-one-2,2-dioxide (bentazon); α,α,α-trifluoro-2,6-dinitro-N,N-dipropyl-p-toluidine (trifluralin); 1,1'-dimethyl-4,4'-bipyridinium ion (paraquat); monosodium methanearsonate (MSMA); 2-chloro-2',6'-diethyl (methoxymethyl)acetanilide (alachlor); 1,1-dimethyl-3-(α,α,α-trifluoro-m-tolyl)-urea (fluometuron); and 5-[2-chloro-4-trifluoromethyl)phenoxy]-2-nitrobenzoic acid, methyl ester (acifluorfen-methyl).

The activity of these compounds was discovered in greenhouse tests. The tests are described and data resulting from them are shown below. It will be seen that certain of the compounds tested provide effective weed control at rates of application which are non-injurious to wheat, corn, or soybeans.

Test A

Seeds of crabgrass (Digitaria spp.), barnyardgrass (Echinochloa crusgalli), wild oats (Avena fatua), cassia (Cassia tora), morningglory (Ipomoea sp.), cocklebur (Xanthium spp.), sorghum, corn, soybean, rice, wheat and nutsedge tubers (Cyperus rotundus) were planted in a growth medium and treated pre-emergence with the chemicals dissolved in a non-phytotoxic solvent. At the same time, cotton having five leaves (including cotyledonary ones), bush beans with the second trifoliate leaf expanding, crabgrass and barnyardgrass with two leaves, wild oats with one leaf, cassia with three leaves (including cotyledonary ones), morningglory and cocklebur with four leaves (including the cotyledonary ones), sorghum with three leaves, corn with three leaves, soybean with two cotyledonary leaves, rice with two leaves, wheat with two leaves, and nutsedge with three to five leaves were sprayed. Treated plants and controls were maintained in a greenhouse for sixteen days, then all species were compared to controls and visually rated for response to treatment.

The ratings are based on a numerical scale extending from 0=no injury, to 10=complete kill. The accompanying descriptive symbols have the following meanings:
G=growth retardation
C=chlorosis or necrosis
E=emergence inhibition
H=formative effects
6Y=abscised buds or flowers
U=unusual pigmentation
X=axillary stimulation
P=terminal bud killed
D=defoliation
A=growth acceleration Compound 1

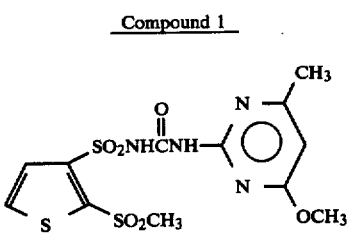

Compound 2

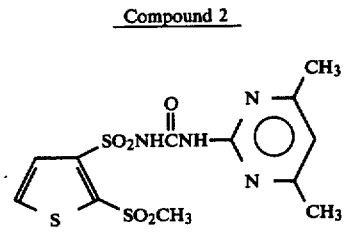

Compound 3

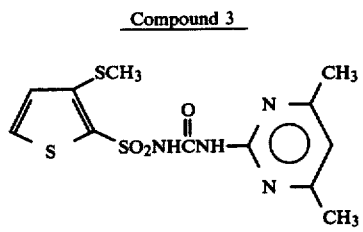

Compound 4

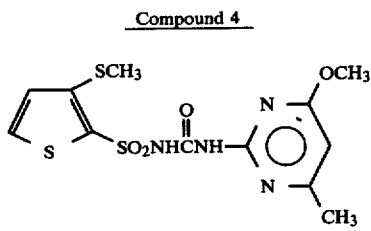

Compound 5

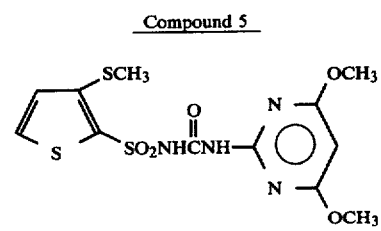

Compound 6

-continued

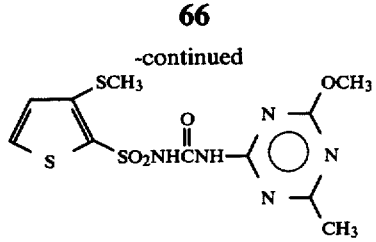

Compound 7

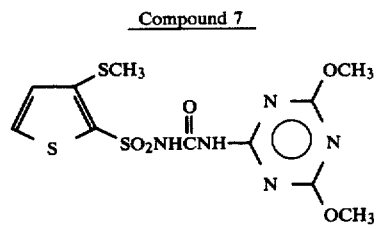

Compound 8

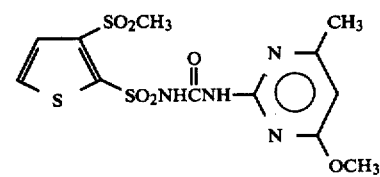

Compound 9

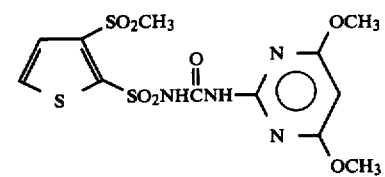

Compound 10

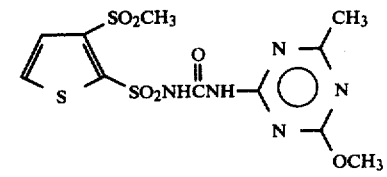

Compound 11

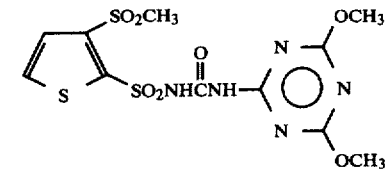

Compound 12

Compound 13

-continued

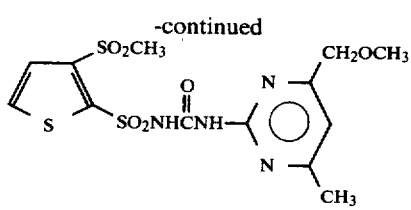
Compound 14

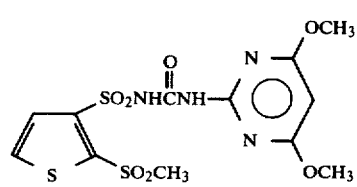
Compound 15

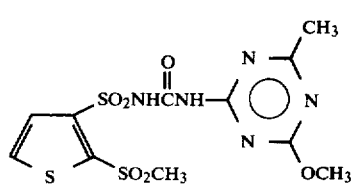
Compound 16

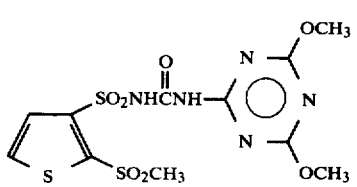
Compound 17

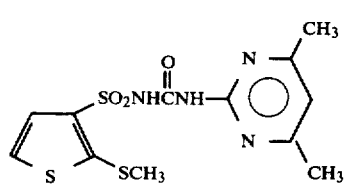
Compound 18

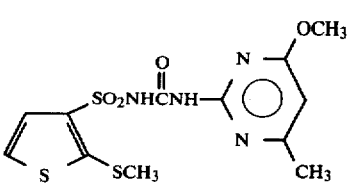
Compound 19

-continued

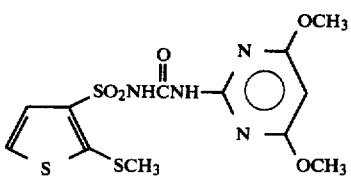
Compound 20

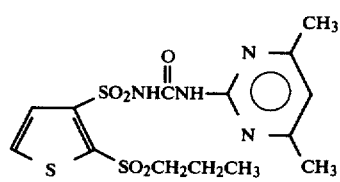
Compound 21

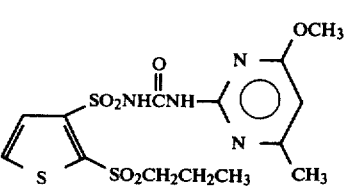
Compound 22

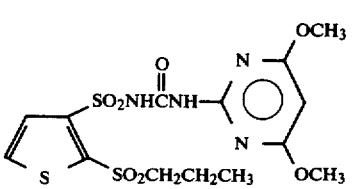
Compound 23

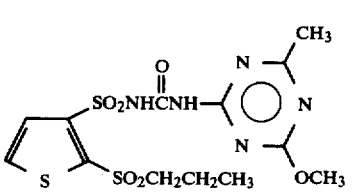
Compound 24

TABLE A

| Rate kg/ha | .05 | .05 | .05 | .05 | .05 | .05 | .05 | .05 | .05 |
|---|---|---|---|---|---|---|---|---|---|
| POST-EMERGENCE | | | | | | | | | |
|  | Cmpd. 1 | Cmpd. 2 | Cmpd. 3 | Cmpd. 4 | Cmpd. 5 | Cmpd. 6 | Cmpd. 7 | Cmpd. 8 | Cmpd. 9 |
| Bush bean | 9C | 2C,9G,6Y | 9C | 8C | 9C | 9C | 9C | 10G,6C | 10C |
| Cotton | 9C | — | 2U,5C,9G | 9C | 9C | 5C,9G | 6C,9G | 10G,8C | 10C |
| Sorghum | 2U,9G | 2C,9H | 6U,9G | 5U | 7U,9G | 4U,9G | 2U,9G | 10C | 10C |
| Corn | 3U,9G | 0 | 7U,9C | 9C | 5C,9G | 9C | 2U,8H | 10G,3C | 10C |
| Soybean | 9C | 2C,8G | 9C | 9C | 9C | 9C | 4C,8G | 10G,3C | 10C |
| Wheat | 1C,9G | 2C,9G | 3U,9G | 2C | 2C,9G | 3G | 0 | 10G,2C | 10G,2C |
| Wild Oats | 5C,9G | 2C,9G | 3C,8G | 5C | 2C,9G | 2G | 0 | 10G,9C | 10G,4C |
| Rice | 9C | 4C,9G | 9C | 9C | 9C | 5C,9G | 4C,9G | 10G,5C | 10G,6C |

TABLE A-continued

| Rate kg/ha | .05 | .05 | .05 | .05 | .05 | .05 | .05 | .05 | .05 |
|---|---|---|---|---|---|---|---|---|---|
| Barnyardgrass | 6C,9H | 2C,5H | 9C | 9C | 9C | 3C,9H | 9H | 10G,9C | 10G,9C |
| Crabgrass | 8G | 2C,6G | 2C,8G | 5C,5C,9G | 3C,9G | 5G | 10G,5C | 10G,5C | |
| Morningglory | 10C | 3C,8H | 3C,9H | 9C | 5C,9G | 1C,5G | 2C,3G | 10G,7C | 10G,5C |
| Cocklebur | 9C | 2C,6G | 10C | 10C | 5C,9G | 9C | 4G | 10G | 10C |
| Cassia | 6C,9G | 3C,6H | 6C,9G | 9C | 9C | 3C,7G | 2C,5G | 10G,9C | 10G,4C |
| Nutsedge | 3C,9G | 0 | 3C,8G | 3C | 9C | 8G | 1C | 10G,3C | 9G,2C |

| | Cmpd. 10 | Cmpd. 11 | Cmpd. 12 | Cmpd. 13 | Cmpd. 14 | Cmpd. 15 | Cmpd. 16 | Cmpd. 17 | Cmpd. 18 |
|---|---|---|---|---|---|---|---|---|---|
| Bush bean | 9G,9C | 9G | 10G,3C | 10G,6C | 9C | 9D,9G,6Y | 1C | 4C,9G,6Y | 9C |
| Cotton | 10C | 8G,2C | 3G | 10G,5C | 9C | 6C,9G | 4C,6H | 4C,4H,9G | 9C |
| Sorghum | 10C | 10G,1C | 10G | 10C | 6C | 2U,9G | 3C,9G | 2U,9G | 3U |
| Corn | 10C | 10G,7U | 9G,5C | 10C | 9C | 9C | 9C | 3U,9G | 3U |
| Soybean | 10G,5C | 7G,3X | 9C,5X | 10G,3H,3C | 9C | 9C | 2C,5H | 2H,8G | 3C |
| Wheat | 9G,3C | 0 2G | 9G,1C | 2C | 2C,5G | 0 | 1C,9G | 3C | |
| Wild Oats | 10G,3C | 0 | 1G | 9G,1C | 4C | 1C | 0 | 3C,9G | 9C |
| Rice | 10G,5C | 10G,2C | 10G,2C | 9C | 5C | 6C,9G | 4C,9G | 4C,9G | 4C |
| Barnyardgrass | 10C | 9C | 9C | 10C | 9C | 9C | 5C,9H | 6C,9H | 9C |
| Crabgrass | 9G,7C | 0 | 0 | 9C | 3C | 3C,7G | 1C | 2C,9G | 3C |
| Morningglory | 10G,4C | 6G | 8G,2C | 10G,10P,3C | 9C | 4C,8H | 2C,7H | 4C,7H | 9C |
| Cocklebur | 10C | 8G | 4G | 9G,2C | 10C | 2C,9H | 2G | 4C,9G | 9C |
| Cassia | 10G,4C | 5G | 6G | 10G,4C | 9C | 3C,7G | 1C | 4C,9G | 9C |
| Nutsedge | 9G,8C | 0 | 0 | 10G,2C | 6C | 5G | 4G | 1C,6G | 5C |

| | Cmpd. 19 | Cmpd. 20 | Cmpd. 21 | Cmpd. 22 | Cmpd. 23 | Cmpd. 24 |
|---|---|---|---|---|---|---|
| Bush bean | 6C,9G,6Y | 3C,9G,6Y | 9C | 9C | 9C | 9C |
| Cotton | 9C | 4C,9H | 6C,9G | 5C,9G | 5C,9G | 9C |
| Sorghum | 8U,9G | 2C,9G | 3C,9G | 5C,9G | 2C,9H | 2C,9G |
| Corn | 5C,9G | 1C,3G | 2C,6G | 2C,7H | 4U,9H | 2U,9H |
| Soybean | 4C,9G | 3H | 1C,6H | 3C,8H | 3H | 1H |
| Wheat | 5C,9G | 0 | 0 | 1C | 0 | 0 |
| Wild Oats | 9C | 0 | 3C | 0 | 0 | 0 |
| Rice | 6C,9G | 1C,9G | 2C,9G | 3C,9G | 2C,8G | 2C,8H |
| Barnyardgrass | 10C | 2C,5H | 4C,9H | 5C,9H | 2C,4H | 1C,2H |
| Crabgrass | 2C,8G | 0 | 1C,3H | 1C,5H | 1C,2G | 1C |
| Morningglory | 5C,9G | 3C,8G | 6C,9G | 4C,9G | 5C,9G | 4C,8H |
| Cocklebur | 5C,9G | 2C,8H | 3C,9G | 9C | 6C,9G | 4C,9G |
| Cassia | 9C | 2C | 3C,9H | 9C | 4C,8H | 4C,7H |
| Nutsedge | 9C | 0 | 1C,6G | 3C,9G | 1C | 0 |

PRE-EMERGENCE

| | Cmpd. 1 | Cmpd. 2 | Cmpd. 3 | Cmpd. 4 | Cmpd. 5 | Cmpd. 6 | Cmpd. 7 | Cmpd. 8 | Cmpd. 9 |
|---|---|---|---|---|---|---|---|---|---|
| Sorghum | 6C,9G | 2C,9H | 10E | 5C,9G | 5C,9H | 2C,8G | 7G | 10E | 10E |
| Corn | 5C,9G | 3C | 10E | 2U,9G | 2C,9G | 2C,8G | 3C,7G | 9G | 10E |
| Soybean | 9H | 2H | 8H | 9H | 9H | 1C,4G | 1C,2H | 9G | 9G |
| Wheat | 9H | 3C,9G | 9H | 4C,9G | 2C,9G | 5G | 2G | 10E | 10E |
| Wild Oats | 5C,9G | 2C,7G | 3C,9G | 5C,9G | 4C,9G | 0 | 2C | 9G | 9G,2C |
| Rice | 10E | 9H | 10E | 10E | 10E | 4C,9H | 3C,8H | 10E | 10E |
| Barnyardgrass | 2C,9H | 2C,6G | 3C,9H | 6C,9H | 5C,9H | 4C,6H | 3C,8H | 9G | 9G,3C |
| Crabgrass | 2C,8G | 1C | 5C,9G | 5C,9G | 5C,9G | 1C | 1C | 9G | 9G,4C |
| Morningglory | 9H | 2C,5H | 9G | 5C,9G | 9G | 8H | 8G | 9G | 9G,3C |
| Cocklebur | 9H | 6G | 9H | 9H | 9H | 8H | 8H | 7G | 9G,10P |
| Cassia | 9G | 3C | 2C,9G | 2C,8G | 9G,2C | 9G,5C | 9G | 8G | 8G,2C |
| Nutsedge | 9G | 0 | 10E | 2C,8G | 10E | 5G | 1C,3G | 9G | 9G |

| | Cmpd. 10 | Cmpd. 11 | Cmpd. 12 | Cmpd. 13 | Cmpd. 14 | Cmpd. 15 | Cmpd. 16 | Cmpd. 17 | Cmpd. 18 |
|---|---|---|---|---|---|---|---|---|---|
| Sorghum | 10E | 9G | 9G | 10E | 10E | 5C,9H | 6C,9H | 9H | 10E |
| Corn | 9G | 9G | 9G | 9G | 10E | 2C,9G | 9H | 9H | 10H |
| Soybean | 9G | 4G | 5G | 9G | 9H | 2C,7H | 1C,2H | 2H,5G | 9H |
| Wheat | 9G,2H | 0 | 0 | 9G | 8G | 1C,3G | 0 | 2C,8G | 9H |
| Wild Oats | 8G,3C | 0 | 0 | 8G | 1C,9G | 2C,5G | 0 | 8G | 5C,9H |
| Rice | 10E | 4G,2C | 8G | 10E | 10E | 4C,8G | 3C,6G | 10E | 10E |
| Barnyardgrass | 9G,2C | 9G | 9G,2C | 9G,3C | 4C,9H | 5C,9H | 2C,5H | 4C,9H | 5C,9H |
| Crabgrass | 9G,2C | 5G | 2G | 9G | 4C,8G | 1C | 0 | 3G | 2C,8G |
| Morningglory | 9G | 5G | 7G | 9G | 9G | 2C,5H | 2H | 9H | 9G |
| Cocklebur | 8G | 7G | 7G | 7G | 9H | 9H | 0 | 9H | 9H |
| Cassia | 8G | 8G | 8G | 8G | 6C,9G | 4C,8H | 2C | 9G | 9G,3C |
| Nutsedge | 10E | 0 | 4G | 9G | 10E | 2C | O | 7G | 2C,9G |

| | Cmpd. 19 | Cmpd. 20 | Cmpd. 21 | Cmpd. 22 | Cmpd. 23 | Cmpd. 24 |
|---|---|---|---|---|---|---|
| Sorghum | 5C,9H | 2C,7H | 9H | 9H | 3C,9H | 2C,9H |
| Corn | 5C,9G | 1C | 2C,8G | 3C,8H | 2C,9G | 2C,9G |
| Soybean | 9H | 1H | 2H | 2G | 1H | 2A |
| Wheat | 2C,8H | 2G | 0 | 1C,2G | 0 | 0 |
| Wild Oats | 2C,9G | 2C,6G | 2C,8G | 2C,6G | 2C,7G | 1C,4G |
| Rice | 10E | 3C,6G | 2C,8H | 5C,8H | 5C,9H | 2C,8H |
| Barnyardgrass | 3C,9H | 2C,7H | 9H,2C | 4C,9H | 1C,5H | 3C,7H |
| Crabgrass | 2C,5G | 1C | 5G | 1C,3G | 1C | 1C |
| Morningglory | 9H | 6H,2C | 9H | 9H | 8H,2C | 2C,7H |
| Cocklebur | 9H | 2C,2H | 9H | — | 3C,8H | 9H |
| Cassia | 5C,9G | 3C | 3C,6H | 2C,5H | 5C | 4C,6H |

| Rate kg/ha | .05 | .05 | .05 | .05 | .05 | .05 | .05 | .05 | .05 |
|---|---|---|---|---|---|---|---|---|---|
| Nutsedge | 10E | 0 | 6G | 10E | 0 | 0 | | | |

Test B

Two plastic bulb pans were filled with fertilized and limed Fallsington silt loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugarbeets. The above four containers were treated pre-emergence with several test compounds within the scope of the invention.

Twenty-eight days after treatment, the plants were evaluated and visually rated for response to the chemical treatments utilizing the rating system described previously for Test A. The data are summarized in Table B.

TABLE B
PRE-EMERGENCE ON FALLSINGTON SILT LOAM

| | Compound 1 | |
|---|---|---|
| Rate kg/ha | 0.03 | 0.12 |
| Crabgrass | 5G | 7G,3H |
| Barnyardgrass | 7G,3H | 8G,8C |
| Sorghum | 9G,8C | 10E |
| Wild Oats | 6G | 6G,3C |
| Johnsongrass | 7G,5H | 8G,5H |
| Dallisgrass | 5G,2H | 7G,3H |
| Giant Foxtail | 7G,5H | 8G,5H |
| Ky. Bluegrass | 4G | 6G,3H |
| Cheatgrass | 7G,3H | 8G,9C |
| Sugarbeets | 8G,8C | 9G,9C |
| Corn | 4G | 7G,5H |
| Mustard | 9G,9C | 9G,9C |
| Cocklebur | 5G | 8G,3H |
| Pigweed | — | — |
| Nutsedge | 5G | 8G |
| Cotton | 5G,5H | 8G,5H |
| Morningglory | 7G,5H | 9G,5H |
| Cassia | 7G | 8G,5C |
| Teaweed | 5G,3C | 8G,8C |
| Velvetleaf | 4G,5H | 8G,6C |
| Jimsonweed | 8G,8C | 8G,9C |
| Soybean | 5G,5H | 9G,5H |
| Rice | 8G,8E | 10E |
| Wheat | 3G | 8G,8E |

Test C

Twenty-five cm diameter plastic pots filled with Fallsington silt loam were planted to soybeans, cotton, alfalfa, corn, rice, wheat, sorghum, velvetleaf, (*Abutilon theophrasti*), sesbania (*Sesbania exaltata*), Cassia (*Cassia tora*), morningglory (*Ipomoea hederacea*), jimsonweed (*Datura stramonium*), cocklebur (*Xanthium pensylvanicum*), crabgrass (*Digitaria* spp.), nutsedge (*Cyperus rotundus*), barnyardgrass (*Echinochloa crusgalli*), giant foxtail (*Setaria faberii*) and wild oats (*Avena fatua*). Approximately 2½ weeks after planting, the young plants and the soil around them were sprayed overall with the test chemicals dissolved in a non-phytotoxic solvent. Fourteen days after treatment, all species were compared to untreated controls and visually rated for response to treatment. The rating system was as described previously for Test A. The data are presented in Table C.

TABLE C
Over-the-Top Soil/Foliage Treatment

| | Compound 1 | | Compound 2 | |
|---|---|---|---|---|
| Rate kg/ha | 0.06 | 0.016 | 0.06 | 0.016 |
| Soybeans | 10G,8C | 10G,8C | 8G,5C | 5G,2C |
| Velvetleaf | 10C | 10C | 8G,2C | 7G,5C |
| Sesbania | 10C | 7G,2C | 2G,3C | 3C |
| Cassia | 7G,2C | 8G,3C | 7G,2C | 3G,3C |
| Cotton | 10C | 10C | 8G,3C | 4G,3C |
| Morningglory | 6G,1C | 5G,1C | 8G,2C | 3G |
| Alfalfa | 7G,4C | 7G,4C | 7G,4C | 1G,2C |
| Jimsonweed | 2C | 2C | 0 | 5G |
| Cocklebur | 8G,2C | 5G,1C | 5G,1C | 0 |
| Corn | 8G,1C | 7G,4C | 1C | 1G |
| Crabgrass | 7G | 6G | 1G | 4G |
| Rice | 5G,1C | 6G | 5G,2C | 4G |
| Nutsedge | 4G | 3G | 0 | 1G |
| Barnyardgrass | 7G,1C | 7G | 6G,1C | 0 |
| Wheat | 5G | 4G | 4G | 4G |
| Giant foxtail | 9G | 7G | 0 | 0 |
| Wild Oats | 6G | 6G | 3G | 2G |
| Sorghum | 7G,1C | 6G,1C | 4G | 4G,3C |
| Mustard | 10C | 9G,9C | 9G,5C | 6G,1C |
| Pigweed | — | — | — | — |
| Johnsongrass | — | — | — | — |
| Sunflower | 10C | 10C | 8G,5C | — |
| Sugarbeets | 10C | 6G,1C | 7G,1C | 6G,1C |

What is claimed is:

1. A compound of the formula:

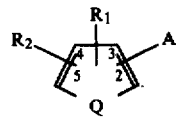

wherein
Q is O or S;
A is

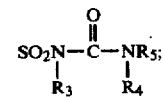

$R_1$ is $R_6S(O)_n$;
$R_6$ is $C_1$-$C_4$ alkyl, $C_3$-$C_4$ alkenyl, cyclopentyl or cyclopropylmethyl;
$R_2$ is H, Cl, Br or $CH_3$;
$R_3$ and $R_4$ are independently H or $CH_3$;
n is 0, 1 or 2; and
$R_5$ is

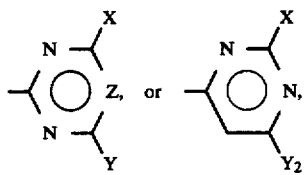

wherein
X is CH₃ or OCH₃;
Y is H, Cl, CH₃, C₂H₅, OCH₃, OC₂H₅ or CH₂OCH₃;
Y₁ is H, Cl, CH₃ or OCH₃;
Y₂ is CH₃ or OCH₃;
Z is CH;
and their agriculturally suitable salts; provided that:
both R₃ and R₄ may not simultaneously be CH₃, and further provided that R₁ and A are bonded to adjacent carbon atoms of the thiophene or furan ring.

2. Compounds of claim 1 wherein Q is S.
3. Compounds of claim 2 where R₂ is H.
4. Compounds of claim 3 where R₆ is C₁-C₃ alkyl.
5. Compounds of claim 4 where n is 2.
6. Compounds of claim 5 where R₅ is

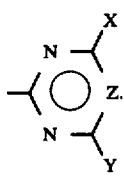

7. Compounds of claim 6 where R₃ is H.
8. Compounds of claim 7 with the structure

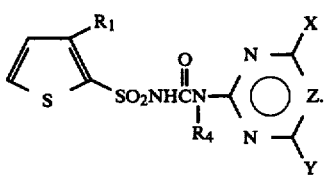

9. Compounds of claim 7 with the structure

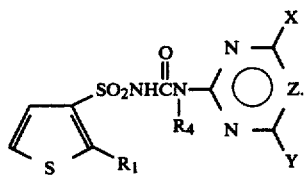

10. Compounds of claim 7 with the structure

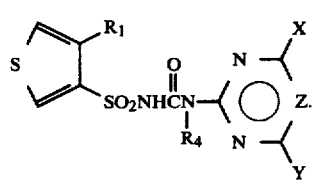

11. Compounds of claim 8 where X is CH₃ or OCH₃; and Y is CH₃, OCH₃, OC₂H₅ or CH₂OCH₃.
12. Compounds of claim 9 where X is CH₃ or OCH₃; and Y is CH₃, OCH₃, OC₂H₅ or CH₂OCH₃.
13. Compounds of claim 10 where X is CH₃ or OCH₃; and Y is CH₃, OCH₃, OC₂H₅ or CH₂OCH₃.
14. Compounds of claim 11 where R₄ is H.
15. Compounds of claim 12 where R₄ is H.
16. Compounds of claim 13 where R₄ is H.
17. Compounds of claim 1 where Q is O.
18. Compounds of claim 17 where R₂ is H.
19. Compounds of claim 18 where R₆ is C₁-C₃ alkyl.
20. Compounds of claim 19 where n is 2.
21. Compounds of claim 20 where R₅ is

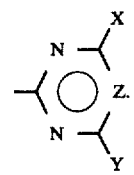

22. Compounds of claim 21 where R₃ is H.
23. Compounds of claim 22 with the structure

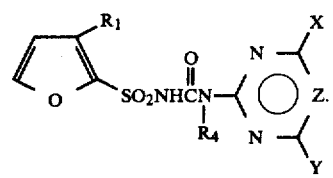

24. Compounds of claim 22 with the structure

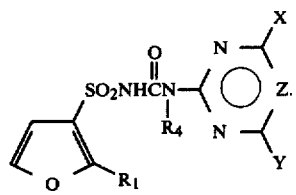

25. Compounds of claim 22 with the structure

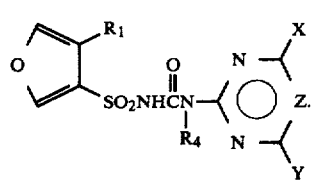

26. The compound of claim 1, N-[(4,6-dimethylpyrimidin-2-yl)aminocarbonyl]-2-(methylsulfonyl)-3-thiophenesulfonamide.
27. The compound of claim 1, N-[(4-methoxy-6-methylpyrimidin-2-yl)aminocarbonyl]-2-(methylsulfonyl)-3-thiophenesulfonamide.
28. The compound of claim 1, N-[(4,6-dimethoxypyrimidin-2-yl)aminocarbonyl]-2-(methylsulfonyl)-3-thiophenesulfonamide.
29. The compound of claim 1, N-[(4,6-dimethoxypyrimidin-2-yl)(methyl)aminocarbonyl]-2-(methylsulfonyl)-3-thiophenesulfonamide.
30. The compound of claim 1, N-[(4-methoxy-6-methylpyrimidin-2-yl)(methyl)aminocarbonyl]-2-(methylsulfonyl)-3-thiophenesulfonamide.
31. A composition suitable for controlling the growth of undesired vegetation which comprises an effective amount of a compound of claim 1 and at least one of the following: surfactant, solid or liquid diluent.

32. A composition suitable for controlling the growth of undesired vegetation which comprises an effective amount of a compound of claim 2 and at least one of the following: surfactant, solid or liquid diluent.

33. A composition suitable for controlling the growth of undesired vegetation which comprises an effective amount of a compound of claim 3 and at least one of the following: surfactant, solid or liquid diluent.

34. A composition suitable for controlling the growth of undesired vegetation which comprises an effective amount of a compound of claim 4 and at least one of the following: surfactant, solid or liquid diluent.

35. A composition suitable for controlling the growth of undesired vegetation which comprises an effective amount of a compound of claim 5 and at least one of the following: surfactant, solid or liquid diluent.

36. A composition suitable for controlling the growth of undesired vegetation which comprises an effective amount of a compound of claim 6 and at least one of the following: surfactant, solid or liquid diluent.

37. A composition suitable for controlling the growth of undesired vegetation which comprises an effective amount of a compound of claim 7 and at least one of the following: surfactant, solid or liquid diluent.

38. A composition suitable for controlling the growth of undesired vegetation which comprises an effective amount of a compound of claim 8 and at least one of the following: surfactant, solid or liquid diluent.

39. A composition suitable for controlling the growth of undesired vegetation which comprises an effective amount of a compound of claim 9 and at least one of the following: surfactant, solid or liquid diluent.

40. A composition suitable for controlling the growth of undesired vegetation which comprises an effective amount of a compound of claim 10 and at least one of the following: surfactant, solid or liquid diluent.

41. A method for controlling the growth of undesired vegetation which comprises applying to the locus to be protected an effective amount of a compound of claim 1.

42. A method for controlling the growth of undesired vegetation which comprises applying to the locus to be protected an effective amount of a compound of claim 2.

43. A method for controlling the growth of undesired vegetation which comprises applying to the locus to be protected an effective amount of a compound of claim 3.

44. A method for controlling the growth of undesired vegetation which comprises applying to the locus to be protected an effective amount of a compound of claim 4.

45. A method for controlling the growth of undesired vegetation which comprises applying to the locus to be protected an effective amount of a compound of claim 5.

46. A method for controlling the growth of undesired vegetation which comprises applying to the locus to be protected an effective amount of a compound of claim 6.

47. A method for controlling the growth of undesired vegetation which comprises applying to the locus to be protected an effective amount of a compound of claim 7.

48. A method for controlling the growth of undesired vegetation which comprises applying to the locus to be protected an effective amount of a compound of claim 8.

49. A method for controlling the growth of undesired vegetation which comprises applying to the locus to be protected an effective amount of a compound of claim 9.

50. A method for controlling the growth of undesired vegetation which comprises applying to the locus to be protected an effective amount of a compound of claim 10.

* * * * *